(12) United States Patent
Wixey et al.

(10) Patent No.: US 11,375,999 B2
(45) Date of Patent: Jul. 5, 2022

(54) SURGICAL STAPLER WITH FIRING LOCK MECHANISM

(71) Applicant: Applied Medical Resources Corporation, Rancho Santa Margarita, CA (US)

(72) Inventors: Matthew A. Wixey, San Jose, CA (US); Gary M. Johnson, Rancho Santa Margarita, CA (US)

(73) Assignee: Applied Medical Resources Corporation, Rancho Santa Margarita, CA (US)

( * ) Notice: Subject to any disclaimer, the term of this patent is extended or adjusted under 35 U.S.C. 154(b) by 234 days.

(21) Appl. No.: 16/583,778

(22) Filed: Sep. 26, 2019

(65) Prior Publication Data
US 2020/0100786 A1    Apr. 2, 2020

Related U.S. Application Data

(63) Continuation of application No. 13/618,453, filed on Sep. 14, 2012, now Pat. No. 10,470,766, which is a
(Continued)

(51) Int. Cl.
*A61B 17/072*    (2006.01)
*A61B 17/068*    (2006.01)
(Continued)

(52) U.S. Cl.
CPC ........ *A61B 17/0686* (2013.01); *A61B 17/072* (2013.01); *A61B 17/105* (2013.01); *A61B 2090/0814* (2016.02)

(58) Field of Classification Search
CPC . A61B 17/0686; A61B 17/072; A61B 17/105; A61B 2090/0814
(Continued)

(56) References Cited

U.S. PATENT DOCUMENTS 2,073,960 A    3/1937 Crosby
2,140,593 A    12/1938 Pankonin
(Continued)

FOREIGN PATENT DOCUMENTS

EP    0251444    1/1988
EP    492283    7/1992
(Continued)

OTHER PUBLICATIONS

European Patent Office, The International Search Report and the Written Opinion of the International Searching Authority for International Application No. PCT/US2020/019938, entitled "Surgical Stapling Instrument Having a Two-Position Mechanism," dated Jun. 18, 2020, 16 pgs.
(Continued)

*Primary Examiner* — Chelsea E Stinson
*Assistant Examiner* — Mary C Hibbert-Copeland
(74) *Attorney, Agent, or Firm* — John F. Heal

(57) ABSTRACT

A surgical stapler is provided that maintains the jaws of the stapler in an open position and prevents firing of staples when a cartridge is not loaded in one of the jaws. Distinct positioning and sequencing of the jaws, capture pin and firing of the staples are provided by a latch mechanism. Such locking and latching mechanisms ensure proper operation of the stapler.

12 Claims, 34 Drawing Sheets

Related U.S. Application Data continuation of application No. 13/100,022, filed on May 3, 2011, now Pat. No. 8,281,972, which is a continuation of application No. 12/796,503, filed on Jun. 8, 2010, now Pat. No. 7,934,629, which is a continuation of application No. 12/495,384, filed on Jun. 30, 2009, now Pat. No. 7,731,073, which is a continuation of application No. 11/805,094, filed on May 21, 2007, now Pat. No. 7,552,854.

(60) Provisional application No. 60/747,790, filed on May 19, 2006.

(51) Int. Cl.
  *A61B 90/00* (2016.01)
  *A61B 17/10* (2006.01)

(58) Field of Classification Search
  USPC .................................................. 227/175.1
  See application file for complete search history.

(56) References Cited

U.S. PATENT DOCUMENTS

| | | |
|---|---|---|
| 2,351,608 A | 6/1944 | Greenwood |
| 2,487,565 A | 11/1949 | Leber et al. |
| 2,641,154 A | 6/1953 | Heller |
| 3,076,373 A | 2/1963 | Matthews |
| 3,077,812 A | 2/1963 | Dietrich |
| 3,080,564 A | 3/1963 | Strekopitov et al. |
| 3,203,220 A | 8/1965 | Kaepernik |
| 3,252,643 A | 5/1966 | Strekopitov et al. |
| 3,273,562 A | 9/1966 | Brown |
| 3,373,646 A | 3/1968 | Ehlert |
| 3,459,187 A | 8/1969 | Pallotta |
| 3,494,533 A | 2/1970 | Green et al. |
| 3,662,939 A | 5/1972 | Bryan |
| 3,675,688 A | 7/1972 | Bryan et al. |
| 3,692,224 A | 9/1972 | Astafiev et al. |
| 4,261,244 A | 4/1981 | Becht et al. |
| 4,281,785 A | 8/1981 | Brooks |
| 4,304,236 A | 12/1981 | Conta et al. |
| 4,312,363 A | 1/1982 | Rothfuss et al. |
| 4,317,451 A | 3/1982 | Cerwin et al. |
| 4,407,286 A | 10/1983 | Noiles et al. |
| 4,434,796 A | 3/1984 | Karapetian et al. |
| 4,442,964 A | 4/1984 | Becht |
| 4,454,875 A | 6/1984 | Pratt et al. |
| 4,522,327 A | 6/1985 | Korthoff et al. |
| 4,527,724 A | 7/1985 | Chow et al. |
| 4,589,582 A | 5/1986 | Bilotti |
| 4,591,085 A | 5/1986 | Di Giovanni |
| 4,606,344 A | 8/1986 | Di Giovanni |
| 4,608,981 A | 9/1986 | Rothfuss et al. |
| 4,610,383 A | 9/1986 | Rothfuss et al. |
| 4,728,020 A | 3/1988 | Green et al. |
| 4,805,823 A | 2/1989 | Rothfuss |
| 4,892,244 A | 1/1990 | Fox et al. |
| 4,923,350 A | 5/1990 | Hinksman et al. |
| 4,941,623 A | 7/1990 | Pruitt |
| 4,955,959 A | 9/1990 | Tompkins et al. |
| 4,978,049 A | 12/1990 | Green |
| 5,031,814 A | 7/1991 | Tompkins et al. |
| 5,065,929 A | 11/1991 | Schulze et al. |
| 5,071,052 A | 12/1991 | Rodak et al. |
| 5,106,008 A | 4/1992 | Tompkins et al. |
| 5,116,349 A | 5/1992 | Aranyi |
| 5,129,570 A | 7/1992 | Schulze et al. |
| 5,201,746 A | 4/1993 | Shichman |
| 5,221,036 A | 6/1993 | Takase |
| 5,236,440 A | 8/1993 | Hlavacek |
| 5,240,163 A | 8/1993 | Stein et al. |
| RE34,519 E | 1/1994 | Fox et al. |
| 5,275,323 A | 1/1994 | Schulze et al. |
| 5,289,963 A | 3/1994 | McGarry et al. |
| D347,474 S | 5/1994 | Olson |
| 5,307,976 A | 5/1994 | Olson et al. |
| 5,308,576 A | 5/1994 | Green et al. |
| 5,326,013 A | 7/1994 | Green et al. |
| 5,350,400 A | 9/1994 | Esposito et al. |
| 5,360,305 A | 11/1994 | Kerrigan |
| 5,364,002 A | 11/1994 | Green et al. |
| 5,366,479 A | 11/1994 | McGarry et al. |
| 5,381,943 A | 1/1995 | Allen et al. |
| 5,389,098 A | 2/1995 | Tsuruta et al. |
| 5,395,034 A | 3/1995 | Allen et al. |
| 5,397,046 A | 3/1995 | Savage et al. |
| 5,413,267 A | 5/1995 | Solyntjes et al. |
| 5,415,334 A | 5/1995 | Williamson, IV et al. |
| 5,415,335 A | 5/1995 | Knodell, Jr. |
| 5,439,155 A | 8/1995 | Vioila |
| 5,439,479 A | 8/1995 | Shichman et al. |
| 5,445,304 A | 8/1995 | Plyley et al. |
| 5,447,265 A | 9/1995 | Vidal et al. |
| 5,452,836 A | 9/1995 | Huitema et al. |
| 5,456,401 A | 10/1995 | Green et al. |
| 5,458,279 A | 10/1995 | Plyley |
| 5,462,215 A | 10/1995 | Viola et al. |
| 5,464,144 A | 11/1995 | Guy et al. |
| 5,465,895 A | 11/1995 | Knodel et al. |
| 5,470,006 A | 11/1995 | Rodak |
| 5,470,007 A | 11/1995 | Plyley et al. |
| 5,470,008 A | 11/1995 | Rodak |
| 5,470,009 A | 11/1995 | Rodak |
| 5,472,132 A | 12/1995 | Savage et al. |
| 5,480,089 A | 1/1996 | Blewett |
| 5,485,952 A | 1/1996 | Fontayne |
| 5,487,500 A | 1/1996 | Knodel et al. |
| 5,489,058 A | 2/1996 | Plyley |
| 5,497,933 A | 3/1996 | DeFonzo et al. |
| 5,507,426 A | 4/1996 | Young et al. |
| 5,507,773 A | 4/1996 | Huitema et al. |
| 5,509,596 A | 4/1996 | Green et al. |
| 5,509,920 A | 4/1996 | Phillips et al. |
| 5,529,235 A | 6/1996 | Boiarski et al. |
| 5,547,117 A | 8/1996 | Hamblin et al. |
| 5,553,765 A | 9/1996 | Knodel et al. |
| 5,554,164 A | 9/1996 | Wilson et al. |
| 5,558,266 A | 9/1996 | Green et al. |
| 5,562,241 A | 10/1996 | Knodel et al. |
| 5,562,700 A | 10/1996 | Huitema et al. |
| 5,562,701 A | 10/1996 | Huitema et al. |
| 5,562,702 A | 10/1996 | Huitema et al. |
| 5,564,615 A | 10/1996 | Bishop et al. |
| 5,571,285 A | 11/1996 | Chow et al. |
| 5,579,978 A | 12/1996 | Green et al. |
| 5,580,067 A | 12/1996 | Hamblin et al. |
| 5,584,425 A | 12/1996 | Savage et al. |
| 5,586,711 A | 12/1996 | Plyley et al. |
| 5,588,581 A | 12/1996 | Conlon et al. |
| 5,597,107 A | 1/1997 | Knodel et al. |
| 5,601,224 A | 2/1997 | Bishop et al. |
| 5,605,272 A | 2/1997 | Witt et al. |
| 5,607,095 A | 3/1997 | Smith et al. |
| 5,615,820 A | 4/1997 | Viola |
| 5,626,587 A | 5/1997 | Bishop et al. |
| 5,630,539 A | 5/1997 | Plyley et al. |
| 5,634,584 A | 6/1997 | Okorocha et al. |
| 5,636,779 A | 6/1997 | Palmer |
| 5,657,921 A | 8/1997 | Young et al. |
| 5,662,258 A | 9/1997 | Knodel et al. |
| 5,662,662 A | 9/1997 | Bishop et al. |
| 5,662,667 A | 9/1997 | Knodel |
| 5,673,840 A | 10/1997 | Schulze et al. |
| 5,673,841 A | 10/1997 | Schulze et al. |
| 5,673,842 A | 10/1997 | Bittner et al. |
| 5,676,674 A | 10/1997 | Bolanos et al. |
| 5,678,748 A | 10/1997 | Plyley |
| 5,680,982 A | 10/1997 | Schulze et al. |
| 5,680,983 A | 10/1997 | Plyley et al. |
| 5,697,542 A | 12/1997 | Knodel et al. |
| 5,697,543 A | 12/1997 | Burdorff |
| 5,704,534 A | 1/1998 | Huitema et al. |
| 5,704,898 A | 1/1998 | Kokish |

(56) References Cited

U.S. PATENT DOCUMENTS

| | | |
|---|---|---|
| 5,706,998 A | 1/1998 | Blyley et al. |
| 5,709,334 A | 1/1998 | Sorrentino et al. |
| 5,713,505 A | 2/1998 | Huitema |
| 5,715,988 A | 2/1998 | Palmer |
| 5,718,359 A | 2/1998 | Palmer et al. |
| 5,732,871 A | 3/1998 | Clark et al. |
| 5,735,445 A | 4/1998 | Vidal et al. |
| 5,762,255 A | 6/1998 | Chrisman et al. |
| 5,762,256 A | 6/1998 | Mastri et al. |
| 5,779,130 A | 7/1998 | Alesi et al. |
| 5,782,396 A | 7/1998 | Mastri et al. |
| 5,782,397 A | 7/1998 | Koukline |
| 5,785,232 A | 7/1998 | Vidal et al. |
| 5,794,834 A | 8/1998 | Hamblin et al. |
| 5,797,536 A | 8/1998 | Smith et al. |
| 5,797,537 A | 8/1998 | Oberlin et al. |
| 5,797,538 A | 8/1998 | Heaton et al. |
| 5,810,240 A | 9/1998 | Robertson |
| 5,814,055 A | 9/1998 | Knodel et al. |
| 5,820,009 A | 10/1998 | Melling et al. |
| 5,829,662 A | 11/1998 | Allen et al. |
| 5,860,995 A | 1/1999 | Berkelaar |
| 5,865,361 A | 2/1999 | Milliman et al. |
| 5,878,937 A | 3/1999 | Green et al. |
| 5,878,938 A | 3/1999 | Bittner et al. |
| 5,893,506 A | 4/1999 | Powell |
| 5,894,979 A | 4/1999 | Powell |
| 5,901,895 A | 5/1999 | Heaton et al. |
| 5,918,791 A | 7/1999 | Sorrentiono et al. |
| 5,954,259 A | 9/1999 | Viola et al. |
| 5,964,394 A | 10/1999 | Robertson |
| D416,089 S | 11/1999 | Barton et al. |
| 5,988,479 A | 11/1999 | Palmer |
| 6,032,849 A | 3/2000 | Mastri et al. |
| 6,053,390 A | 4/2000 | Green et al. |
| 6,079,606 A | 6/2000 | Milliman et al. |
| 6,109,500 A | 8/2000 | Alli et al. |
| 6,131,789 A | 10/2000 | Schulze et al. |
| 6,155,473 A | 12/2000 | Tompkins et al. |
| D441,865 S | 5/2001 | Racenet et al. |
| 6,241,139 B1 | 6/2001 | Milliman et al. |
| 6,250,532 B1 | 6/2001 | Green et al. |
| 6,264,087 B1 | 7/2001 | Whitman |
| 6,270,453 B1 | 8/2001 | Sakai |
| 6,325,810 B1 | 12/2001 | Hamilton et al. |
| 6,330,965 B1 | 12/2001 | Milliman et al. |
| 6,488,196 B1 | 12/2002 | Fenton, Jr. |
| 6,550,757 B2 | 4/2003 | Sesek |
| 6,569,171 B2 | 5/2003 | DeGuillebon et al. |
| 6,595,509 B2 | 7/2003 | Sesek |
| 6,619,529 B2 | 9/2003 | Green et al. |
| 6,644,532 B2 | 11/2003 | Green et al. |
| 6,669,073 B2 | 12/2003 | Milliman et al. |
| 6,716,233 B1 | 4/2004 | Whitman |
| 6,786,382 B1 | 9/2004 | Hoffman |
| 6,817,508 B1 | 11/2004 | Racenet et al. |
| 6,821,282 B2 | 11/2004 | Perry et al. |
| 6,835,199 B2 | 12/2004 | McGuckin, Jr. et al. |
| 6,913,181 B2 | 7/2005 | Mochizuki et al. |
| 6,923,360 B2 | 8/2005 | Sesek et al. |
| 6,953,138 B1 | 10/2005 | Dworak et al. |
| 6,953,139 B2 | 10/2005 | Milliman et al. |
| 6,964,363 B2 | 11/2005 | Wales et al. |
| 6,978,921 B2 | 12/2005 | Shelton, IV et al. |
| 6,986,451 B1 | 1/2006 | Mastri et al. |
| 6,988,649 B2 | 1/2006 | Shelton, IV et al. |
| 7,000,818 B2 | 2/2006 | Shelton, IV et al. |
| 7,044,352 B2 | 5/2006 | Shelton, IV et al. |
| 7,044,353 B2 | 5/2006 | Mastri et al. |
| 7,044,947 B2 | 5/2006 | de la Torre et al. |
| 7,055,730 B2 | 6/2006 | Ehrenfels et al. |
| 7,070,083 B2 | 7/2006 | Jankowski |
| 7,097,089 B2 | 8/2006 | Marczyk |
| 7,097,650 B2 | 8/2006 | Weller et al. |
| 7,108,472 B2 | 9/2006 | Norris et al. |
| 7,128,253 B2 | 10/2006 | Mastri et al. |
| 7,140,527 B2 | 11/2006 | Ehrenfels et al. |
| 7,140,528 B2 | 11/2006 | Shelton, IV |
| 7,143,923 B2 | 12/2006 | Shelton, IV et al. |
| 7,143,924 B2 | 12/2006 | Scirica et al. |
| 7,147,139 B2 | 12/2006 | Schwemberger et al. |
| 7,213,736 B2 | 5/2007 | Wales et al. |
| 7,225,964 B2 | 6/2007 | Mastri et al. |
| 7,237,708 B1 | 7/2007 | Guy et al. |
| 7,258,262 B2 | 8/2007 | Mastri et al. |
| 7,275,674 B2 | 10/2007 | Racenet et al. |
| 7,278,562 B2 | 10/2007 | Mastri et al. |
| 7,290,692 B2 | 11/2007 | Marks |
| 7,293,685 B2 | 11/2007 | Ehrenfels et al. |
| 7,303,107 B2 | 12/2007 | Milliman et al. |
| 7,308,998 B2 | 12/2007 | Mastri et al. |
| 7,328,828 B2 | 2/2008 | Ortiz et al. |
| 7,334,717 B2 | 2/2008 | Rethy et al. |
| 7,380,695 B2 | 6/2008 | Doll et al. |
| 7,380,696 B2 | 6/2008 | Shelton, IV et al. |
| 7,398,908 B2 | 7/2008 | Holsten et al. |
| 7,399,310 B2 | 7/2008 | Edoga et al. |
| 7,401,721 B2 | 7/2008 | Holsten et al. |
| 7,404,508 B2 | 7/2008 | Smith et al. |
| 7,407,075 B2 | 8/2008 | Holsten et al. |
| 7,407,078 B2 | 8/2008 | Shelton, IV et al. |
| 7,416,101 B2 | 8/2008 | Shelton, IV et al. |
| RE40,514 E | 9/2008 | Mastri et al. |
| 7,419,080 B2 | 9/2008 | Smith et al. |
| 7,419,081 B2 | 9/2008 | Ehrenfels et al. |
| 7,422,136 B1 | 9/2008 | Marczyk |
| 7,422,139 B2 | 9/2008 | Shelton, IV et al. |
| 7,431,188 B1 | 10/2008 | Marczyk |
| 7,434,715 B2 | 10/2008 | Shelton, IV et al. |
| 7,434,716 B2 | 10/2008 | Viola |
| 7,455,208 B2 | 11/2008 | Wales et al. |
| 7,455,676 B2 | 11/2008 | Holsten et al. |
| 7,461,767 B2 | 12/2008 | Viola et al. |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,467,740 B2 | 12/2008 | Shelton, IV et al. |
| 7,472,814 B2 | 1/2009 | Mastri et al. |
| 7,472,815 B2 | 1/2009 | Shelton, IV et al. |
| 7,472,816 B2 | 1/2009 | Holsten et al. |
| 7,481,348 B2 | 1/2009 | Marczyk |
| 7,481,349 B2 | 1/2009 | Holsten et al. |
| 7,487,899 B2 | 2/2009 | Shelton, IV et al. |
| 7,490,749 B2 | 2/2009 | Schall et al. |
| 7,506,790 B2 | 3/2009 | Shelton, IV |
| 7,506,791 B2 | 3/2009 | Omaits et al. |
| 7,513,408 B2 | 4/2009 | Shelton, IV et al. |
| 7,530,484 B1 | 5/2009 | Durrani |
| 7,543,730 B1 | 6/2009 | Marczyk |
| 7,543,731 B2 | 6/2009 | Green et al. |
| 7,546,940 B2 | 6/2009 | Milliman et al. |
| 7,549,564 B2 | 6/2009 | Boudreaux |
| 7,556,186 B2 | 7/2009 | Milliman |
| 7,565,993 B2 | 7/2009 | Milliman et al. |
| 7,568,604 B2 | 8/2009 | Ehrenfels et al. |
| 7,588,174 B2 | 9/2009 | Holsten et al. |
| 7,588,175 B2 | 9/2009 | Timm et al. |
| 7,588,177 B2 | 9/2009 | Racenet |
| 7,604,151 B2 | 10/2009 | Hess et al. |
| 7,611,038 B2 | 11/2009 | Racenet et al. |
| 7,617,961 B2 | 11/2009 | Viola |
| 7,624,902 B2 | 12/2009 | Marczyk et al. |
| 7,631,793 B2 | 12/2009 | Rethy et al. |
| 7,635,074 B2 | 12/2009 | Olson et al. |
| 7,637,409 B2 | 12/2009 | Marczyk |
| 7,637,410 B2 | 12/2009 | Marczyk |
| 7,641,091 B2 | 1/2010 | Olson et al. |
| 7,641,093 B2 | 1/2010 | Doll et al. |
| 7,641,095 B2 | 1/2010 | Viola |
| 7,644,848 B2 | 1/2010 | Swayze et al. |
| 7,648,055 B2 | 1/2010 | Marczyk |
| 7,651,017 B2 | 1/2010 | Ortiz et al. |
| 7,654,431 B2 | 2/2010 | Hueil et al. |
| 7,658,311 B2 | 2/2010 | Boudreaux |

(56) References Cited

U.S. PATENT DOCUMENTS

| | | |
|---|---|---|
| 7,665,647 B2 | 2/2010 | Shelton, IV et al. |
| 7,669,746 B2 | 3/2010 | Shelton, IV |
| 7,670,334 B2 | 3/2010 | Hueil et al. |
| 7,673,781 B2 | 3/2010 | Swayze et al. |
| 7,682,367 B2 | 3/2010 | Shah et al. |
| 7,690,547 B2 | 4/2010 | Racenet et al. |
| 7,703,653 B2 | 4/2010 | Shah et al. |
| 7,717,312 B2 | 5/2010 | Beetel |
| 7,721,931 B2 | 5/2010 | Shelton, IV et al. |
| 7,721,933 B2 | 5/2010 | Ehrenfels et al. |
| 7,721,935 B2 | 5/2010 | Racenet et al. |
| 7,721,936 B2 | 5/2010 | Shelton, IV et al. |
| 7,726,538 B2 | 6/2010 | Holsten et al. |
| 7,726,539 B2 | 6/2010 | Holsten et al. |
| 7,735,703 B2 | 6/2010 | Morgan et al. |
| 7,753,245 B2 | 7/2010 | Boudreaux et al. |
| 7,753,246 B2 | 7/2010 | Scirica |
| 7,757,925 B2 | 7/2010 | Viola et al. |
| 7,766,210 B2 | 8/2010 | Shelton, IV et al. |
| 7,770,774 B2 | 8/2010 | Mastri et al. |
| 7,780,054 B2 | 8/2010 | Wales |
| 7,780,055 B2 | 8/2010 | Scirica et al. |
| 7,784,662 B2 | 8/2010 | Wales et al. |
| 7,784,663 B2 | 8/2010 | Shelton, IV |
| 7,793,812 B2 | 9/2010 | Moore et al. |
| 7,798,386 B2 | 9/2010 | Schall et al. |
| 7,810,693 B2 | 10/2010 | Broehl et al. |
| 7,815,090 B2 | 10/2010 | Marczyk |
| 7,815,091 B2 | 10/2010 | Marczyk |
| 7,819,298 B2 | 10/2010 | Hall et al. |
| 7,819,896 B2 | 10/2010 | Racenet |
| 7,823,760 B2 | 11/2010 | Zemlok et al. |
| 7,828,188 B2 | 11/2010 | Jankowski |
| 7,828,189 B2 | 11/2010 | Holsten et al. |
| 7,837,079 B2 | 11/2010 | Holsten et al. |
| 7,837,081 B2 | 11/2010 | Holsten et al. |
| 7,845,534 B2 | 12/2010 | Viola et al. |
| 7,845,535 B2 | 12/2010 | Scircia |
| 7,845,537 B2 | 12/2010 | Shelton, IV et al. |
| 7,857,184 B2 | 12/2010 | Viola |
| 7,857,185 B2 | 12/2010 | Swayze et al. |
| 7,857,187 B2 | 12/2010 | Milliman |
| 7,861,906 B2 | 1/2011 | Doll et al. |
| 7,866,525 B2 | 1/2011 | Scirica |
| 7,866,527 B2 | 1/2011 | Hall et al. |
| 7,891,534 B2 | 2/2011 | Wenchell et al. |
| 7,905,381 B2 | 3/2011 | Baxter, III et al. |
| 7,909,220 B2 | 3/2011 | Viola |
| 7,909,221 B2 | 3/2011 | Viola et al. |
| 7,913,891 B2 | 3/2011 | Doll et al. |
| 7,914,543 B2 | 3/2011 | Roth et al. |
| 7,918,230 B2 | 4/2011 | Whitman et al. |
| 7,918,376 B1 | 4/2011 | Knodel et al. |
| 7,918,377 B2 | 4/2011 | Measamer et al. |
| 7,922,063 B2 | 4/2011 | Zemlok et al. |
| 7,934,628 B2 | 5/2011 | Wenchell et al. |
| 7,934,630 B2 | 5/2011 | Shelton, IV et al. |
| 7,942,300 B2 | 5/2011 | Rethy et al. |
| 7,954,685 B2 | 6/2011 | Viola |
| 7,954,686 B2 | 6/2011 | Baxter, III et al. |
| 7,959,050 B2 | 6/2011 | Smith et al. |
| 7,963,433 B2 | 6/2011 | Whitman et al. |
| 7,992,758 B2 | 8/2011 | Whitman et al. |
| 8,002,795 B2 | 8/2011 | Beetel |
| 8,006,887 B2 | 8/2011 | Marczyk |
| 8,007,513 B2 | 8/2011 | Nalagatla et al. |
| 8,008,598 B2 | 8/2011 | Whitman et al. |
| 8,011,550 B2 | 9/2011 | Aranyi et al. |
| 8,011,553 B2 | 9/2011 | Mastri et al. |
| 8,012,170 B2 | 9/2011 | Whitman et al. |
| 8,016,178 B2 | 9/2011 | Olson et al. |
| 8,020,742 B2 | 9/2011 | Marczyk |
| 8,020,743 B2 | 9/2011 | Shelton, IV |
| 8,028,885 B2 | 10/2011 | Smith et al. |
| 8,033,438 B2 | 10/2011 | Scirica |
| 8,033,440 B2 | 10/2011 | Wenchell et al. |
| 8,033,441 B2 | 10/2011 | Marczyk |
| 8,033,442 B2 | 10/2011 | Racenet et al. |
| 8,034,077 B2 | 10/2011 | Smith et al. |
| 8,038,046 B2 | 10/2011 | Smith et al. |
| 8,052,024 B2 | 11/2011 | Viola et al. |
| 8,056,788 B2 | 11/2011 | Mastri et al. |
| 8,056,789 B1 | 11/2011 | White et al. |
| 8,061,576 B2 | 11/2011 | Cappola |
| 8,061,577 B2 | 11/2011 | Racenet et al. |
| 8,070,033 B2 | 12/2011 | Milliman et al. |
| 8,070,034 B1 | 12/2011 | Knodel |
| 8,070,035 B2 | 12/2011 | Holsten et al. |
| 8,070,036 B1 | 12/2011 | Knodel |
| 8,074,861 B2 | 12/2011 | Ehrenfels et al. |
| 8,083,118 B2 | 12/2011 | Milliman et al. |
| 8,087,563 B2 | 1/2012 | Milliman et al. |
| 8,091,753 B2 | 1/2012 | Viola |
| 8,091,754 B2 | 1/2012 | Ehrenfels et al. |
| 8,092,493 B2 | 1/2012 | Marczyk |
| 8,100,309 B2 | 1/2012 | Marczyk |
| 8,113,406 B2 | 2/2012 | Holsten et al. |
| 8,113,407 B2 | 2/2012 | Holsten et al. |
| 8,113,408 B2 | 2/2012 | Wenchell et al. |
| 8,113,410 B2 | 2/2012 | Hall et al. |
| 8,118,207 B2 | 2/2012 | Racenet et al. |
| 8,123,100 B2 | 2/2012 | Holsten et al. |
| 8,127,976 B2 | 3/2012 | Scirica et al. |
| 8,136,712 B2 | 3/2012 | Zingman |
| 8,152,041 B2 | 4/2012 | Kostrzewski |
| 8,157,145 B2 | 4/2012 | Shelton, IV et al. |
| 8,157,150 B2 | 4/2012 | Viola et al. |
| 8,157,152 B2 | 4/2012 | Holsten et al. |
| 8,181,839 B2 | 5/2012 | Beetel |
| 8,186,555 B2 | 5/2012 | Shelton, IV et al. |
| 8,186,556 B2 | 5/2012 | Viola |
| 8,186,560 B2 | 5/2012 | Hess et al. |
| 8,191,752 B2 | 6/2012 | Scirica |
| 8,196,795 B2 | 6/2012 | Moore et al. |
| 8,201,721 B2 | 6/2012 | Zemlok et al. |
| 8,205,619 B2 | 6/2012 | Shah et al. |
| 8,205,780 B2 | 6/2012 | Sorrentino et al. |
| 8,205,781 B2 | 6/2012 | Baxter, III et al. |
| 8,210,411 B2 | 7/2012 | Yates et al. |
| 8,210,416 B2 | 7/2012 | Milliman et al. |
| 8,220,688 B2 | 7/2012 | Laurent et al. |
| 8,225,979 B2 | 7/2012 | Farascioni et al. |
| 8,231,040 B2 | 7/2012 | Zemlok et al. |
| 8,231,041 B2 | 7/2012 | Marczyk et al. |
| 8,235,274 B2 | 8/2012 | Cappola |
| 8,236,010 B2 | 8/2012 | Ortiz et al. |
| 8,240,536 B2 | 8/2012 | Marczyk |
| 8,240,537 B2 | 8/2012 | Marczyk |
| 8,241,322 B2 | 8/2012 | Whitman et al. |
| 8,245,898 B2 | 8/2012 | Smith et al. |
| 8,245,899 B2 | 8/2012 | Swensgard et al. |
| 8,245,900 B2 | 8/2012 | Scirica |
| 8,256,656 B2 | 9/2012 | Milliman et al. |
| 8,272,552 B2 | 9/2012 | Holsten et al. |
| 8,272,554 B2 | 9/2012 | Whitman et al. |
| 8,281,972 B2 | 10/2012 | Wixey et al. |
| 8,281,973 B2 | 10/2012 | Wenchell et al. |
| 8,286,846 B2 | 10/2012 | Smith et al. |
| 8,292,146 B2 | 10/2012 | Holsten et al. |
| 8,292,148 B2 | 10/2012 | Viola |
| 8,292,151 B2 | 10/2012 | Viola |
| 8,292,152 B2 | 10/2012 | Milliman et al. |
| 8,292,153 B2 | 10/2012 | Jankowski |
| 8,292,157 B2 | 10/2012 | Smith et al. |
| 8,308,041 B2 | 11/2012 | Kostrzewski |
| 8,308,043 B2 | 11/2012 | Bindra et al. |
| 8,317,070 B2 | 11/2012 | Hueil et al. |
| 8,322,455 B2 | 12/2012 | Shelton, IV et al. |
| 8,336,754 B2 | 12/2012 | Cappola et al. |
| 8,342,377 B2 | 1/2013 | Milliman et al. |
| 8,342,378 B2 | 1/2013 | Marczyk et al. |
| 8,342,379 B2 | 1/2013 | Whitman et al. |
| 8,342,380 B2 | 1/2013 | Viola |
| 8,348,125 B2 | 1/2013 | Viola et al. |

(56) References Cited

U.S. PATENT DOCUMENTS

| | | |
|---|---|---|
| 8,348,129 B2 | 1/2013 | Bedi et al. |
| 8,348,131 B2 | 1/2013 | Omaits et al. |
| 8,353,440 B2 | 1/2013 | Whitman et al. |
| 8,360,297 B2 | 1/2013 | Shelton, IV et al. |
| 8,360,299 B2 | 1/2013 | Zemlok et al. |
| 8,393,513 B2 | 3/2013 | Jankowski |
| 8,397,972 B2 | 3/2013 | Kostrzewski |
| 8,397,973 B1 | 3/2013 | Hausen |
| 8,403,198 B2 | 3/2013 | Sorrentino et al. |
| 8,413,868 B2 | 4/2013 | Cappola |
| 8,414,577 B2 | 4/2013 | Boudreaux et al. |
| 8,418,906 B2 | 4/2013 | Farascioni et al. |
| 8,418,907 B2 | 4/2013 | Johnson et al. |
| 8,418,908 B1 | 4/2013 | Beardsley |
| 8,419,768 B2 | 4/2013 | Marczyk |
| 8,439,246 B1 | 5/2013 | Knodel |
| 8,444,036 B2 | 5/2013 | Shelton, IV |
| 8,453,907 B2 | 6/2013 | Laurent et al. |
| 8,453,912 B2 | 6/2013 | Mastri et al. |
| 8,453,913 B2 | 6/2013 | Milliman |
| 8,459,520 B2 | 6/2013 | Giordano et al. |
| 8,459,522 B2 | 6/2013 | Marczyk |
| 8,464,922 B2 | 6/2013 | Marczyk |
| 8,469,252 B2 | 6/2013 | Holcomb et al. |
| 8,479,967 B2 | 7/2013 | Marczyk |
| 8,496,152 B2 | 7/2013 | Viola |
| 8,496,155 B2 | 7/2013 | Knodel |
| 8,496,156 B2 | 7/2013 | Sniffin et al. |
| 8,496,683 B2 | 7/2013 | Prommersberger et al. |
| 8,505,799 B2 | 8/2013 | Viola et al. |
| 8,505,801 B2 | 8/2013 | Ehrenfels et al. |
| 8,517,239 B2 | 8/2013 | Scheib et al. |
| 8,517,240 B1 | 8/2013 | Mata et al. |
| 8,523,043 B2 | 9/2013 | Ullrich et al. |
| 8,540,130 B2 | 9/2013 | Moore et al. |
| 8,540,133 B2 | 9/2013 | Bedi et al. |
| 8,540,625 B2 | 9/2013 | Miyoshi |
| 8,544,712 B2 | 10/2013 | Jankowski |
| 8,556,151 B2 | 10/2013 | Viola |
| 8,556,152 B2 | 10/2013 | Marczyk et al. |
| 8,556,153 B1 | 10/2013 | Knodel |
| 8,561,871 B2 | 10/2013 | Rajappa et al. |
| 8,561,874 B2 | 10/2013 | Scirica |
| 8,573,459 B2 | 11/2013 | Smith et al. |
| 8,573,460 B2 | 11/2013 | Cappola |
| 8,573,462 B2 | 11/2013 | Smith et al. |
| 8,573,463 B2 | 11/2013 | Scirica et al. |
| 8,573,464 B2 | 11/2013 | Nalagatla et al. |
| 8,579,176 B2 | 11/2013 | Smith et al. |
| 8,579,177 B2 | 11/2013 | Beetel |
| 8,584,919 B2 | 11/2013 | Hueil et al. |
| 8,584,921 B2 | 11/2013 | Scirica |
| 8,596,513 B2 | 12/2013 | Olson |
| 8,608,043 B2 | 12/2013 | Scirica |
| 8,608,045 B2 | 12/2013 | Smith et al. |
| 8,616,427 B2 | 12/2013 | Viola |
| 8,622,274 B2 | 1/2014 | Yates et al. |
| 8,627,992 B2 | 1/2014 | Edoga et al. |
| 8,627,993 B2 | 1/2014 | Smith et al. |
| 8,627,995 B2 | 1/2014 | Smith et al. |
| 8,631,990 B1 | 1/2014 | Park et al. |
| 8,632,525 B2 | 1/2014 | Kerr et al. |
| 8,632,535 B2 | 1/2014 | Shelton, IV et al. |
| 8,636,189 B1 | 1/2014 | Knodel et al. |
| 8,636,190 B2 | 1/2014 | Zemlok et al. |
| 8,636,192 B2 | 1/2014 | Farascioni et al. |
| 8,636,193 B2 | 1/2014 | Whitman et al. |
| 8,636,762 B2 | 1/2014 | Whitman et al. |
| 8,636,766 B2 | 1/2014 | Milliman et al. |
| 8,657,174 B2 | 2/2014 | Yates et al. |
| 8,657,176 B2 | 2/2014 | Shelton, IV et al. |
| 8,657,178 B2 | 2/2014 | Hueil et al. |
| 8,672,209 B2 | 3/2014 | Crainich |
| 8,672,951 B2 | 3/2014 | Smith et al. |
| 8,685,004 B2 | 4/2014 | Zemlock et al. |
| 8,695,865 B2 | 4/2014 | Smith et al. |
| 8,696,665 B2 | 4/2014 | Hunt et al. |
| 8,708,211 B2 | 4/2014 | Zemlok et al. |
| 8,708,213 B2 | 4/2014 | Shelton, IV et al. |
| 8,740,034 B2 | 6/2014 | Morgan et al. |
| 8,740,035 B2 | 6/2014 | Mastri et al. |
| 8,740,036 B2 | 6/2014 | Williams |
| 8,752,748 B2 | 6/2014 | Whitman et al. |
| 8,763,876 B2 | 7/2014 | Kostrzewski |
| 8,770,458 B2 | 7/2014 | Scirica |
| 8,770,459 B2 | 7/2014 | Racenet et al. |
| 8,789,741 B2 | 7/2014 | Baxter, III et al. |
| 8,800,839 B2 | 8/2014 | Beetel |
| 8,800,840 B2 | 8/2014 | Jankowski |
| 8,800,841 B2 | 8/2014 | Ellerhorst et al. |
| 8,806,973 B2 | 8/2014 | Ross et al. |
| 8,807,414 B2 | 8/2014 | Ross et al. |
| 8,820,603 B2 | 9/2014 | Shelton, IV et al. |
| 8,820,608 B2 | 9/2014 | Miyamoto |
| 8,833,631 B2 | 9/2014 | Munro, III et al. |
| 8,840,003 B2 | 9/2014 | Morgan et al. |
| 8,858,571 B2 | 10/2014 | Shelton, IV et al. |
| 8,875,971 B2 | 11/2014 | Hall et al. |
| 8,875,972 B2 | 11/2014 | Weisenburgh, II et al. |
| 8,887,979 B2 | 11/2014 | Mastri et al. |
| 8,899,462 B2 | 12/2014 | Kostrzewski et al. |
| 8,899,463 B2 | 12/2014 | Schall et al. |
| 8,905,288 B2 | 12/2014 | Wenchell |
| 8,920,435 B2 | 12/2014 | Smith et al. |
| 8,925,783 B2 | 1/2015 | Zemlok et al. |
| 8,931,679 B2 | 1/2015 | Kostrzewski |
| 8,931,683 B2 | 1/2015 | Racenet et al. |
| 8,939,343 B2 | 1/2015 | Milliman et al. |
| 8,967,444 B2 | 3/2015 | Beetel |
| 8,967,446 B2 | 3/2015 | Beardsley et al. |
| 8,967,447 B2 | 3/2015 | Hartoumbekis |
| 8,968,276 B2 | 3/2015 | Zemlok et al. |
| 8,973,803 B2 | 3/2015 | Hall et al. |
| 8,979,827 B2 | 3/2015 | Cappola |
| 9,004,340 B2 | 4/2015 | Scirica |
| 9,010,611 B2 | 4/2015 | Ross et al. |
| 9,016,541 B2 | 4/2015 | Viola et al. |
| 9,016,545 B2 | 4/2015 | Aranyi et al. |
| 9,022,271 B2 | 5/2015 | Scirica |
| 9,023,014 B2 | 5/2015 | Chowaniec et al. |
| 9,027,817 B2 | 5/2015 | Milliman et al. |
| 9,027,818 B2 | 5/2015 | Scirica et al. |
| 9,033,202 B2 | 5/2015 | Scirica |
| 9,038,880 B1 | 5/2015 | Donohoe |
| 9,055,943 B2 | 6/2015 | Zemlok et al. |
| 9,072,515 B2 | 7/2015 | Hall et al. |
| 9,084,601 B2 | 7/2015 | Moore et al. |
| 9,101,358 B2 | 8/2015 | Kerr et al. |
| 9,161,813 B2 | 10/2015 | Benamou |
| 9,204,876 B2 | 12/2015 | Cappola et al. |
| 9,237,890 B2 | 1/2016 | Kostrzewski |
| 9,265,585 B2 | 2/2016 | Wingardner et al. |
| 9,282,966 B2 | 3/2016 | Shelton, IV et al. |
| 9,386,984 B2 | 7/2016 | Aronhalt et al. |
| 9,402,629 B2 | 8/2016 | Ehrenfels et al. |
| 9,510,830 B2 | 12/2016 | Shelton, IV et al. |
| 9,532,782 B2 | 1/2017 | Kostrzewski |
| 9,662,108 B2 | 5/2017 | Williams |
| 9,737,302 B2 | 8/2017 | Shelton, IV et al. |
| 9,737,303 B2 | 8/2017 | Shelton, IV et al. |
| 9,797,486 B2 | 10/2017 | Zergiebel et al. |
| 2002/0025243 A1 | 2/2002 | Heck |
| 2002/0029044 A1 | 3/2002 | Monassevitch et al. |
| 2002/0062136 A1 | 5/2002 | Hillstead |
| 2002/0120279 A1 | 8/2002 | Deguillebon et al. |
| 2003/0130677 A1 | 7/2003 | Whitman et al. |
| 2004/0006372 A1 | 1/2004 | Racenet et al. |
| 2004/0138705 A1 | 7/2004 | Heino et al. |
| 2005/0139629 A1* | 6/2005 | Schwemberger .... A61B 17/072 227/19 |
| 2005/0234478 A1 | 10/2005 | Wixey |
| 2006/0097026 A1 | 5/2006 | Shelton, IV |
| 2006/0100644 A1 | 5/2006 | Viola |
| 2006/0180634 A1 | 8/2006 | Shelton, IV et al. |

(56) References Cited

U.S. PATENT DOCUMENTS

| | | |
|---|---|---|
| 2006/0235442 A1 | 10/2006 | Huitema |
| 2006/0289602 A1 | 12/2006 | Wales et al. |
| 2007/0034664 A1 | 2/2007 | Jiang |
| 2007/0039997 A1 | 2/2007 | Mather et al. |
| 2007/0057014 A1 | 3/2007 | Whitman et al. |
| 2007/0068990 A1 | 3/2007 | Shelton, IV et al. |
| 2007/0084897 A1 | 4/2007 | Shelton, IV et al. |
| 2007/0102472 A1 | 5/2007 | Shelton, IV |
| 2007/0119901 A1 | 5/2007 | Ehrenfels et al. |
| 2007/0131732 A1 | 6/2007 | Holsten et al. |
| 2007/0175950 A1 | 8/2007 | Shelton, IV et al. |
| 2007/0175951 A1 | 8/2007 | Shelton, IV et al. |
| 2008/0029574 A1 | 2/2008 | Shelton et al. |
| 2008/0029575 A1 | 2/2008 | Shelton et al. |
| 2008/0041918 A1 | 2/2008 | Holsten et al. |
| 2008/0078807 A1 | 4/2008 | Hess et al. |
| 2008/0083807 A1 | 4/2008 | Beardsley et al. |
| 2008/0169333 A1 | 7/2008 | Shelton et al. |
| 2008/0179375 A1 | 7/2008 | Scirica |
| 2008/0255607 A1 | 10/2008 | Zemlok |
| 2009/0001129 A1 | 1/2009 | Marczyk |
| 2009/0001130 A1 | 1/2009 | Hess et al. |
| 2009/0026245 A1 | 1/2009 | Holsten et al. |
| 2009/0048589 A1 | 2/2009 | Takashino et al. |
| 2009/0057369 A1 | 3/2009 | Smith et al. |
| 2009/0090763 A1 | 4/2009 | Zemlok et al. |
| 2009/0198272 A1 | 8/2009 | Kerver et al. |
| 2009/0206131 A1 | 8/2009 | Weisenburgh, II et al. |
| 2009/0206133 A1 | 8/2009 | Morgan et al. |
| 2009/0206137 A1 | 8/2009 | Hall et al. |
| 2009/0277948 A1 | 11/2009 | Beardsley et al. |
| 2009/0277949 A1 | 11/2009 | Viola et al. |
| 2010/0069942 A1 | 3/2010 | Shelton, IV |
| 2010/0072258 A1 | 3/2010 | Farascioni et al. |
| 2010/0089970 A1 | 4/2010 | Smith et al. |
| 2010/0193566 A1 | 8/2010 | Scheib et al. |
| 2010/0230465 A1 | 9/2010 | Smith et al. |
| 2010/0331820 A1 | 12/2010 | Prisco et al. |
| 2011/0036892 A1 | 2/2011 | Marczyk et al. |
| 2011/0042440 A1 | 2/2011 | Holsten et al. |
| 2011/0087276 A1 | 4/2011 | Bedi et al. |
| 2011/0108601 A1 | 5/2011 | Clark et al. |
| 2011/0108603 A1 | 5/2011 | Racenet et al. |
| 2011/0121049 A1 | 5/2011 | Malinouskas et al. |
| 2011/0125138 A1 | 5/2011 | Malinouskas et al. |
| 2011/0127185 A1 | 6/2011 | Ward |
| 2011/0139852 A1 | 6/2011 | Zingman |
| 2011/0147433 A1 | 6/2011 | Shelton, IV et al. |
| 2011/0155787 A1 | 6/2011 | Laurent et al. |
| 2011/0290853 A1 | 12/2011 | Shelton, IV et al. |
| 2012/0061446 A1 | 3/2012 | Knodel et al. |
| 2012/0074198 A1 | 3/2012 | Huitema et al. |
| 2012/0074200 A1 | 3/2012 | Schmid et al. |
| 2012/0078243 A1 | 3/2012 | Worrell et al. |
| 2012/0080482 A1 | 4/2012 | Schall et al. |
| 2012/0080498 A1 | 4/2012 | Shelton, IV et al. |
| 2012/0091182 A1 | 4/2012 | Marczyk |
| 2012/0168487 A1 | 7/2012 | Holsten et al. |
| 2012/0193396 A1 | 8/2012 | Zemlok et al. |
| 2012/0211542 A1 | 8/2012 | Racenet |
| 2012/0286022 A1 | 11/2012 | Olson et al. |
| 2012/0318844 A1 | 12/2012 | Shelton, IV et al. |
| 2012/0325893 A1 | 12/2012 | Pastorelli et al. |
| 2013/0001270 A1 | 1/2013 | Kostrzewski |
| 2013/0012958 A1 | 1/2013 | Marczyk et al. |
| 2013/0015229 A1 | 1/2013 | Viola |
| 2013/0015230 A1 | 1/2013 | Wixey et al. |
| 2013/0015232 A1 | 1/2013 | Smith et al. |
| 2013/0015233 A1 | 1/2013 | Viola |
| 2013/0020375 A1 | 1/2013 | Shelton, IV et al. |
| 2013/0037595 A1 | 2/2013 | Gupta et al. |
| 2013/0048697 A1 | 2/2013 | Shelton, IV et al. |
| 2013/0056521 A1 | 3/2013 | Swensgard |
| 2013/0079814 A1 | 3/2013 | Hess et al. |
| 2013/0087603 A1 | 4/2013 | Viola |
| 2013/0092717 A1 | 4/2013 | Marczyk et al. |
| 2013/0098964 A1 | 4/2013 | Smith et al. |
| 2013/0098965 A1 | 4/2013 | Kostrzewski et al. |
| 2013/0098969 A1 | 4/2013 | Scirica et al. |
| 2013/0105545 A1 | 5/2013 | Burbank |
| 2013/0105547 A1 | 5/2013 | Beardsley |
| 2013/0105548 A1 | 5/2013 | Hodgkinson et al. |
| 2013/0105549 A1 | 5/2013 | Holsten et al. |
| 2013/0112730 A1 | 5/2013 | Whitman et al. |
| 2013/0112731 A1 | 5/2013 | Hodgkinson |
| 2013/0126583 A1 | 5/2013 | Hueil et al. |
| 2013/0126586 A1 | 5/2013 | Zhang et al. |
| 2013/0146640 A1 | 6/2013 | Jankowski |
| 2013/0172928 A1 | 7/2013 | Kostrzewski |
| 2013/0172929 A1 | 7/2013 | Hess et al. |
| 2013/0175317 A1 | 7/2013 | Yates et al. |
| 2013/0175322 A1 | 7/2013 | Yates et al. |
| 2013/0184718 A1 | 7/2013 | Smith et al. |
| 2013/0186931 A1 | 7/2013 | Beardsley |
| 2013/0186932 A1 | 7/2013 | Shelton, IV et al. |
| 2013/0186933 A1 | 7/2013 | Shelton, IV et al. |
| 2013/0193188 A1 | 8/2013 | Shelton, IV et al. |
| 2013/0200132 A1 | 8/2013 | Moore et al. |
| 2013/0206816 A1 | 8/2013 | Penna |
| 2013/0214025 A1 | 8/2013 | Zemlok et al. |
| 2013/0221065 A1 | 8/2013 | Aronhalt et al. |
| 2013/0240604 A1 | 9/2013 | Knodel |
| 2013/0248582 A1 | 9/2013 | Scirica |
| 2013/0256370 A1 | 10/2013 | Smith et al. |
| 2013/0256371 A1 | 10/2013 | Shelton, IV |
| 2013/0270321 A1 | 10/2013 | Marczyk |
| 2013/0270323 A1 | 10/2013 | Marczyk |
| 2013/0284789 A1 | 10/2013 | Smith et al. |
| 2013/0284791 A1 | 10/2013 | Olson et al. |
| 2013/0299552 A1 | 11/2013 | Viola |
| 2013/0306702 A1 | 11/2013 | Viola et al. |
| 2013/0306703 A1 | 11/2013 | Ehrenfels et al. |
| 2013/0306706 A1 | 11/2013 | Knodel |
| 2013/0313303 A1 | 11/2013 | Shelton, IV et al. |
| 2013/0032781 A1 | 12/2013 | Swayze et al. |
| 2013/0327809 A1 | 12/2013 | Shelton, IV et al. |
| 2013/0334278 A1 | 12/2013 | Kerr et al. |
| 2013/0334280 A1 | 12/2013 | Krehel et al. |
| 2013/0334281 A1 | 12/2013 | Williams |
| 2013/0334283 A1 | 12/2013 | Swayze et al. |
| 2013/0334284 A1 | 12/2013 | Swayze et al. |
| 2013/0334285 A1 | 12/2013 | Swayze et al. |
| 2013/0334286 A1 | 12/2013 | Swayze et al. |
| 2013/0334287 A1 | 12/2013 | Shelton, IV |
| 2013/0334288 A1 | 12/2013 | Shelton, IV |
| 2014/0014704 A1 | 1/2014 | Onukuri et al. |
| 2014/0014707 A1 | 1/2014 | Onukuri et al. |
| 2014/0021239 A1 | 1/2014 | Kostrzewski |
| 2014/0025046 A1 | 1/2014 | Williams et al. |
| 2014/0027491 A1 | 1/2014 | Beardsley et al. |
| 2014/0027493 A1 | 1/2014 | Jankowski |
| 2014/0042204 A1 | 2/2014 | Beetel |
| 2014/0103092 A1 | 4/2014 | Kostrzewski et al. |
| 2014/0103093 A1 | 4/2014 | Koch, Jr. et al. |
| 2014/0107640 A1 | 4/2014 | Yates et al. |
| 2014/0110453 A1 | 4/2014 | Wingardner et al. |
| 2014/0131416 A1 | 5/2014 | Whitman et al. |
| 2014/0135832 A1 | 5/2014 | Park et al. |
| 2014/0151433 A1 | 6/2014 | Shelton, IV et al. |
| 2014/0151434 A1 | 6/2014 | Shelton, IV et al. |
| 2014/0158746 A1 | 6/2014 | Mastri et al. |
| 2014/0166727 A1 | 6/2014 | Swayze et al. |
| 2014/0175146 A1 | 6/2014 | Knodel |
| 2014/0175149 A1 | 6/2014 | Smith et al. |
| 2014/0203063 A1 | 7/2014 | Hessler et al. |
| 2014/0205637 A1 | 7/2014 | Widenhouse et al. |
| 2014/0224856 A1 | 8/2014 | Smith et al. |
| 2014/0236173 A1 | 8/2014 | Scirica et al. |
| 2014/0236184 A1 | 8/2014 | Leimbach |
| 2014/0239038 A1 | 8/2014 | Leimbach et al. |
| 2014/0239041 A1 | 8/2014 | Zerkle et al. |
| 2014/0239044 A1 | 8/2014 | Hoffman |
| 2014/0246474 A1 | 9/2014 | Hall et al. |
| 2014/0246475 A1 | 9/2014 | Hall et al. |

(56) References Cited

U.S. PATENT DOCUMENTS

| | | |
|---|---|---|
| 2014/0246478 A1 | 9/2014 | Baber et al. |
| 2014/0246479 A1 | 9/2014 | Baber et al. |
| 2014/0260746 A1 | 9/2014 | Sakaguchi et al. |
| 2014/0263537 A1 | 9/2014 | Leimbach et al. |
| 2014/0263539 A1 | 9/2014 | Leimbach et al. |
| 2014/0263541 A1 | 9/2014 | Leimbach et al. |
| 2014/0263542 A1 | 9/2014 | Leimbach et al. |
| 2014/0263543 A1 | 9/2014 | Leimbach et al. |
| 2014/0263545 A1 | 9/2014 | Williams et al. |
| 2014/0263546 A1 | 9/2014 | Aranyi |
| 2014/0263550 A1 | 9/2014 | Aranyi et al. |
| 2014/0263553 A1 | 9/2014 | Leimbach et al. |
| 2014/0263554 A1 | 9/2014 | Leimbach et al. |
| 2014/0263555 A1 | 9/2014 | Hufnagel et al. |
| 2014/0263559 A1 | 9/2014 | Williams et al. |
| 2014/0263562 A1 | 9/2014 | Patel et al. |
| 2014/0263564 A1 | 9/2014 | Leimbach et al. |
| 2014/0263565 A1 | 9/2014 | Lytle, IV et al. |
| 2014/0263566 A1 | 9/2014 | Williams et al. |
| 2014/0263567 A1 | 9/2014 | Williams et al. |
| 2014/0263568 A1 | 9/2014 | Williams et al. |
| 2014/0263569 A1 | 9/2014 | Williams et al. |
| 2014/0263570 A1 | 9/2014 | Hopkins et al. |
| 2014/0263571 A1 | 9/2014 | Morgan et al. |
| 2014/0263572 A1 | 9/2014 | Shelton, IV et al. |
| 2014/0284372 A1 | 9/2014 | Kostrzewski |
| 2014/0291378 A1 | 10/2014 | Shelton, IV et al. |
| 2014/0299649 A1 | 10/2014 | Shelton, IV et al. |
| 2014/0305986 A1 | 10/2014 | Hall et al. |
| 2014/0305988 A1 | 10/2014 | Boudreaux et al. |
| 2014/0305992 A1 | 10/2014 | Kimsey et al. |
| 2014/0305994 A1 | 10/2014 | Parihar et al. |
| 2014/0353359 A1 | 12/2014 | Hall et al. |
| 2015/0008248 A1 | 1/2015 | Giordano et al. |
| 2015/0034697 A1 | 2/2015 | Mastri et al. |
| 2015/0041518 A1 | 2/2015 | Shelton, IV et al. |
| 2015/0053738 A1 | 2/2015 | Morgan et al. |
| 2015/0053740 A1 | 2/2015 | Shelton, IV |
| 2015/0053741 A1 | 2/2015 | Shelton, IV et al. |
| 2015/0053742 A1 | 2/2015 | Shelton, IV et al. |
| 2015/0053743 A1 | 2/2015 | Yates et al. |
| 2015/0053744 A1 | 2/2015 | Swayze et al. |
| 2015/0053745 A1 | 2/2015 | Yates et al. |
| 2015/0053746 A1 | 2/2015 | Shelton, IV et al. |
| 2015/0053748 A1 | 2/2015 | Yates et al. |
| 2015/0053749 A1 | 2/2015 | Shelton, IV et al. |
| 2015/0054753 A1 | 2/2015 | Morgan et al. |
| 2015/0007621 A1 | 3/2015 | Shelton, IV et al. |
| 2015/0060516 A1 | 3/2015 | Collings et al. |
| 2015/0060517 A1 | 3/2015 | Williams |
| 2015/0060521 A1 | 3/2015 | Weisenburgh, II et al. |
| 2015/0076205 A1 | 3/2015 | Zergiebel |
| 2015/0076206 A1 | 3/2015 | Sapre |
| 2015/0076209 A1 | 3/2015 | Shelton, IV et al. |
| 2015/0076212 A1 | 3/2015 | Shelton, IV |
| 2015/0083781 A1 | 3/2015 | Giordano et al. |
| 2015/0083783 A1 | 3/2015 | Shelton, IV et al. |
| 2015/0090760 A1 | 4/2015 | Giordano et al. |
| 2015/0090761 A1 | 4/2015 | Giordano et al. |
| 2015/0090762 A1 | 4/2015 | Giordano et al. |
| 2015/0090764 A1 | 4/2015 | Zemlok et al. |
| 2015/0108201 A1 | 4/2015 | Williams |
| 2015/0122872 A1 | 5/2015 | Olson et al. |
| 2015/0127046 A1 | 5/2015 | Peterson |
| 2015/0129631 A1 | 5/2015 | Beetel |
| 2015/0129634 A1 | 5/2015 | Shelton, IV et al. |
| 2015/0133995 A1 | 5/2015 | Shelton, IV et al. |
| 2015/0133996 A1 | 5/2015 | Shelton, IV et al. |
| 2015/0134076 A1 | 5/2015 | Shelton, IV et al. |
| 2015/0144678 A1 | 5/2015 | Hall et al. |
| 2015/0201935 A1 | 7/2015 | Weisenburgh, II et al. |
| 2015/0208902 A1 | 7/2015 | Okamoto |
| 2015/0245834 A1 | 9/2015 | Scirica et al. |
| 2015/0272576 A1 | 10/2015 | Cappola |
| 2015/0289873 A1 | 10/2015 | Shelton, IV et al. |
| 2015/0297221 A1 | 10/2015 | Kerr et al. |
| 2015/0297233 A1 | 10/2015 | Huitema et al. |
| 2016/0000439 A1 | 1/2016 | Weisenburgh, II et al. |
| 2016/0000440 A1 | 1/2016 | Weisenburgh, II et al. |
| 2016/0058447 A1 | 3/2016 | Posada et al. |
| 2016/0058492 A1 | 3/2016 | Yates et al. |
| 2016/0183948 A1 | 6/2016 | Shelton, IV et al. |
| 2016/0310204 A1 | 10/2016 | McHenry et al. |
| 2016/0338702 A1 | 11/2016 | Ehrenfels et al. |
| 2016/0374672 A1 | 12/2016 | Bear et al. |
| 2016/0374675 A1 | 12/2016 | Shelton, IV et al. |
| 2017/0007241 A1 | 1/2017 | Shelton, IV et al. |
| 2017/0007242 A1 | 1/2017 | Shelton, IV et al. |
| 2017/0007243 A1 | 1/2017 | Shelton, IV et al. |
| 2017/0007249 A1 | 1/2017 | Shelton, IV et al. |
| 2017/0231633 A1 | 8/2017 | Marczyk et al. |
| 2017/0245856 A1 | 8/2017 | Baxter, III et al. |
| 2017/0245858 A1 | 8/2017 | Williams |
| 2017/0281161 A1 | 10/2017 | Shelton, IV et al. |
| 2017/0281165 A1 | 10/2017 | Harris et al. |
| 2017/0281168 A1 | 10/2017 | Shelton, IV et al. |
| 2017/0290583 A1 | 10/2017 | Reed et al. |
| 2017/0290584 A1 | 10/2017 | Jasemian et al. |

FOREIGN PATENT DOCUMENTS

| | | |
|---|---|---|
| EP | 514139 | 11/1992 |
| EP | 536903 | 4/1993 |
| EP | 596543 | 5/1994 |
| EP | 1 523 944 A1 | 4/2005 |
| EP | 1 759 812 A1 | 3/2007 |
| EP | 1 915 953 A1 | 4/2008 |
| EP | 1 479 348 B1 | 7/2008 |
| EP | 2 005 902 A2 | 12/2008 |
| EP | 2 090 241 A1 | 8/2009 |
| EP | 2 263 568 A2 | 12/2010 |
| EP | 2 361 562 A1 | 8/2011 |
| EP | 2 462 875 A2 | 6/2012 |
| EP | 2 486 859 A2 | 8/2012 |
| EP | 2 764 833 A2 | 8/2014 |
| EP | 2 772 192 A1 | 9/2014 |
| EP | 2 777 530 A1 | 9/2014 |
| EP | 2 923 661 A2 | 3/2015 |
| EP | 2 891 462 A1 | 7/2015 |
| EP | 2 926 742 A1 | 10/2015 |
| EP | 2 942 020 A2 | 11/2015 |
| EP | 3 135 225 A2 | 3/2017 |
| EP | 3 238 639 A2 | 3/2017 |
| EP | 3 338 653 A1 | 6/2018 |
| EP | 3 338 698 A1 | 6/2018 |
| EP | 3 338 702 A1 | 6/2018 |
| JP | 2001-087272 A | 4/2001 |
| RU | 2063710 | 7/1996 |
| WO | WO 83/02247 | 7/1983 |
| WO | WO 94/24947 A1 | 11/1994 |
| WO | WO 02/30296 | 4/2002 |
| WO | WO 02/096327 A2 | 12/2002 |
| WO | WO 2003/094747 A1 | 11/2003 |
| WO | WO 2004/032762 A1 | 4/2004 |
| WO | WO 2012/052729 A1 | 4/2012 |
| WO | WO 2014/139440 A1 | 9/2014 |

OTHER PUBLICATIONS

European Patent Office, Extended European Search Report for European Application No. EP 20157713.7, entitled "Surgical Stapler with Expandable Jaw," dated May 11, 2020, 6 pgs.

International Searching Authority/ EPO, Invitation to Pay Additional Fees for PCTUS2020/025496, entitled "Reload Cover for Surgical Stapling System," dated Jun. 18, 2019, 15 pgs.

European Patent Office, Extended European Search Report for European Application No. EP 20161294.2, entitled "Surgical Stapler with Self-Adjusting Staple Height," dated Jun. 22, 2020, 6 pgs.

European Patent Office, Extended European Search Report for European Application No. EP 20197859.0, entitled "Surgical Stapler with Circumferential Firing," dated Jan. 28, 2021, 13 pgs.

European Patent Office, The International Search Report and the Written Opinion of the International Searching Authority for Inter-

(56) References Cited

OTHER PUBLICATIONS national Application No. PCT/US2020/025496, entitled "Reload Cover for Surgical Stapling System," dated Aug. 13, 2020, 20 pgs.
The International Bureau of WIPO, International Preliminary Report on Patentability, for International Application No. PCT/US2019/019867, entitled "Surgical Stapler Having a Powered Handle," dated Sep. 3, 2020, 16 pgs.
Ethicon Endo Surgery, Inc., Contour Curved Cutter Stapler, 2014, 2 pgs.
Justright Surgical, JustRight Surgery, Dec. 31, 2014, 2 pgs.
European Patent Office, The International Search Report and the Written Opinion of the International Searching Authority for International Application No. PCT/US2014/028811, entitled "Surgical Stapler Having Actuation Mechanism with Rotatable Shaft," dated Aug. 5, 2014, 14 pgs.
European Patent Office, International Search Report and Written Opinion for International Application No. PCT/US2014/028211, entitled "Surgical Stapler with Partial Pockets," dated Sep. 8, 2014, 17 pgs.
International Searching Authority, U.S., The International Search Report and the Written Opinion of the International Searching authority for international application PCT/US2014/027768, titled "Surgical Stapler with Expandable Jaw", dated Jul. 25, 2014, 17 pgs.
The International Bureau of WIPO, International Preliminary Report on Patentability, for International Application No. PCT/US2014/028811, entitled "Surgical Stapler Having Actuation Mechanism with Rotatable Shaft," dated Sep. 15, 2015, 11 pgs.
International Searching Authority, U.S., The International Search Report and the Written Opinion of the International Searching authority for international application PCT/US2015/0035379, titled "Surgical Stapler with Circumferential Firing", dated Sep. 15, 2015, 22 pgs.
The International Bureau of Wipo, International Preliminary Report on Patentability, for International Application No. PCT/US2014/027768, entitled "Surgical Stapler with Expandable Jaw," dated Sep. 24, 2015, 9 pgs.
European Patent Office, International Search Report and Written Opinion for International Application No. PCT/US2015/050103 titled "Surgical Stapler with Self-Adjusting Staple Height" dated Feb. 17, 2016, 18 pgs.
The International Bureau of WIPO, International Preliminary Report on Patentability for International Application No. PCT/US2015/035379, entitled "Surgical Stapler with Circumferential Firing," dated Dec. 22, 2016, 14 pgs.
The International Bureau of WIPO, International Preliminary Report on Patentability for International Application No. PCT/US2015/050103, titled "Surgical Stapler With Self-Adjusting Staple Height," dated Mar. 30, 2017, 12 pgs.
European Patent Office, European Search Report for European Application No. EP 14764812.5, entitled "Surgical Stapler Having Actuation Mechanism with Rotatable Shaft," dated Apr. 6, 2017, 6 pgs.
International Searching Authority/ Epo, Invitation to Pay Additional Fees and Communication Relating to the Results of the Partial International Search for PCT/US2017/027269, entitled "Reload Shaft Assembly for Surgical Stapler," dated Jun. 28, 2017, 15 pgs.
International Searching Authority/ Epo, Invitation to Pay Additional Fees and Communication Relating to the Results of the Partial International Search for PCT/US2017/027213, entitled "Surgical Stapler Having a Powered Handle," dated Jul. 5, 2017, 11 pgs.
International Searching Authority/ Epo, Invitation to Pay Additional Fees and Communication Relating to the Results of the Partial International Search for PCT/US2017/027142, entitled "Surgical Stapler Having Articulation Mechanism," dated Jul. 10, 2017, 15 pgs.
European Patent Office, The International Search Report and the Written Opinion of the International Searching Authority for International Application No. PCT/US2017/027269, entitled "Reload Shaft Assembly for Surgical Stapler," dated Sep. 12, 2017, 22 pgs.
European Patent Office, The International Search Report and the Written Opinion of the International Searching Authority for International Application No. PCT/US2017/027213, entitled "Surgical Stapler Having a Powered Handle," dated Sep. 13, 2017, 17 pgs.
European Patent Office, The International Search Report and the Written Opinion of the International Searching Authority for International Application No. PCT/US2017/027142, entitled "Surgical Stapler Having Articulation Mechanism," dated Sep. 14, 2017, 21 pgs.
European Patent Office, The International Search Report and Written Opinion of the International Searching Authority for International Application No. PCT/US2016/045993 titled "Surgical Stapler Having Locking Articulation Joint", dated Jan. 24, 2017, 20 pgs.
European Patent Office, Partial European Search Report for European Application No. EP 14762896.0, entitled "Surgical Stapler with Expandable Jaw," dated Apr. 10, 2017, 6 pgs.
The International Bureau of WIPO, International Preliminary Report on Patentability, for International Application No. PCT/US2016/045993, entitled "Surgical Stapler Having Locking Articulation Joint," dated Feb. 15, 2018, 13 pgs.
European Patent Office, Extended European Search Report for European Application No. EP 18186558.5, entitled "Surgical Stapler with Partial Pockets," dated Oct. 10, 2018, 9 pgs.
The International Bureau of WIPO, International Preliminary Report on Patentability, for International Application No. PCT/US2017/027142, entitled "Surgical Stapler Having Articulation Mechanism," dated Oct. 25, 2018, 12 pgs.
The International Bureau of WIPO, International Preliminary Report on Patentability, for International Application No. PCT/US2017/027213, entitled "Surgical Stapler Having Powered Handle," dated Oct. 25, 2018, 9 pgs.
The International Bureau of WIPO, International Preliminary Report on Patentability, for International Application No. PCT/US2017/027269, entitled "Reload Shaft Assembly for Surgical Stapler," dated Oct. 25, 2018, 12 pgs.
European Patent Office, Extended European Search Report for European Application No. EP 18189960.0, entitled "Surgical Stapler with Expandable Jaw," dated Dec. 13, 2018, 6 pgs.
International Searching Authority/ EPO, Invitation to Pay Additional Fees and Communication Relating to the Results of the Partial International Search for PCT/US2019/019867, entitled "Surgical Stapler Having a Powered Handle," dated May 24, 2019, 19 pgs.
European Patent Office, The International Search Report and the Written Opinion of the International Searching Authority for International Application No. PCT/US2019/019867, entitled "Surgical Stapler Having a Powered Handle," dated Jul. 19, 2019, 24 pgs.
European Patent Office, Extended European Search Report for European Application No. EP 19150575.9, entitled "Surgical Stapler Having Actuation Mechanism with Rotatable Shaft," dated Aug. 21, 2019, 5 pgs.
European Patent Office, Extended European Search Report for European Application No. EP 19180055.6, entitled "Surgical Stapler with Circumferential Firing," dated Sep. 20, 2019, 8 pgs.
U.S. Appl. No. 11/805,094, filed May 21, 2007, entitled "Surgical Stapler With Firing Lock Mechanism" and associated file history.
U.S. Appl. No. 12/495,384, filed Jun. 30, 2009, entitled "Surgical Stapler With Firing Lock Mechanism" and associated file history.
U.S. Appl. No. 12/796,503, filed Jun. 8, 2010, entitled "Surgical Stapler With Firing Lock Mechanism" and associated file history.
European Patent Office, European Search Report for European Application No. 07784007.2, entitled "Surgical Stapler", dated Jun. 15, 2012.
European Patent Office, The International Search Report and Written Opinion for International Application No. PCT/US2020/067540, dated May 3, 2021, entitled "Electrosurgical System with Tissue and Maximum Current Identification," 12 pages.
European Patent Office, Extended European Search Report for European Application No. EP 21162419.2, entitled "Surgical Stapler Having Articulation Mechanism," dated Jun. 22, 2021, 10 pgs.
The International Bureau of WIPO, International Preliminary Report on Patentability, for International Application No. PCT/US2020/

(56) References Cited

OTHER PUBLICATIONS 019938, entitled "Surgical Stapler Having a Two-Position Lockout Mechanism," dated Sep. 10, 2020, 10 pgs.

* cited by examiner

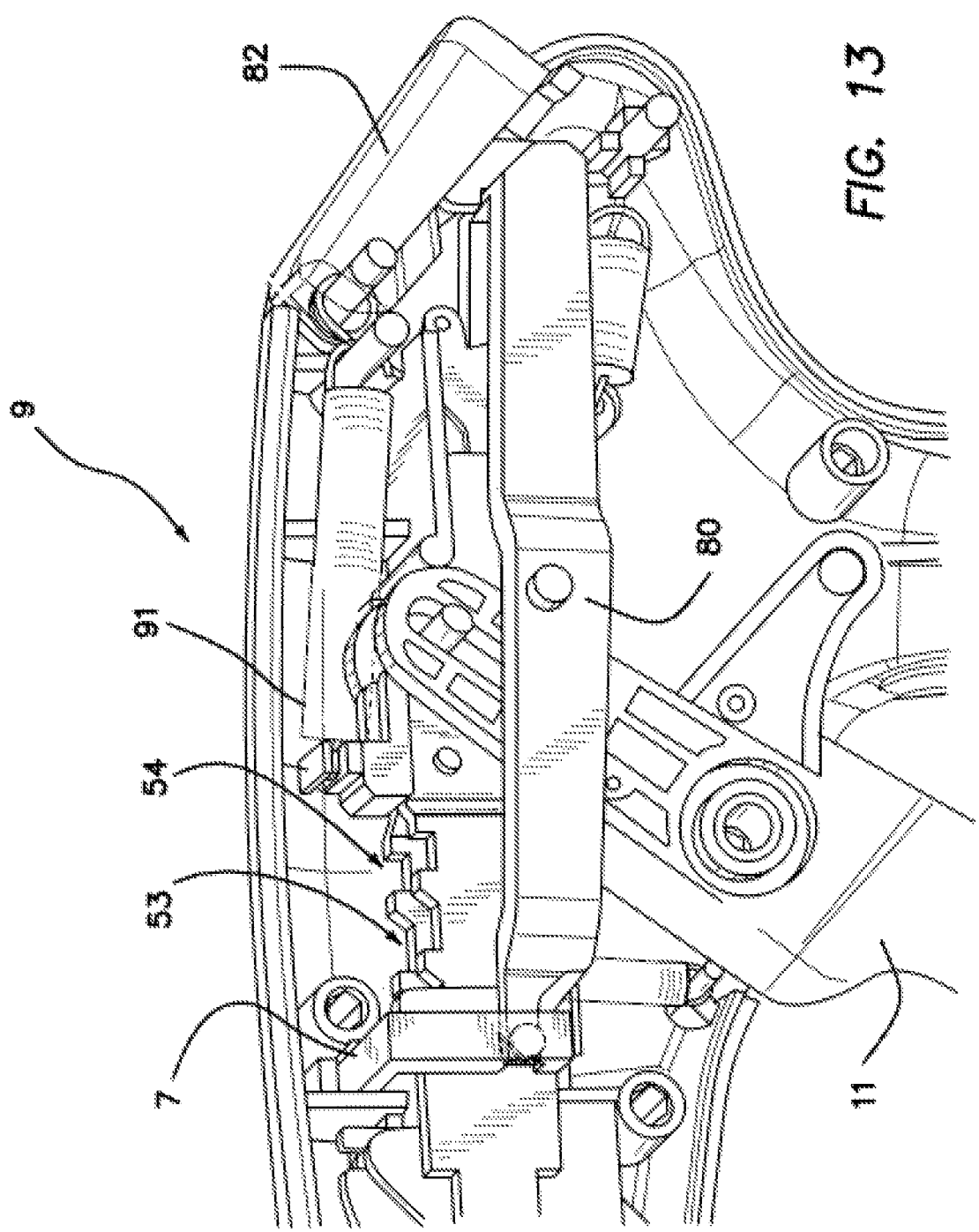

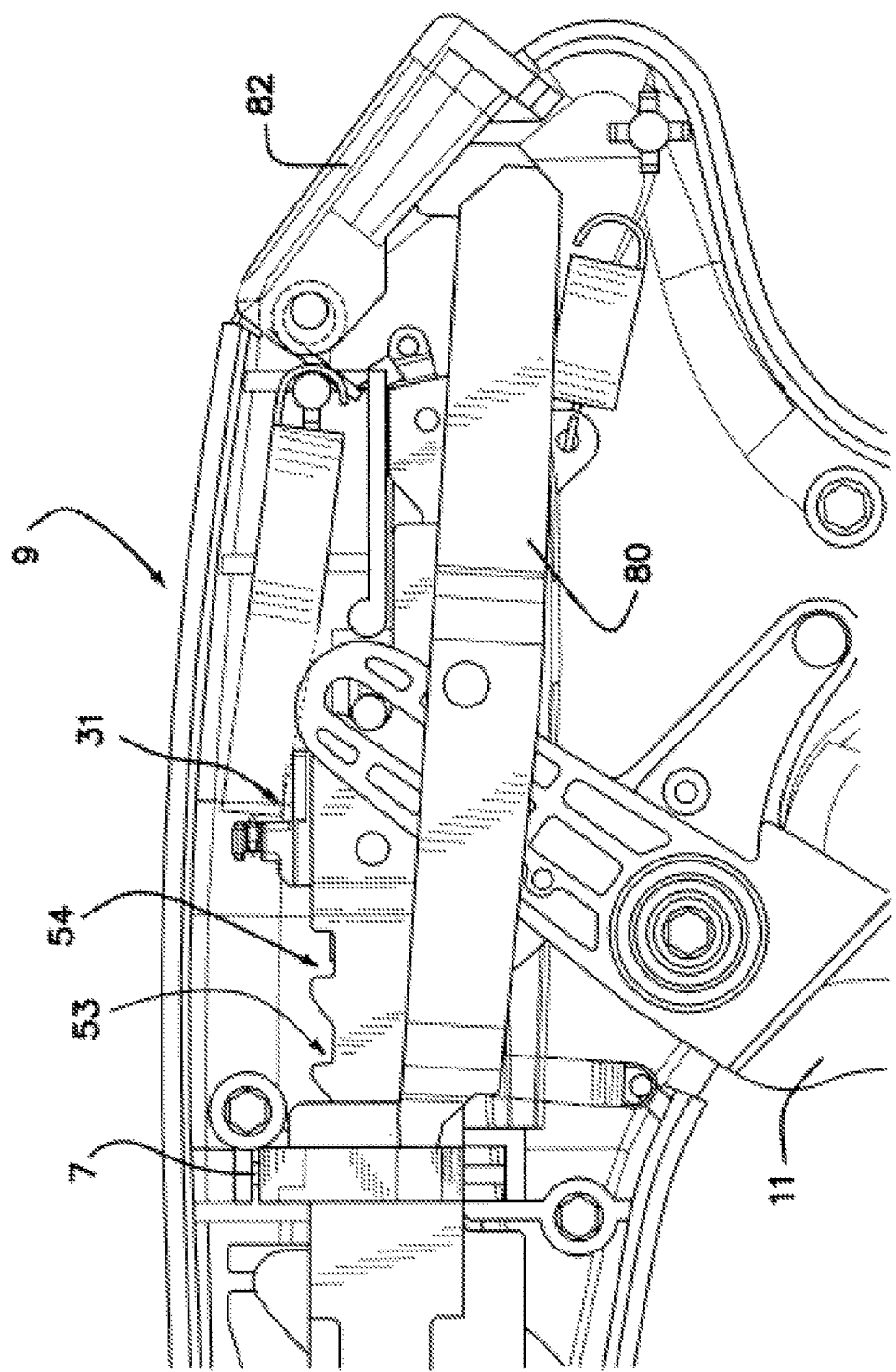

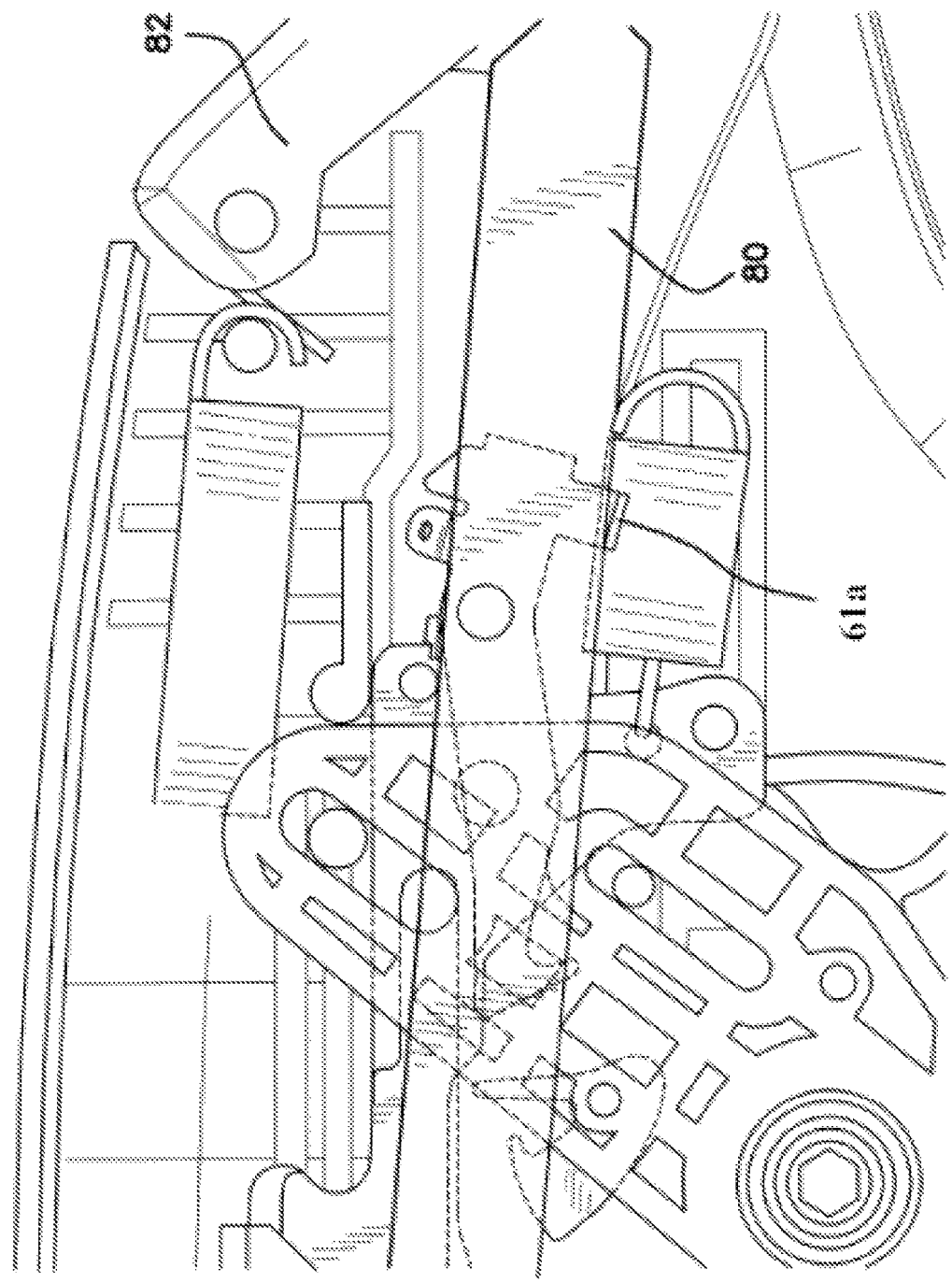

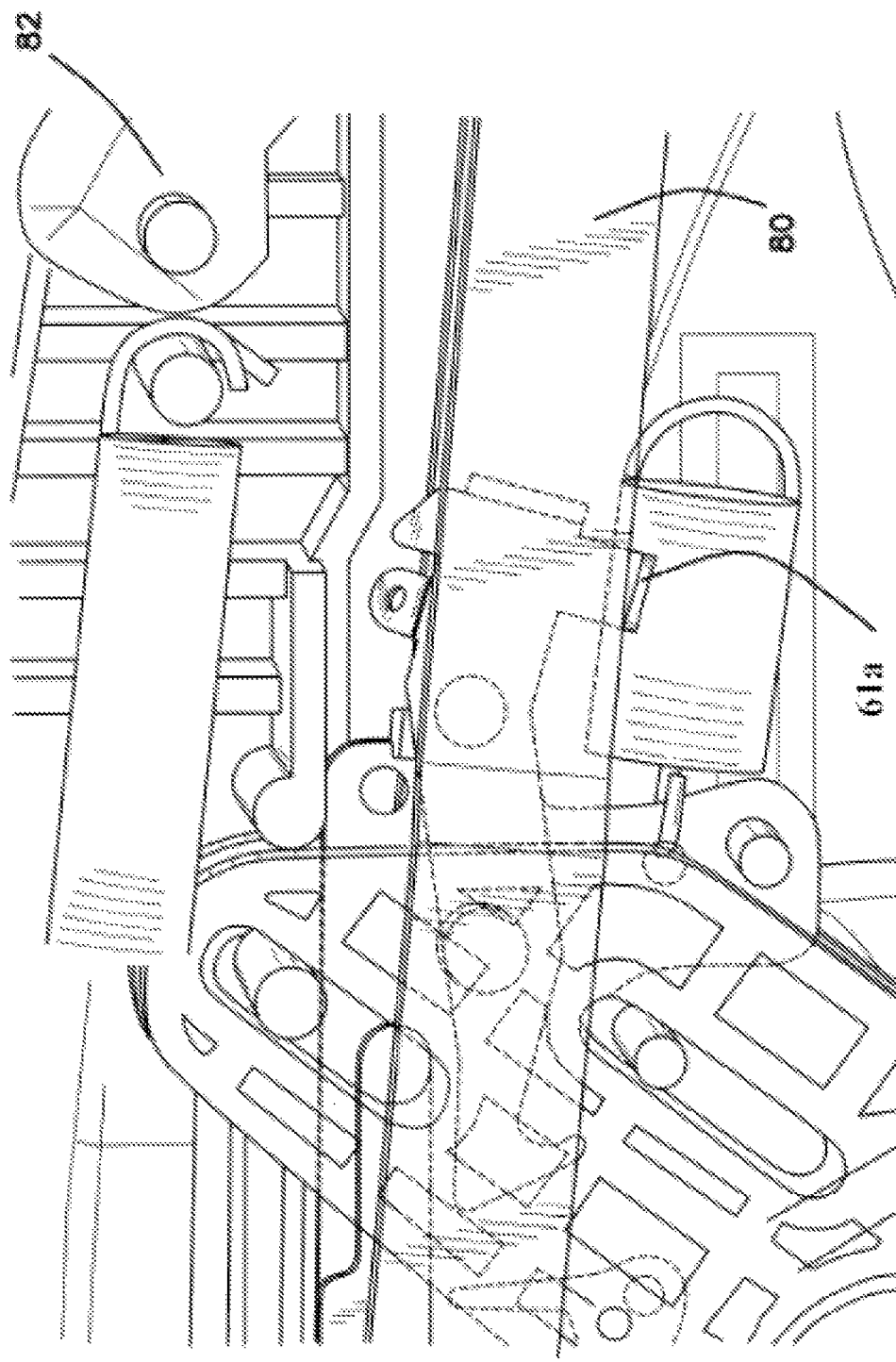

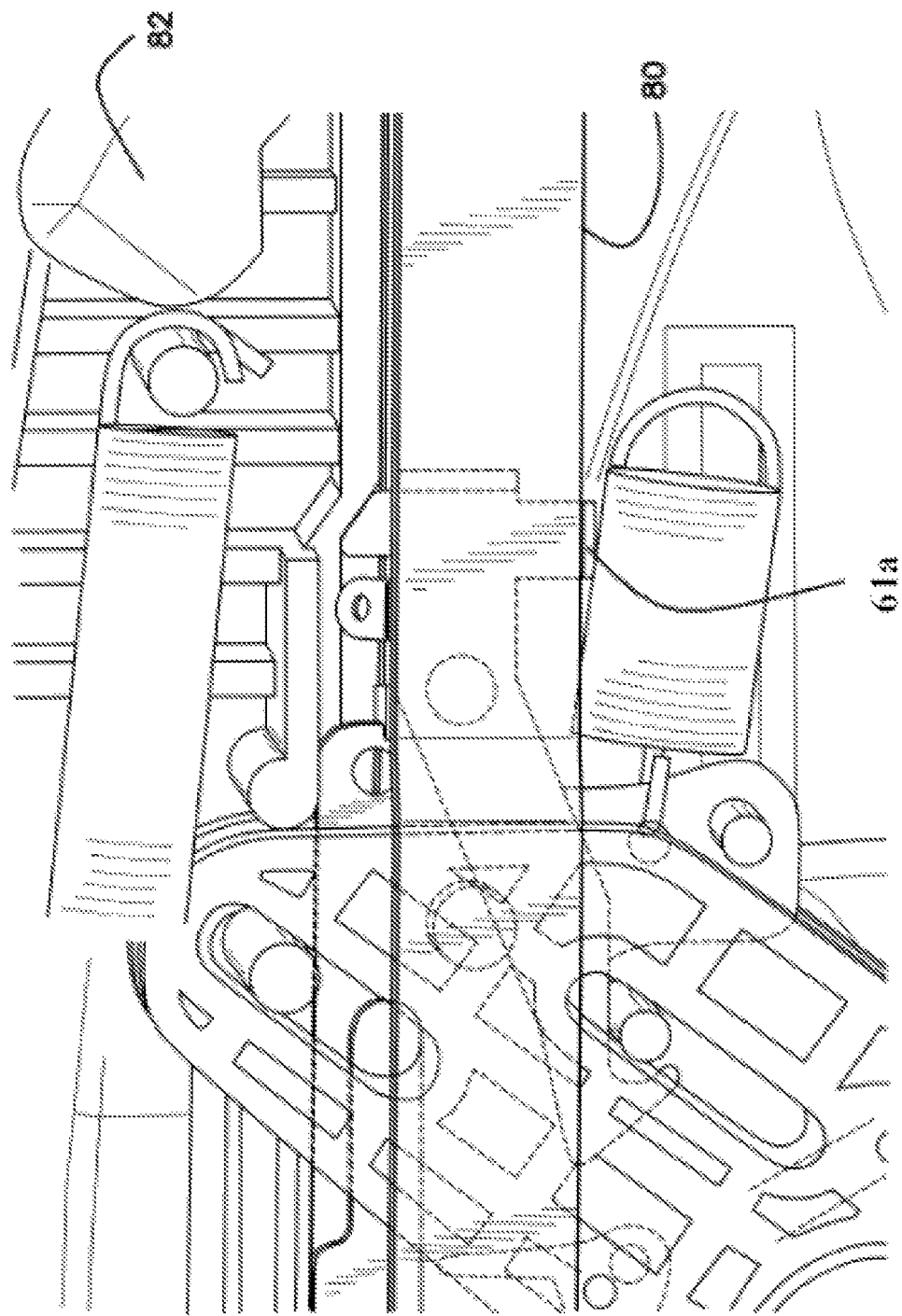

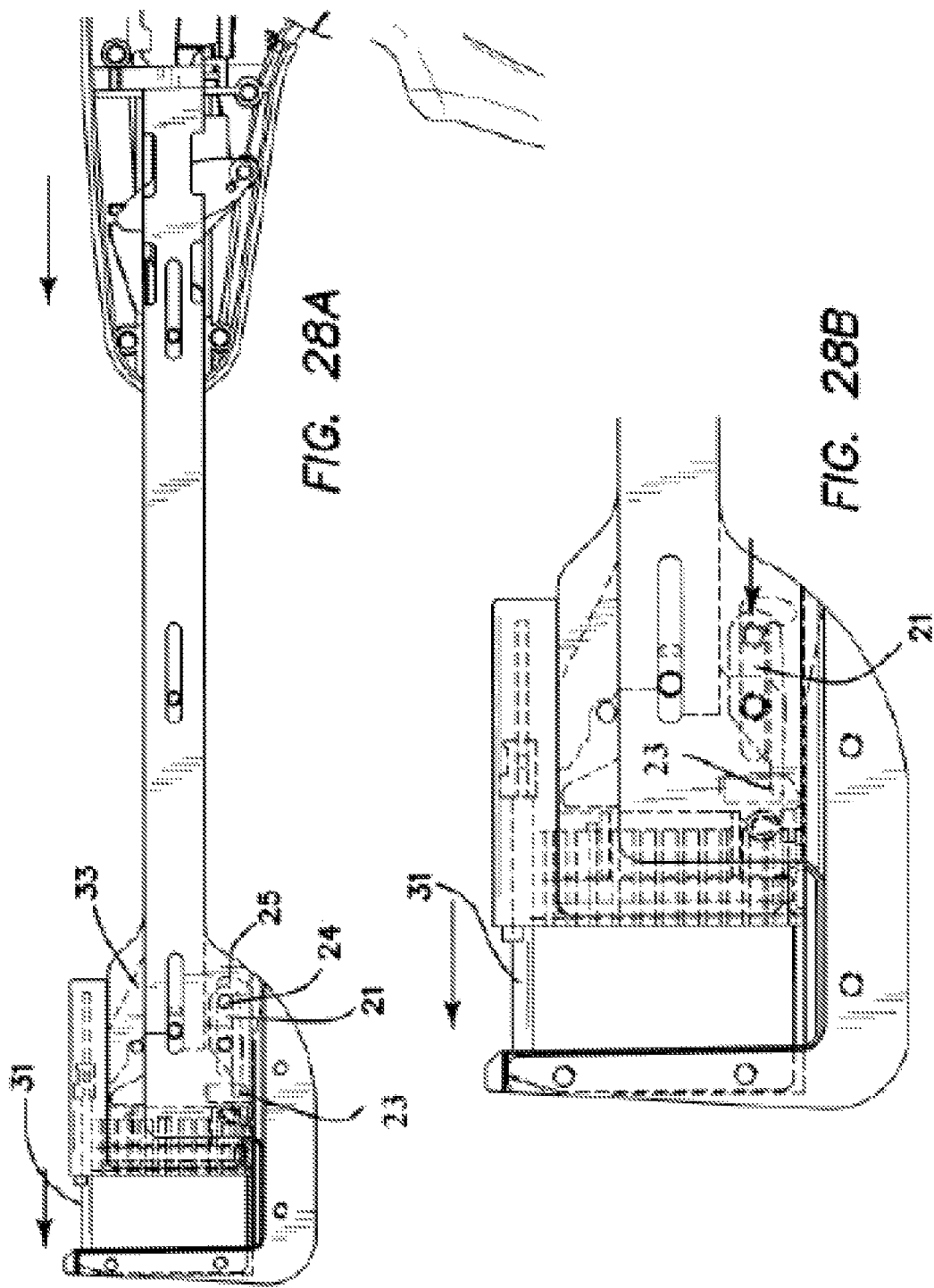

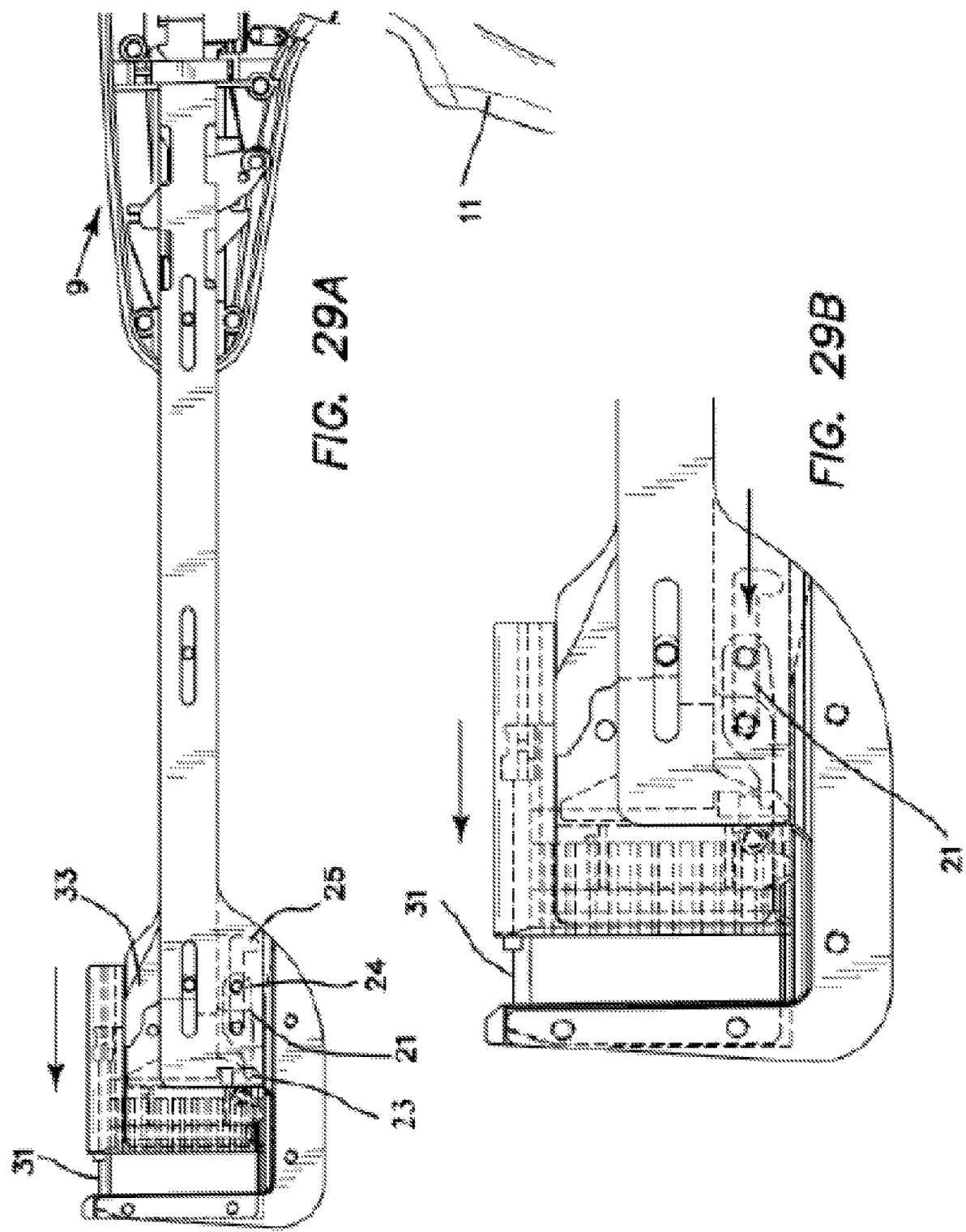

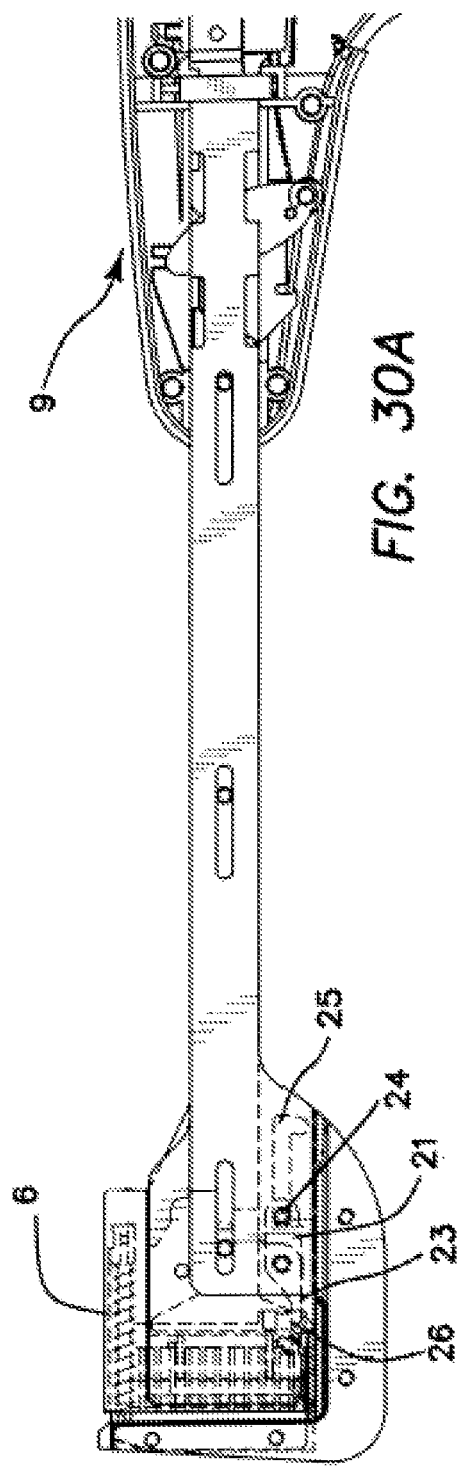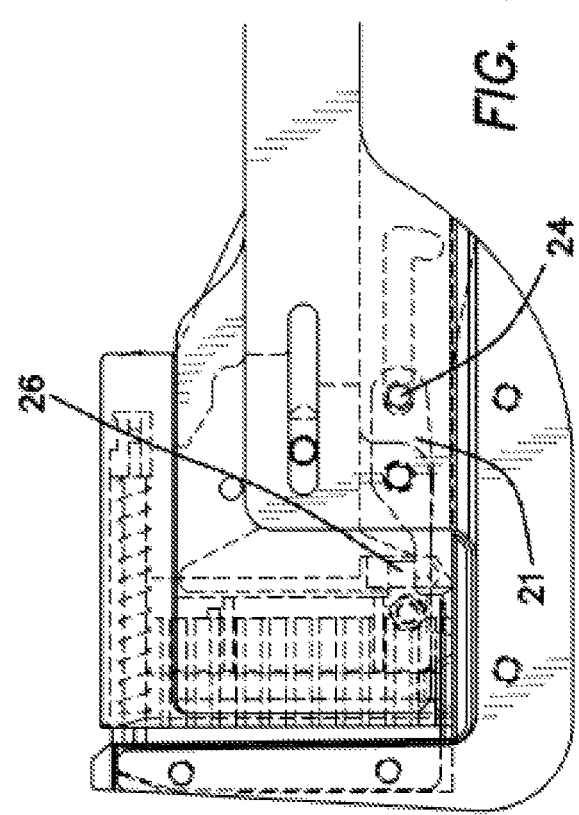

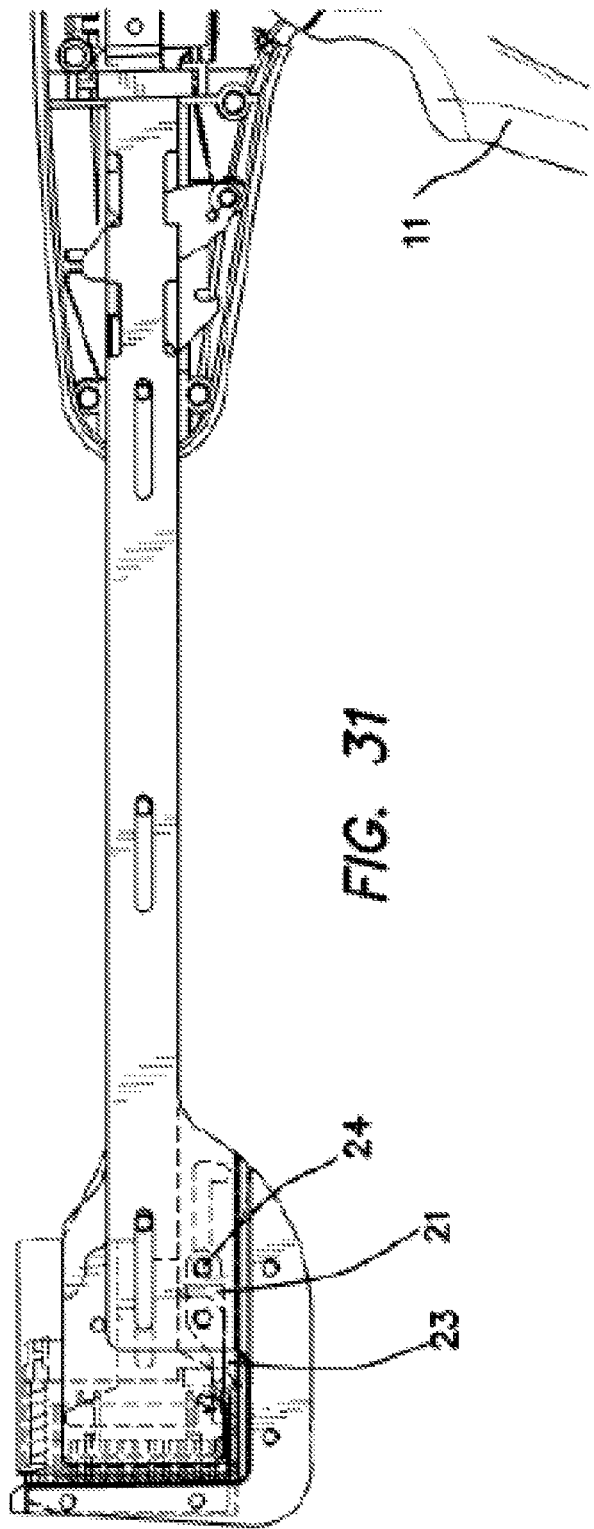

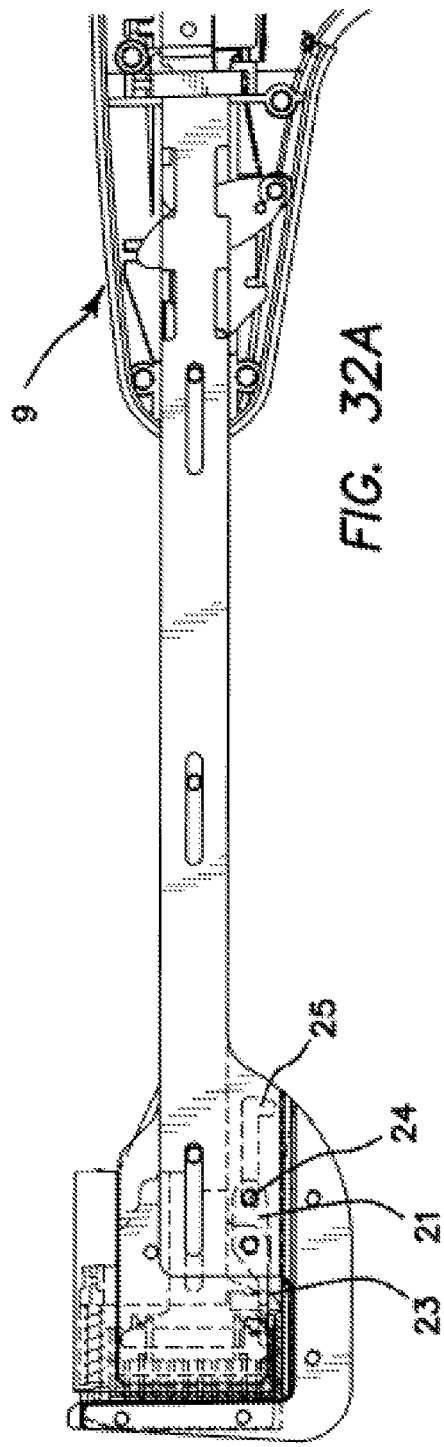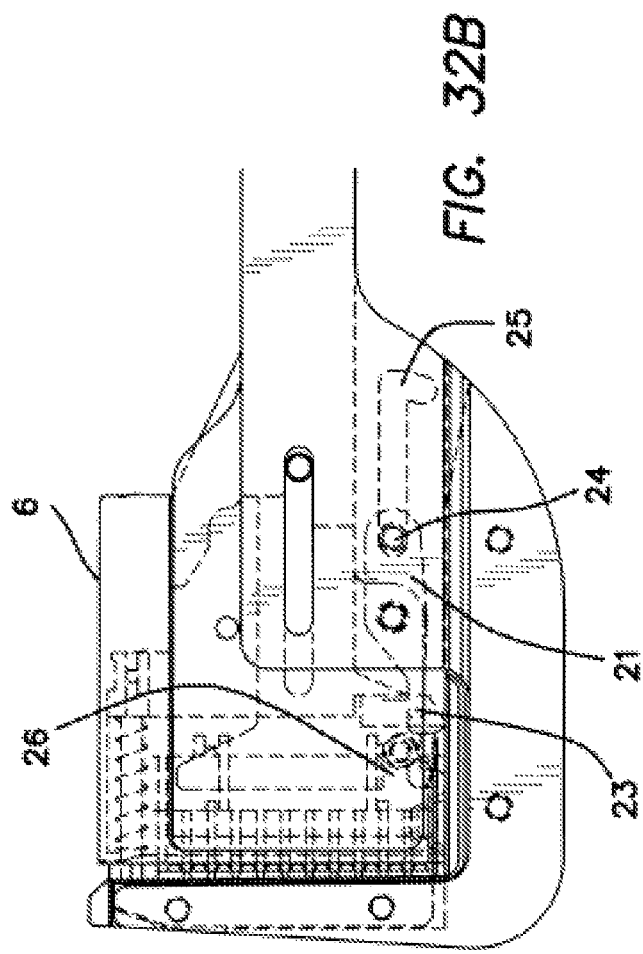

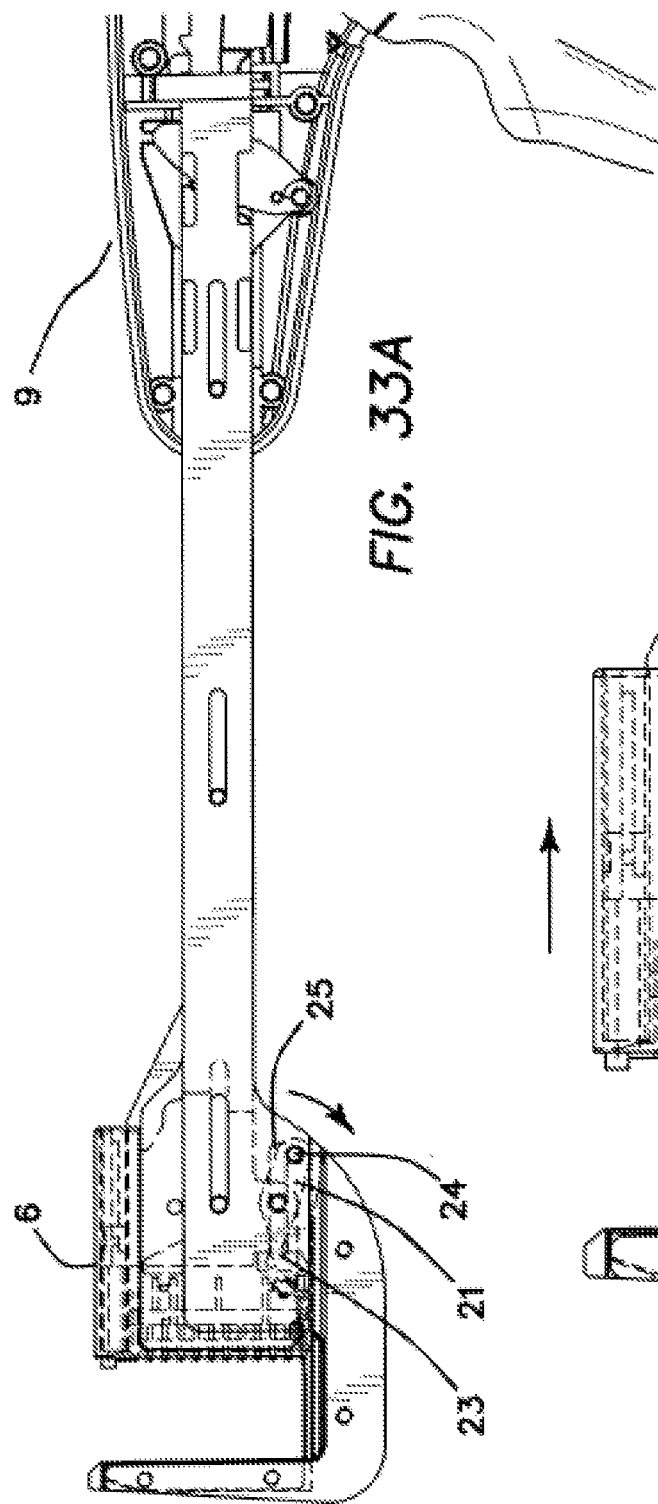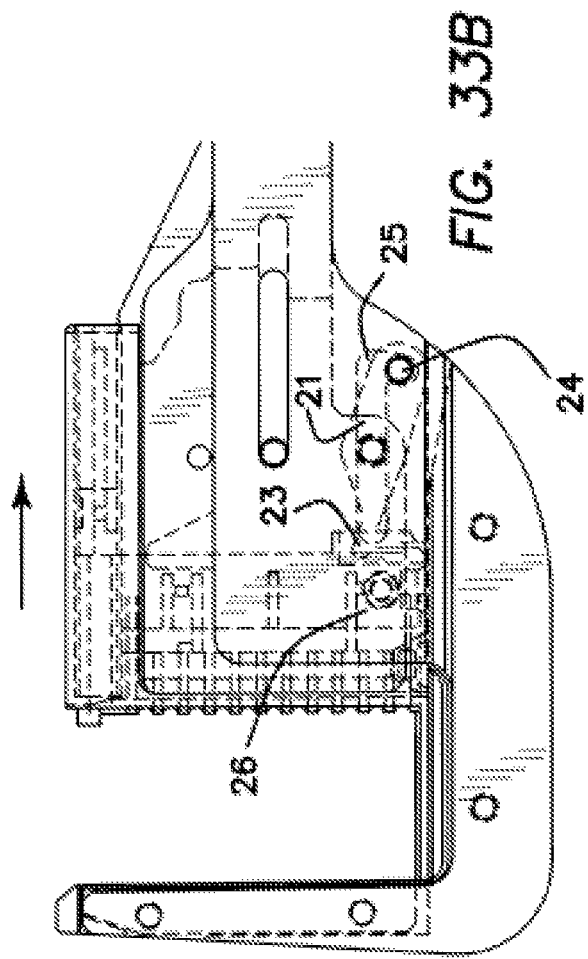

SURGICAL STAPLER WITH FIRING LOCK MECHANISM

CROSS-REFERENCE TO RELATED APPLICATIONS

This application is a continuation of U.S. patent application Ser. No. 13/618,453, entitled "SURGICAL STAPLER WITH FIRING LOCK MECHANISM" filed on Sep. 14, 2012, currently pending, which is a continuation of U.S. patent application Ser. No. 13/100,022, entitled "SURGICAL STAPLER WITH FIRING LOCK MECHANISM" filed on May 3, 2011, issued as U.S. Pat. No. 8,281,972, which is a continuation of U.S. patent application Ser. No. 12/796,503, entitled "SURGICAL STAPLER WITH FIRING LOCK MECHANISM" filed on Jun. 8, 2010, issued as U.S. Pat. No. 7,934,629, which is a continuation of U.S. patent application Ser. No. 12/495,384, entitled "SURGICAL STAPLER WITH FIRING LOCK MECHANISM" filed on Jun. 30, 2009, issued as U.S. Pat. No. 7,731,073, which is a continuation of U.S. patent application Ser. No. 11/805,094, entitled "SURGICAL STAPLER WITH FIRING LOCK MECHANISM," filed on May 21, 2007, issued as U.S. Pat. No. 7,552,854, which claims the benefit of U.S. Provisional Application No. 60/747,790, filed May 19, 2006, the disclosures of each of which are hereby incorporated by reference as if set forth in full herein.

BACKGROUND

The present invention relates generally to surgical occlusion instruments and, more particularly, to surgical staplers.

Surgical staplers are used to approximate or clamp tissue and to staple the clamped tissue together. As such, surgical staplers have mechanisms to ensure that tissue is properly positioned and captured prior to driving staples through the tissue. This partly entails that the clamped tissue together is compressed or squeezed to ensure that the width of the clamped tissue is not too large so as to prevent the staples from forming against the anvil of the stapler as well as not too narrow as to eliminate capillary function in the clamped tissue. Mechanisms have also been provided to ensure that staples are loaded in the stapler prior to clamping the tissue.

As a result, this has produced, for example, multiple triggers and handles in conjunction with complex mechanism to provide proper stapling of the clamped tissue. With these complex mechanism, these mechanism increase manufacturing burdens, introduces potential sources for device failure and confusion for the user. Thus, reliable stapling of clamped tissue without complex mechanisms is desired.

SUMMARY

Generally, a surgical stapler is provided. In one aspect, a surgical stapler comprises a shaft, an actuator and a staple pusher. The shaft extends along a longitudinal axis having a proximal end and a distal end, a first jaw and a second jaw extending from the distal end of the shaft. The second jaw is arranged to receive a staple cartridge having a plurality of staples and is movable along the longitudinal axis towards the first jaw. The actuator is coupled to the proximal end of the shaft. The staple pusher is coupled to the actuator and is movable along the longitudinal axis to push the plurality of staples out of the cartridge along the longitudinal axis. The staple pusher has a distal portion pivotally connected to a proximal portion. The distal portion has a first position and a second position with the first position preventing movement of the staple pusher towards the first jaw.

In one aspect, a surgical stapler comprises a shaft, an actuator and a staple pusher. The shaft extends along a longitudinal axis having a proximal end and a distal end, a first jaw and a second jaw extending from the distal end of the shaft. The second jaw is arranged to receive a staple cartridge having a plurality of staples and is movable towards the first jaw along the longitudinal axis. The actuator is coupled to the proximal end of the shaft. The staple pusher is coupled to the actuator and is movable along the longitudinal axis to push the plurality of staples out of the cartridge along the longitudinal axis. The surgical stapler also comprises means for preventing longitudinal movement of the staple pusher.

In one aspect, a stapler comprises a shaft and an actuator. The shaft has a distal end with a first jaw connected to an anvil, a movable second jaw arranged to receive a staple cartridge and a staple pusher movable within the second jaw. The second jaw is movable towards the first jaw in a longitudinal direction. The actuator is connected to a proximal end of the shaft and has a movable trigger connected to a stationary handle housing. A firing lever is encased in the stationary handle housing and the firing lever has a hook operationally connected to a projection extending from the staple pusher.

Many of the attendant features of the present invention will be more readily appreciated as the same becomes better understood by reference to the foregoing and following description and considered in connection with the accompanying drawings in which like reference symbols designate like parts throughout.

BRIEF DESCRIPTION OF THE DRAWINGS

FIG. 13 is a perspective view of a surgical stapler in accordance with various aspects of the present invention;

FIGS. 14-15D are side views of a surgical stapler in accordance with various aspects of the present invention;

FIGS. 27-35 are side views of a surgical stapler in accordance with various aspects of the present invention.

DETAILED DESCRIPTION

Figure 1:
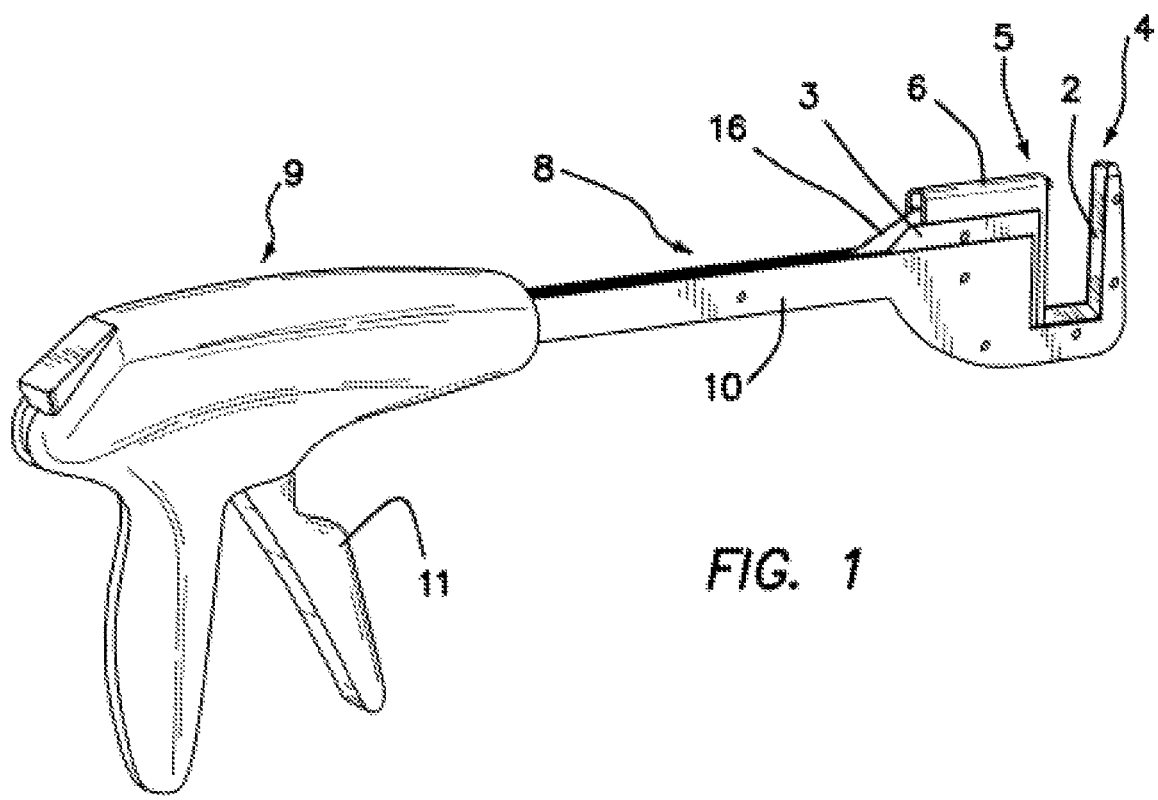
FIG. 1 is a perspective view of a surgical stapler in accordance with various aspects of the present invention.
Figure 2A:
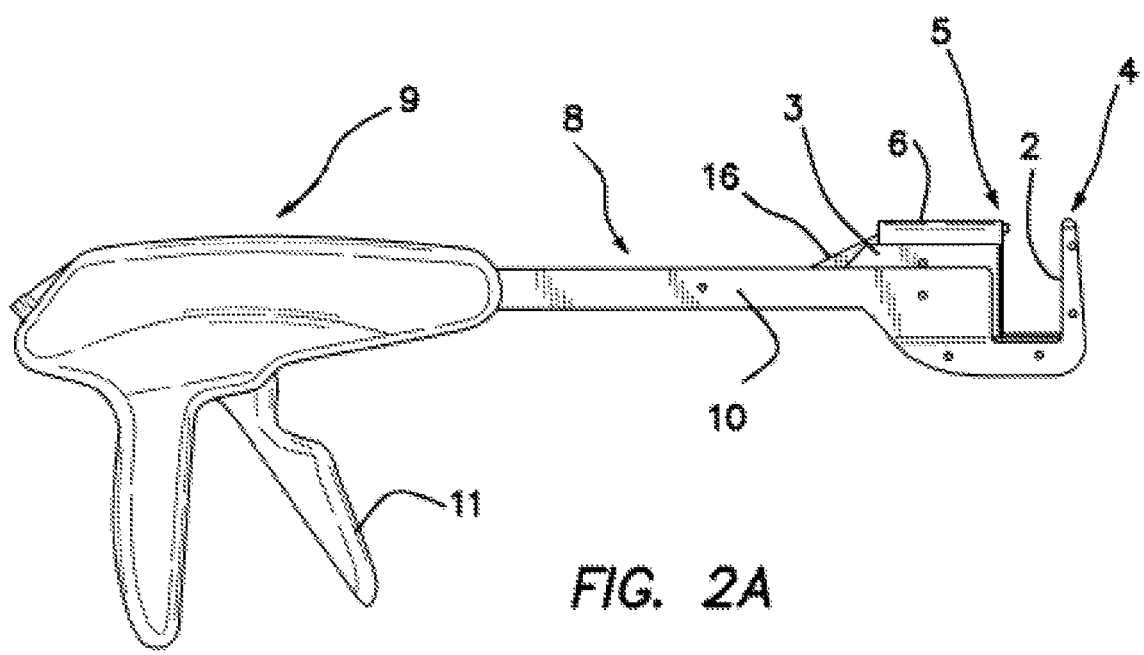
FIG. 2A is a side view of a surgical stapler in accordance with various aspects of the present invention.
Figure 2B:
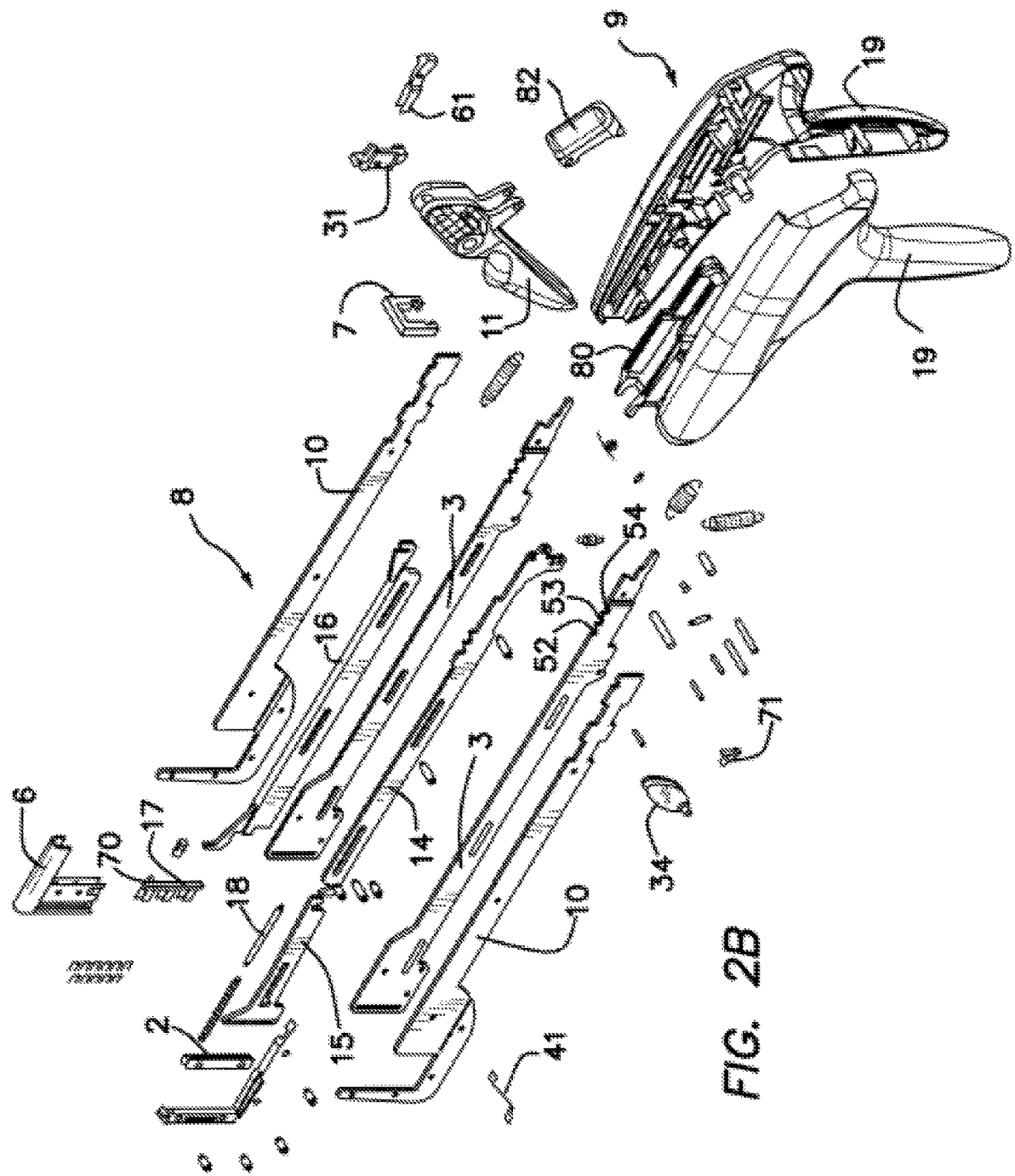
FIG. 2B is a exploded view of a surgical stapler in accordance with various aspects of the present invention.
Figure 2C:
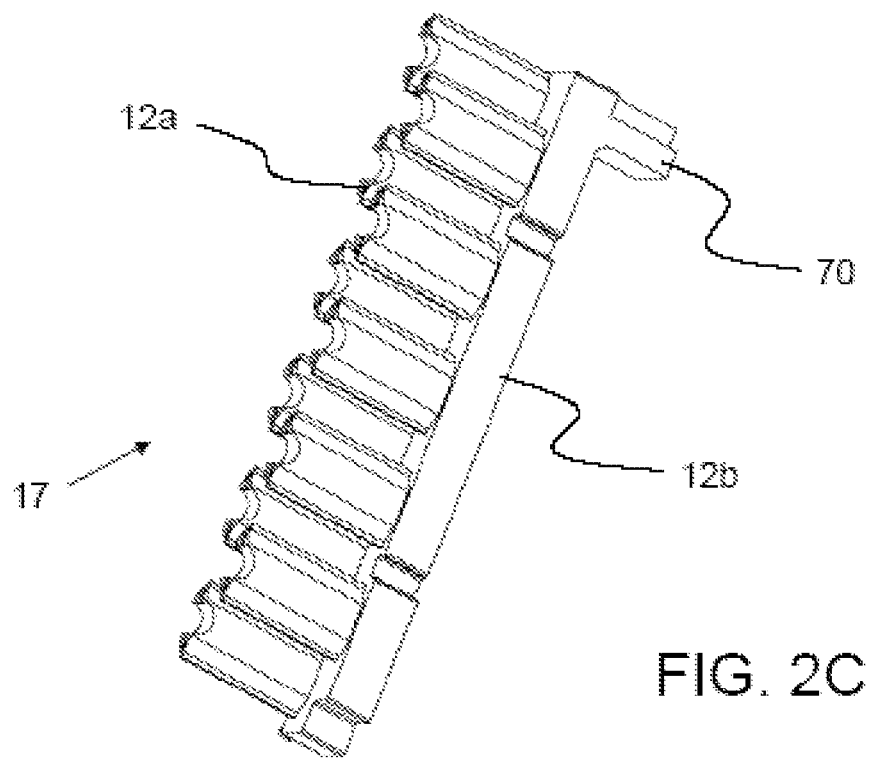
FIG. 2C is an enlarged perspective view of staple drivers in accordance with various aspects of the present invention.
Figure 2D:
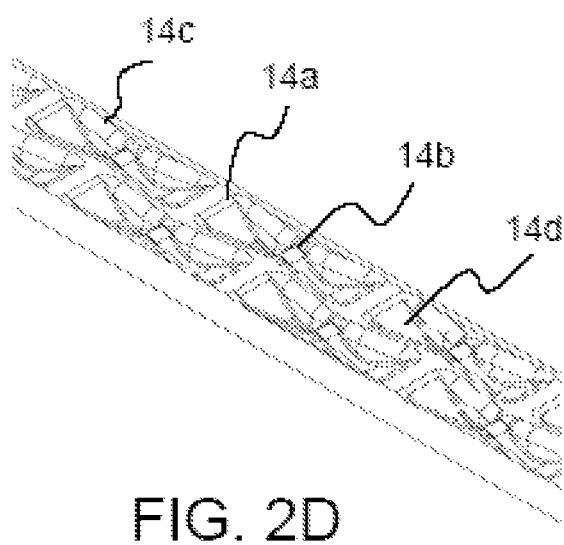
FIG. 2D is an enlarged top view of an anvil in accordance with various aspects of the present invention.
Figure 2E:
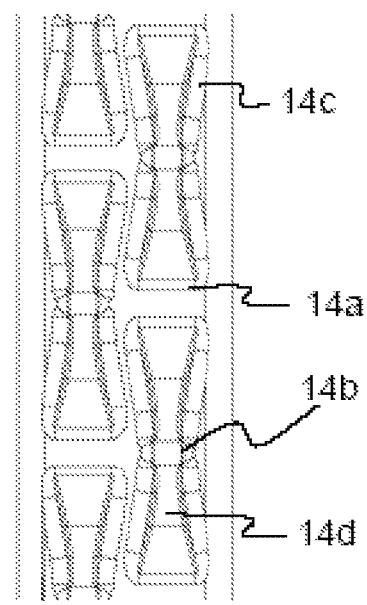
FIG. 2E is an enlarged perspective view of an anvil in accordance with various aspects of the present invention.

In FIGS. 1-2, a surgical stapler has a barrel or shaft 8 extending along a longitudinal axis with an actuator 9 connected to a proximal end of the shaft. End effectors or jaws 4,5 are integrally formed or extend from a distal end of the shaft 8. Disposed on jaws 4,5 are an anvil 2 and a cartridge 6. In one aspect, the anvil 2 is disposed on jaw 4, which is stationary and is integrated with frame 10 of the shaft 8. The cartridge support 3, part of jaw 5, is movable and is arranged to receive the removable cartridge 6. The cartridge contains one or more staples or fasteners and one or more staple drivers 17 such that when pressure is applied to the staple drivers 17, the staples are ejected or fired from the cartridge 6 through tissue clamped or compressed between the jaws 4,5. A staple pusher 14,15 provides or communicates the pressure to fire the staples. In one aspect, the staple drivers 12 has at least one distal surface 12a arranged to drive a staple out of the staple cartridge and at least one proximal surface 12b arranged to contact the distal portion of the staple pusher 14,15. The distal portion of the staple pusher in one aspect has an enlarged end arranged to contact the at least one proximal surface of the staple driver.

The shaft 8 comprises the staple pusher 14,15, the cartridge holder, retainer or support 3, frame 10 and a capture pin pusher 16. The frame 10 is fixed to the actuator 9. The staple pusher 14,15, the cartridge support 3 and capture pin pusher 16 are movable relative to the frame 10 and the actuator 9 traversing along a longitudinal axis of the surgical stapler. In one aspect, the cartridge support comprises two symmetrical elongate shafts or slides connected together on a proximal end by a support block case 31. The block case 31 in one aspect provides a hook or post from which a spring 91 is attached on one end and connected to the actuator 9 on the other end. The spring biases the cartridge support 3 via the block case proximally or away from the anvil 2 and towards the actuator 9. The distal end of cartridge support 3 defines an opening arranged to receive the cartridge 6 and in one aspect extends or spreads orthogonally from the two side plates, slides or elongate shafts forming an enlarged "T" or "hammer head" like shape or profile.

The frame 10 defines a channel through which the cartridge support 3 moves, e.g., slides longitudinally relative to the actuator 9. The cartridge support 3 with the cartridge 6 moves longitudinally relative to the actuator 9 to capture and clamp tissue between the cartridge and the anvil 2. The cartridge support 3 in one aspect also defines a channel through which the staple pusher 14,15 and the capture pin pusher 16 are disposed and movable therethrough. The staple pusher 14,15 interacts with the cartridge 6 to eject staples from the cartridge 6 by contacting staple drivers 17 within the cartridge 6. In one aspect, the staple pusher 14,15 are attached to a spring 94 which is connected the actuator 9. The spring biases the staple pusher 14,15 proximally or away from the anvil 2 and towards the actuator 9. The capture pin pusher 16 also interacts with the cartridge 6 to cause a spring loaded capture pin 18 situated in the cartridge 6 to extend into or allow retraction from the anvil 2.

The actuator 9 comprises a trigger 11 pivotably coupled to a stationary handle housing 19. The frame 10 in one aspect comprises an elongate body or shaft with one end, a proximal end, fixedly coupled to the actuator 9. The other end of the elongate body of the frame 10 is generally U-shaped with the anvil 2 attached to or extending along the frame on an axis perpendicular to the longitudinal axis of the elongate body of the frame 10. In one aspect, the anvil is integral with the frame 10 forming a monolithic structure. The frame 10 in one aspect comprises symmetrical support blades both fixedly attached together on either end with one end coupled to the actuator 9 and the other end coupled to or forming the anvil 2. Sufficient springs, pins, posts, spacers, slots, detents and other similar components or formations are also provided to secure various components of the stapler together and to facilitate operation of the stapler.

In one aspect, the anvil 2 comprises a plurality of staple pockets having a generally hourglass shape with squared off ends 14a. The width of the middle or center portion 14b is smaller than the width of the ends 14a to facilitate formation of staples driven against the staple pocket. The squared off ends providing a large first contact area directing the staple ends towards the narrow middle portion to form a staple. Two cavities are separated by the middle portion with a slope curving up to the middle portion from each of the staple ends 14a. A sloping surface 14c slopes from the top surface of the anvil 2 and surrounds a trough 14d or pocket for receiving the legs of a staple. The staple is formed as the legs are deflected towards the center portion 14b of the trough. The trough is shallow and slopes downward from the sloping surface 14c but is somewhat raised at its center. The staple in one aspect is symmetrical, e.g., round or square. In one aspect, the staples are flatten along one surface, e.g., the top and/or, along a symmetrically opposing surface, e.g., the bottom. The cross-sectional shape of the staple or periphery is not fully symmetrical, e.g., an oval versus a circle.

In one aspect, the cartridge 6 has a groove or elongate cavity that mates and aligns with a corresponding projection or elongate raised portion in the cartridge support 3 on the stapler. The projection and cavity combination identifies specific cartridge types, e.g., vascular versus non-vascular. The staple drivers or ejectors in the cartridge are provided in three columns extending from a single contact base to simultaneously eject all the staples in the cartridge to form against a corresponding three columns of staple pockets in the anvil.

In operation, a cartridge is loaded in the cartridge support 3 of the stapler. The stapler jaws 4,5 are positioned to place tissue between the jaws 4,5. If the loaded cartridge does not have staples, the trigger 11 is not allowed to move or be actuated. Actuating the trigger 11, after a staple filled cartridge is loaded, causes the capture pin 18 to deploy and the jaws 4,5 to move together. Thus, tissue becomes encased or encompassed between the jaws 4,5/frame 10 and the capture pin 18. As such, the tissue can be initially captured without placing significant pressure or force on the tissue from the jaws 4,5. Users, such as a surgeon, are thereby afforded the options of further fine tuning the positioning of the stapler, leaving the stapler in place to perform other surgical tasks, continue to operate the stapler or start over. Actuating the trigger 11 further causes the cartridge support 3 to move further towards the anvil 2 to partially close the jaws 4,5 and/or clamp tissue. Completing the actuation stroke of the trigger 11 causes the jaws 4,5 to clamp or compress the tissue therebetween.

Unless the actuation stroke of the trigger 11 is completed, the surgical stapler does not permit the firing of staples from the cartridge. From capturing the tissue, partially closing and fully clamping the tissue, the user is provided multiple predetermined set points and positions to appropriately align and position the stapler jaws 4,5 relative to the tissue as desired. A release button 82 is provided, in one aspect, that when actuated allows the stapler to be reset back to the initial or default position, i.e., jaws opened, as desired, to remove or re-position the location of the stapler. The second or subsequent full or complete actuation stroke of the trigger 11 causes the staple pusher 14,15 and staple driver 17 to move and eject the staples from the cartridge 6.

Referring also now to FIGS. 3A-12, the predetermined or set positions of the cartridge support 3 relative to the anvil 2 are maintained by latch 7. In one aspect, flat surfaces or edges of the latch 7 interact with slots or notches (e.g., first, second and third slots 52, 53, 54) in the cartridge support 3 to ensure that the cartridge support 3 moves or operates in discrete predetermined positions. The latch in one aspect is generally u-shaped having flat surfaces with a generally square or rectangle cross-section. The positions in one aspect comprise open, capture, partially closed and closed positions. The sequential movement of the latch in each of the slots 52, 53, 54 ensures the proper positioning of the cartridge relative to the tissue and the anvil to optimally allow the stapler to operate at each position removing the random positioning of the cartridge relative to the anvil. For example, the closed position as predetermined by the latch and slot interaction ensures the distance between the cartridge and the anvil is sufficient to effectively form and secure a staple through a tissue clamped there between. A firing lever 61 operatively engages the staple pusher 14,15 to permit firing of the staples after the jaws are fully closed. In one aspect, the firing lever is an elongate hook or partially curved or slanted elongate lever or anchor. After firing or ejecting the staples from the cartridge, a handle fire lock lever 71 operatively engages the cartridge support 3 to prevent the trigger 11 from opening or moving proximally even if the trigger is released. In one aspect, the fire lock lever 71 is a hook or partially curved or slanted lever or anchor.

Figure 3A:
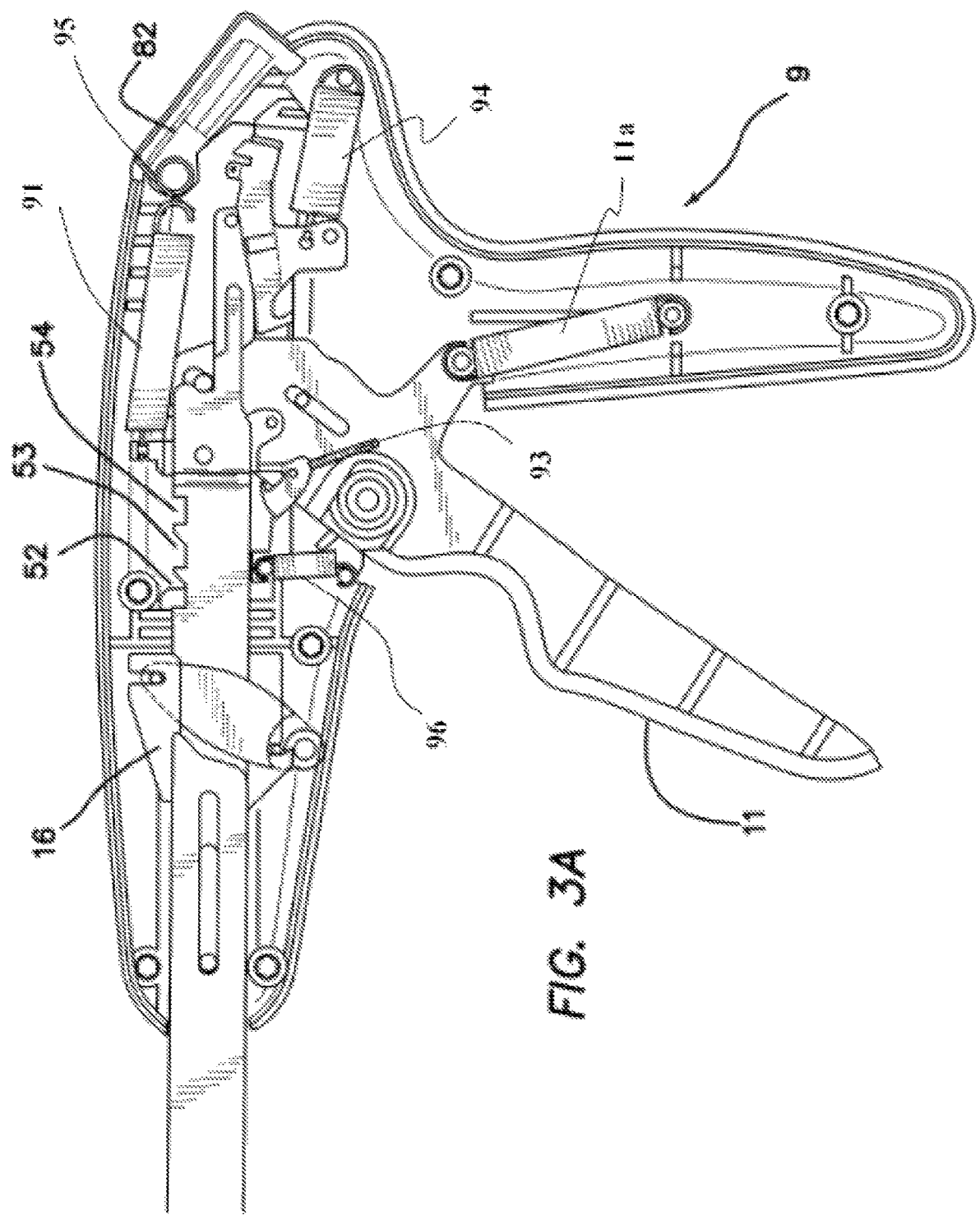
FIGS. 3A-12 are side views of a surgical stapler in accordance with various aspects of the present invention.
Figure 3B:
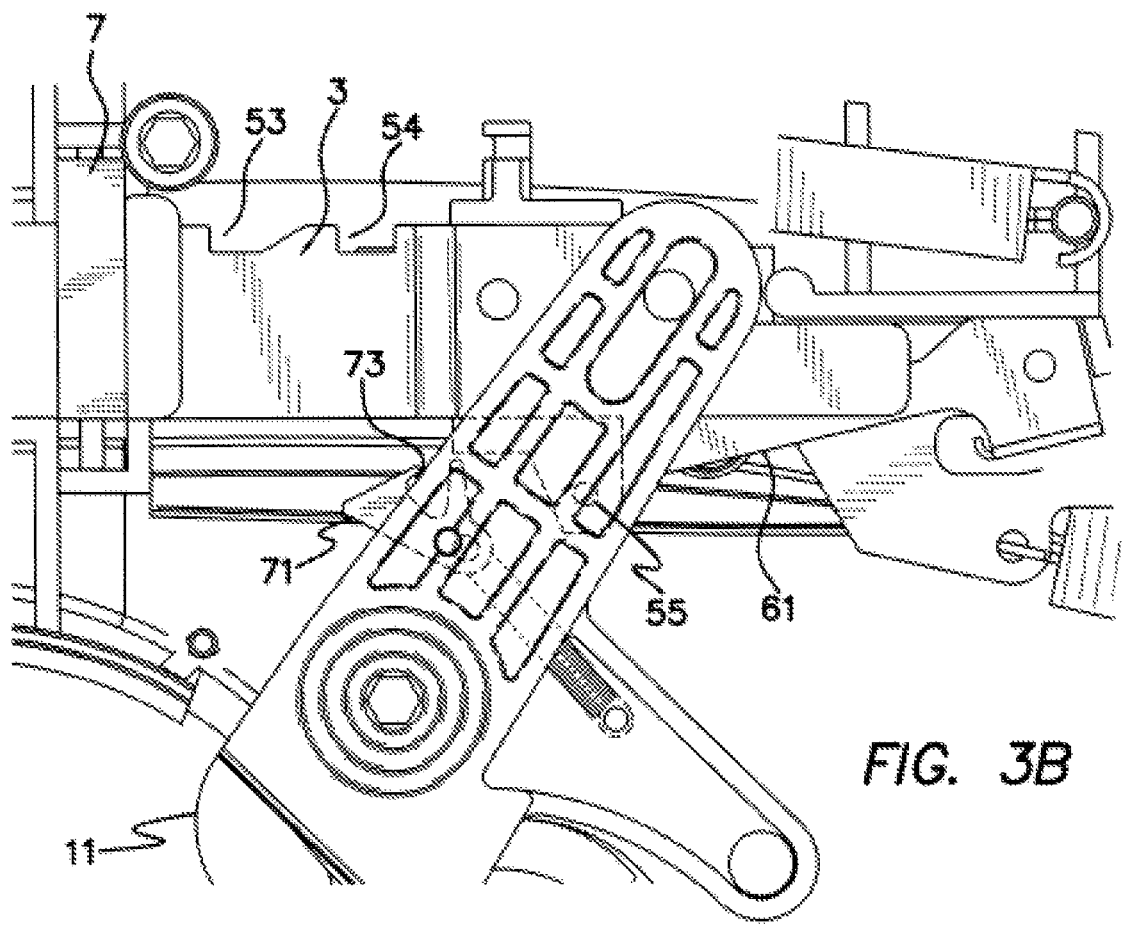

In FIGS. 3A-B, the default or open position is shown with latch 7 positioned or riding along a top surface or edge of the cartridge support 3. The trigger 11 of actuator 9 is connected to a post, projection or pin 51 that rests in a cavity or notch of the cartridge support 3, when the stapler is in an open, default, initial or resting position, i.e., the jaws are open to receive tissue there between. In the open position, the latch 7 is not engaged or situated in one of slots 52, 53, 54 on the cartridge support 3. The latch 7 rests or is secured within a cavity or channel disposed in the actuator 9, which restricts longitudinal or horizontal movement of the latch, but allows vertical or perpendicular movement of the latch.

The firing lever 61 is pivotally connected to the actuator 9 on one end and operatively connected to the staple pusher 14,15 on the other end. The other end or tip of the lever 61 moves somewhat freely and is deflected downward or traverse to the longitudinal direction, i.e., prevented from being in a horizontal or longitudinal position, when the jaws 4,5 are in the open position. The firing lever 61 is also coupled to the actuator 9 in one aspect by a spring 92 that biases the lever to the longitudinal position and in a clockwise direction. The handle fire lock lever 71 is also disposed within the actuator and is pivotally connected to the trigger 11 on one end. In one aspect, the fire lock lever 71 is also coupled to the actuator by a spring 93 that biases the lever to a longitudinal or horizontal position and in a clockwise direction. The fire lock lever 71 has a notch 73 arranged to receive a projection, post or pin 55 connected to the cartridge support 3.

In placing the stapler in a capture configuration or position from the open or initial position, the trigger 11 is pulled or actuated. The cartridge support 3 (jaw 5) moves closer to the anvil 2 (jaw 4) via pin 51 coupled to the trigger 11. The latch 7 is longitudinally fixed to the actuator 9 and thereby slides along the surface of the cartridge support 3 as the cartridge support moves towards the anvil 2. After a predetermined distance is traversed, the latch 7 falls into or is biased into a slot 52 in the cartridge support 3. The engagement or interaction of the latch 7 with the cartridge support 3 causes the jaws and thus the cartridge and anvil to maintain the captured position. The capture pin pusher 16 and the corresponding capture pin 18 also move such that the capture pin is deployed from the cartridge 6 into a cavity or opening in the anvil 2. Further description of the capture pin and pusher is described later below.

Figure 4:
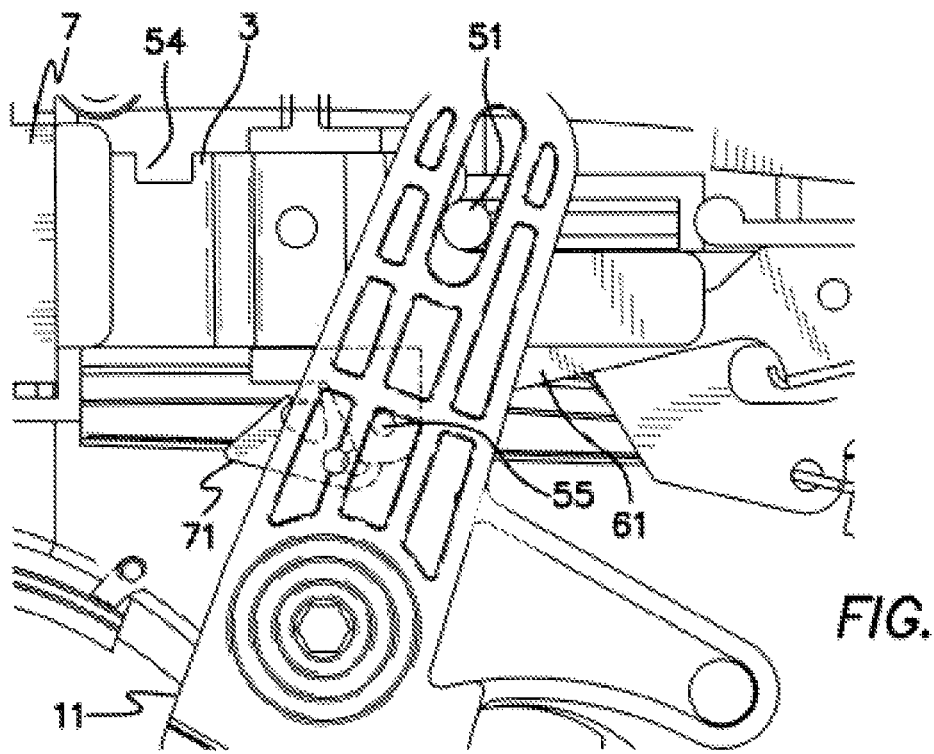

As the trigger 11 is further actuated, the latch 7 rides along the proximal sloped surface of slot 52 to be positioned into the slot 53. With the latch 7 in slot 53 of the cartridge support 3, the partially closed position of the stapler is maintained, without further interaction by the user, e.g., pressure or force is removed from the trigger 11. In FIG. 4, the trigger 11 is pulled or actuated from the capture position. The cartridge support 3 moves distally towards the anvil 2 via pin 51 coupled to the trigger 11 to close or move the jaws 4,5 together, e.g., the jaw 5 with the loaded cartridge is moved closer to the jaw 4 as the cartridge support 3 moves distally. The cartridge support 3 is biased towards the proximal direction away from the anvil 2 and thus resists the distal movement. The latch 7 rides along a surface of the cartridge support 3 as the cartridge support 3 slides by the latch 7. The latch 7 moves into the slot 53 of the cartridge support 3 such that the cartridge support 3 moves sufficiently distally to partially close the jaws 4,5. In other words, a predetermined distance between a starting point of the latch 7 to the slot 53 along the cartridge support 3 corresponds to a predetermined distance between the jaws 4,5 from the capture position to the partially closed position. The engagement or abutment of the latch 7 with the distal edge of slot 53 in the cartridge support 3 along with the interaction of the spring 91 biasing the cartridge support in the proximal direction traps or fixes the cartridge support in position to allow the jaws 4,5 and thus the cartridge and anvil to maintain a partially closed position. The firing lever 61 remains deflected. In the partially closed position, the cartridge support 3 is moved distally and thus the pin 55 is also moved distally but does not yet contact or is received by the fire lock lever 71.

The staple pusher 14,15 is coupled to the cartridge support 3 and as such moves as the cartridge support 3 moves. Also, in one aspect, the pin 51 coupled to trigger 11 is operatively coupled to the staple pusher 14,15. The staple pusher 14,15 is further coupled to the latch 7 and in one aspect biased by a spring 91 coupled to the actuator 9 on one end and connected to the proximal end 62 of the staple pusher. The spring 91 biases the staple pusher in a proximal direction or away from the anvil 2. In one aspect, the staple pusher 14,15 has the same or less number of slots than the cartridge support 3. The slots in the staple pusher 14,15 are similar in size and shape to the slots in the cartridge support 3. Thus, as the trigger 11 is actuated, the staple pusher 14,15 moves and follows the movement of the cartridge support 3. Likewise, as the latch 7 maintains the position of the cartridge support 3, the position of the staple pusher 14,15 is also maintained via slots in the staple pusher or in one aspect the connection to the cartridge support 3.

Figure 5:
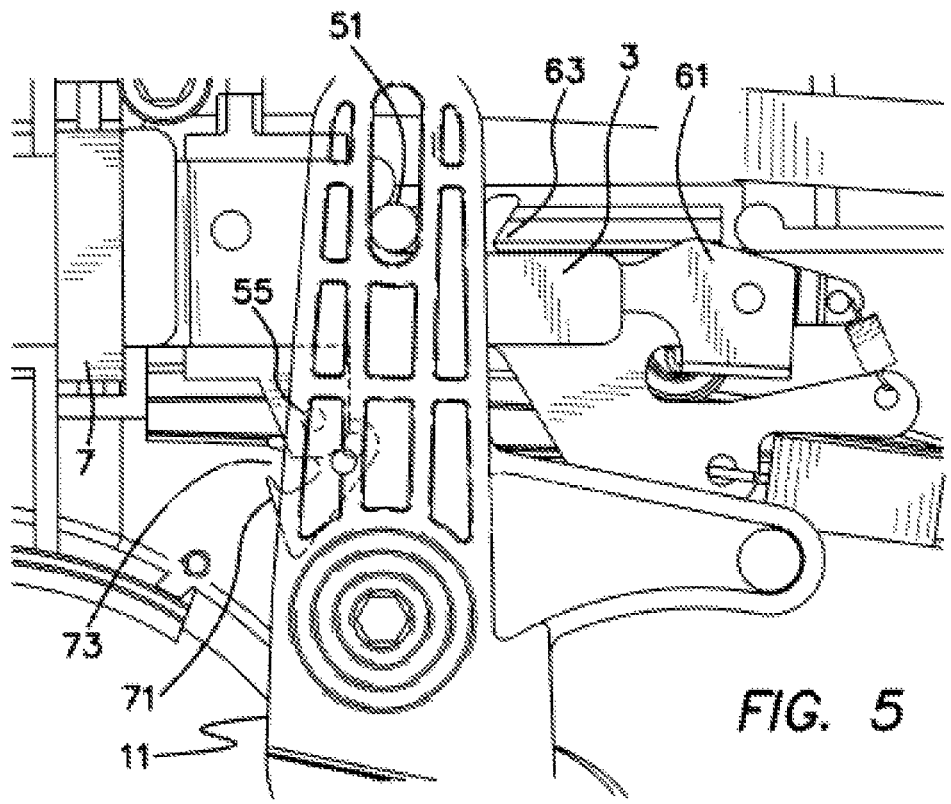

In FIG. 5, the trigger 11 is fully actuated or pulled, e.g., a full or complete actuation stroke, and as such the cartridge support 3 is moved distally via pin 51 to close or move the jaws 4,5 together. The latch 7 rides along the proximal sloped surface of the slot 53 and then moves into the slot 54 as the cartridge support 3 moves sufficiently distal or along a predetermined distance to fully close the jaws 4,5. The engagement or abutment of the edge or surfaces of latch 7 with the distal edge of slot 54 in the cartridge support 3 along with the interaction of the spring 91 biasing the cartridge support 3 in the proximal direction maintains the cartridge support in position thereby maintaining the jaws 4,5, the cartridge and anvil, in a closed or clamped position.

The firing lever 61 becomes unobstructed and thus moves to a horizontal position or aligns longitudinally with the cartridge support 3. In one aspect, pin 51 moves and thus the firing lever is unobstructed. Biased by spring 92, the firing lever pivots into longitudinal alignment with the cartridge support 3. As shown, the firing lever 61 has a hook or notch 63 arranged to operatively receive pin 51 connected to the trigger 11. The pin 55 moved further distally as the trigger moves engages or contacts the fire lock lever 71 deflecting the lever 71.

Figure 6:
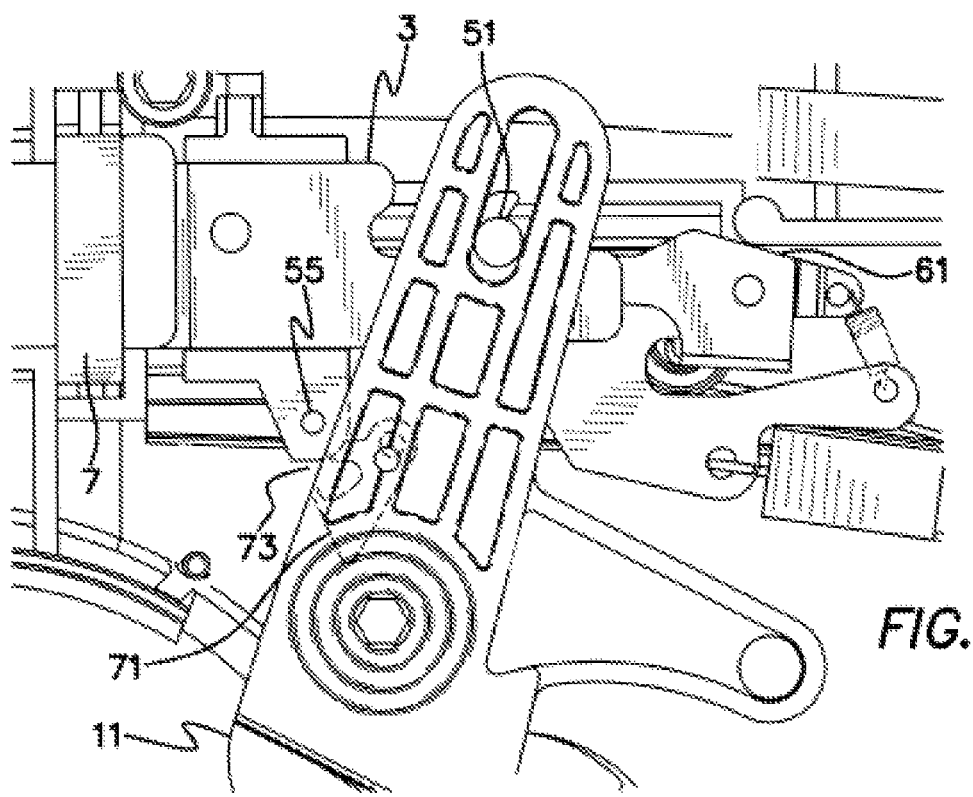

The trigger 11 is released as shown in FIG. 6, but the engagement of the latch 7 with the slot 54 in the cartridge support 3 continues to maintain the jaws 4,5 in the closed position. With the trigger released, the trigger pivots being biased by spring 11a. The pin 51 coupled to the trigger travels back proximally riding over a distal sloped surface 63b of the firing lever 61 and deflecting the firing lever 61. The firing lever 61 returns back to a horizontal or longitudinally aligned position once the pin 51 moves back sufficiently in the proximal direction, clearing the slanted, sloped or ramped surface or hook portion of the firing lever 61. The pin 55 coupled to the cartridge support 3 remains stationary and continues to contact and deflect the fire lock lever 71.

Figure 7:
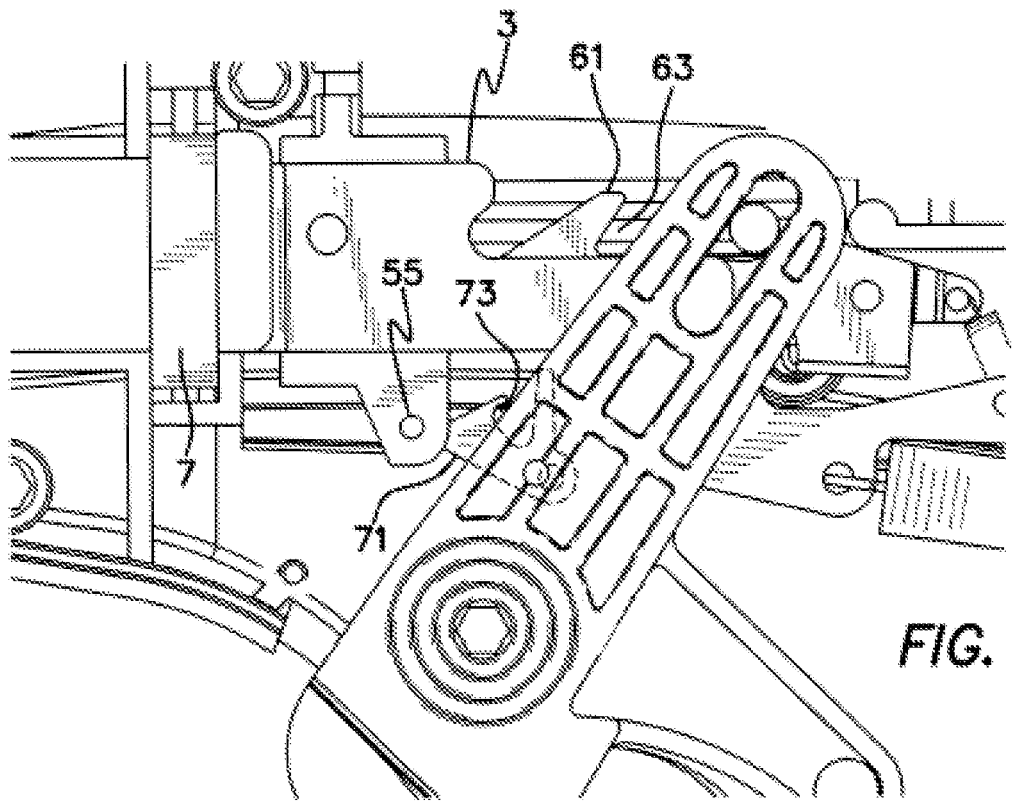

FIG. 7 shows the stapler in position to fire or eject the staples from the cartridge 6. The jaws 4,5 remain in the closed position. The pin 51 continues to travel back proximally along the firing lever 61 with the firing lever remaining in a horizontal or longitudinal position. The pin 55 remains stationary. The fire lock lever 71 moves in the proximal direction and pivots upon clearing the pin 55 allowing the fire lock lever 71 to move to a horizontal position.

Figure 8:
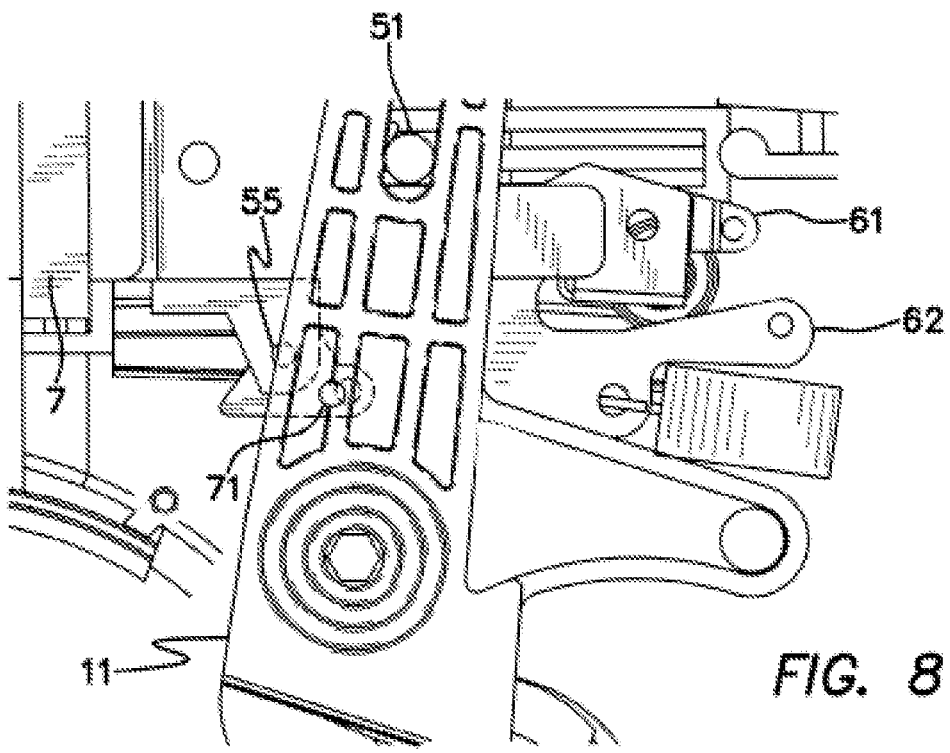

In FIG. 8, the stapler has fired or ejected the staples from the cartridge through the clamped tissue. The trigger 11 is fully closed, pulled or actuated. The engagement or contact of the surfaces or edges of latch 7 with the surfaces or edges of slot 54 in the cartridge support 3 along with the bias or force provided by the spring 91 continues to maintain the jaws in the closed position. In firing, actuating a firing stroke, the pin 51 connected to the trigger 11 moves distally to engage the notch 63 of the firing lever 61. The firing lever 61 connected to the staple pusher 14,15 causes the staple pusher to also move distally. As such, the staple pusher contacts and moves the staple drivers within the cartridge 6 subsequently ejecting the staples within the cartridge, and thus stapling the tissue clamped between the jaws 4,5.

The staple pusher 14,15 is coupled to the cartridge support 3 and as such moves as the cartridge support 3 moves. However, in one aspect, the staple pusher 14,15 has one less slot than the cartridge support 3, e.g., the staple pusher 14,15 does not have a slot that corresponds to the slot 54 on the cartridge support 3. In one aspect, the slot on the staple pusher 14,15 that corresponds to the slot 54 on the cartridge support is larger than the slot 54 in the cartridge support 3.

As such, the latch 7 maintains the position of the cartridge support 3 and the staple pusher 14,15, but the staple pusher 14,15 is allowed to move distally or towards the anvil 2. Thus, in firing, as the trigger 11 is actuated, the staple pusher 14,15 moves while the cartridge support 3 remains stationary. Also, with fewer components moving and less biasing forces tending towards the proximal direction, a tactile feedback is provided to the user indicating firing of the staples versus moving the cartridge or capturing/clamping the tissue.

The pin 55 remains stationary or fixed. In firing, the fire lock lever 71 connected to the trigger 11 moves distally to cause the lever 71 to pivot and engage the pin 55 to engage or rest within the notch 73 of the fire lock lever 71. The engagement of the fire lock lever 71 with the stationary pin 55, i.e., the pulling force of the fire lock lever 71 towards the proximal direction on the pin 55, prevents the trigger 11 from moving back distally or opening, even if the trigger is released. The locked or fixed trigger adjacent to the handle of the actuator 9 provides a visual feedback that the stapler has been fired, i.e., staples ejected.

The stapler can be reset during or after the operation of the stapler. For example, upon actuation of a release button 82, the stapler is reset or moved to its original or initial open position as the jaws 4,5 move apart or open. As shown in FIGS. 9-12, the latch 7 is lifted or moved out of engagement with the slot 54 in the cartridge support 3, which allows the cartridge support 3 to retract proximally. The latch 7 is connected to a release latch or arms 80 that is coupled to a release button 82 on the actuator 9 (FIGS. 13-14). In one aspect, with the button 82 actuated or pressed, arms 81 of the release latch 80 pivot and lift or move the latch 7 out of engagement with the cartridge support 3. The button 82 in one aspect is biased away from the actuator by a leaf spring 95 coupled to the actuator. In one aspect, the release arms 80 and latch 7 are biased to engage the cartridge support 3 by a compression spring 96 coupled to the actuator 9.

Figure 9:
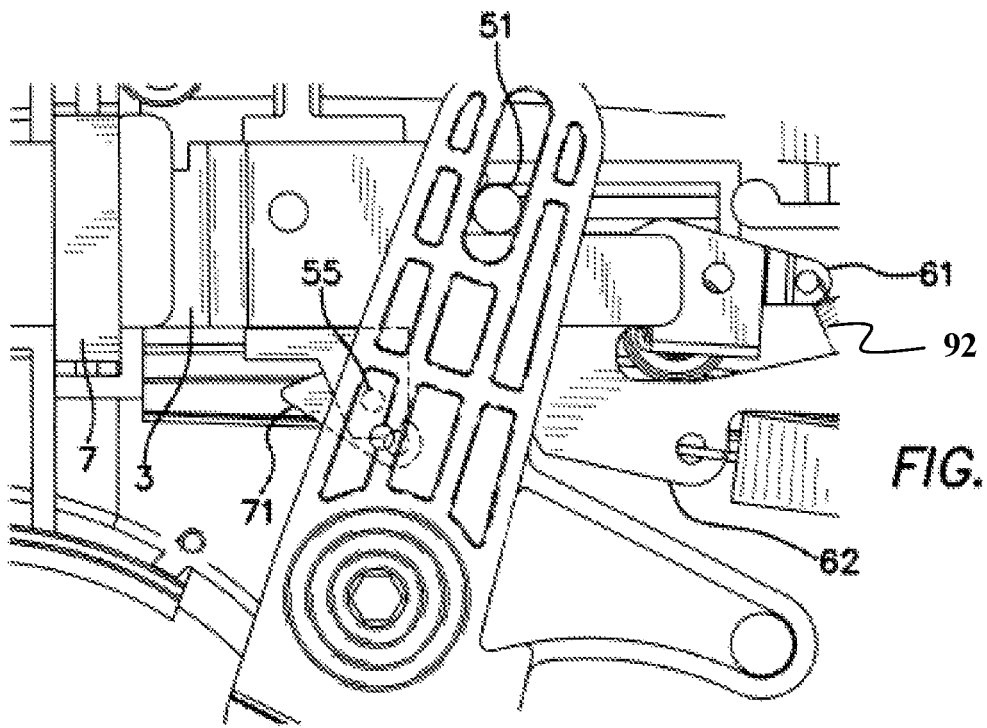
Figure 10:
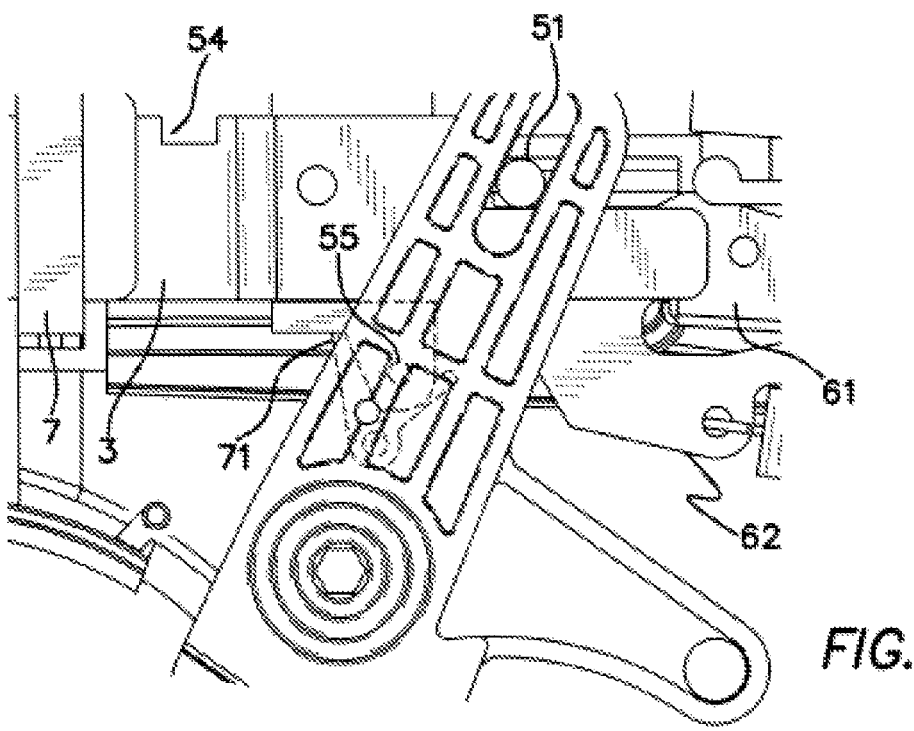
Figure 11:
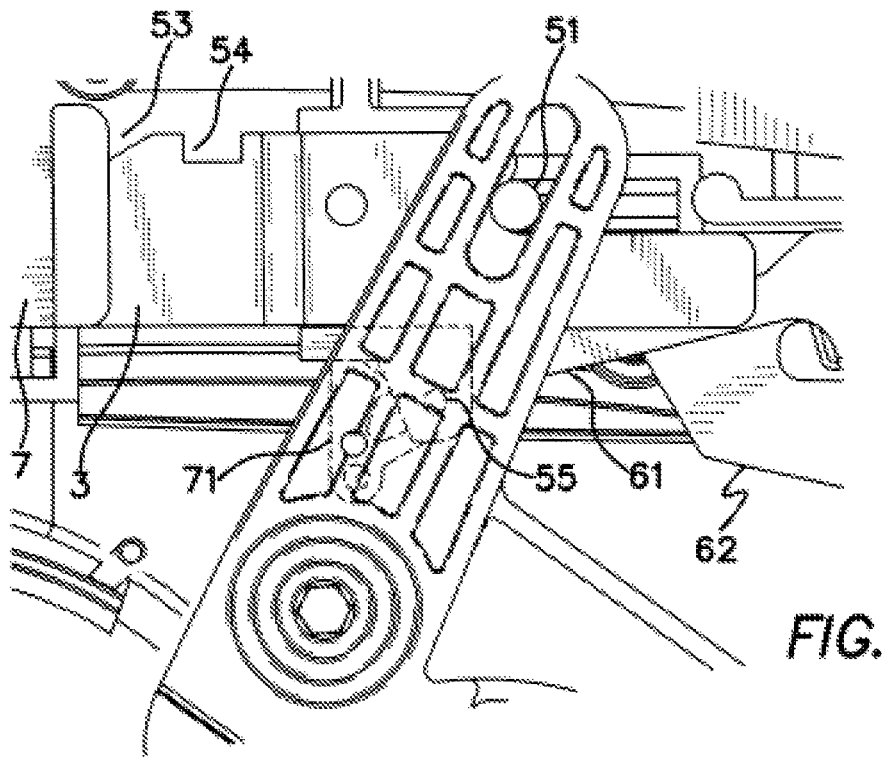
Figure 12:
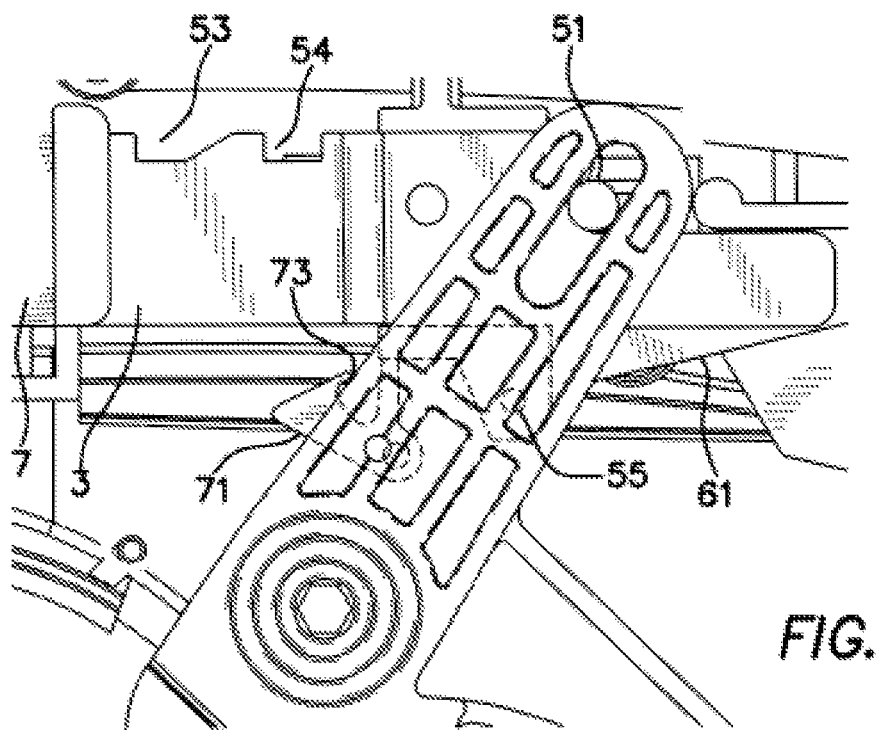
Figure 15A:
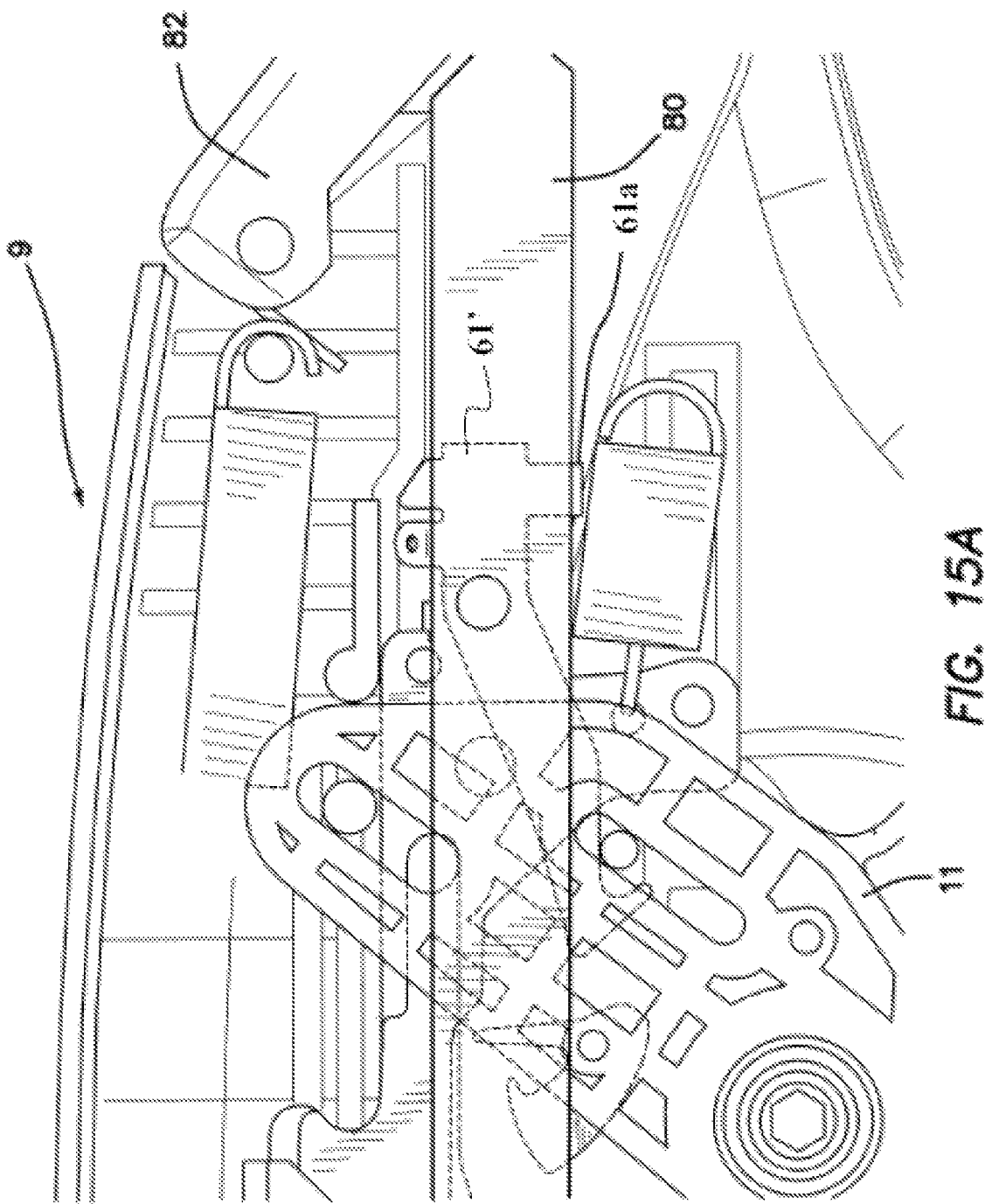

The firing lever 61 remains in the horizontal position, but is eventually deflected as shown in FIGS. 9-10. With the cartridge support 3 retracting, being urged by spring 91, the pin 55 also starts to or is allowed to move proximally causing the fire lock lever 71 to start to pivot. Also, with the pin 55 moving, the engagement of the fire lock lever 71 with the pin 55 starts to be released. Fire lock lever 71 and pin 55 typically interact to prevent the trigger from moving back distally or opening, even if the trigger is released. However, with the fire lock lever 71 disengaged from pin 55 the trigger is now allowed to open. The cartridge support 3 retracting also engages pin 51 to further cause the trigger to open (FIG. 11). FIG. 12 shows the stapler moved back to the original default or initial open position.

FIGS. 15A-D show an actuator 9 in accordance with various aspects of the present invention. The trigger 11 of the actuator 9 is used to advance the cartridge and fire staples from the cartridge 6. A release button 82 is also coupled to the actuator and is configured to reset the stapler back to its initial opened position at any time throughout operation of the stapler. As the trigger 11 is first actuated, the cartridge support 3 with the cartridge 6 and the staple member or pusher 14,15 advance towards the anvil 2. When the trigger 11 is fully actuated, the cartridge 6 is positioned at a specific distance to form staples against the anvil 2. Also, after the trigger 11 is released, the trigger engages the firing lever 61'. When the trigger 11 is actuated again, the firing lever connected the staple pusher 14,15 advances to eject the staples from the cartridge 6.

As previously noted, actuating the release button 82 can occur throughout the operation of the stapler. For example, as the stapler is ready to fire staples, e.g., after the first actuation of the trigger, the release button can be actuated. Since the firing lever 61' is already engaged or capable of being engaged by the trigger 11, a biasing mechanism 61a is provided to ensure that the firing lever is disengaged by the trigger irrespective of movement of the cartridge supports or staple or firing pusher 14,15. A protrusion or tab, in one aspect, provides the biasing mechanism. The tab extends from the firing lever 61' to ensure engagement with the release latch or arms 80 coupled to the release button 82 to bias the firing lever 61' directly when the release button is actuated. As such, activation of the button moves the release arms 80 that contact the tab 61a from the firing lever 61' disengaging the firing lever from pin 50.

Figure 16:
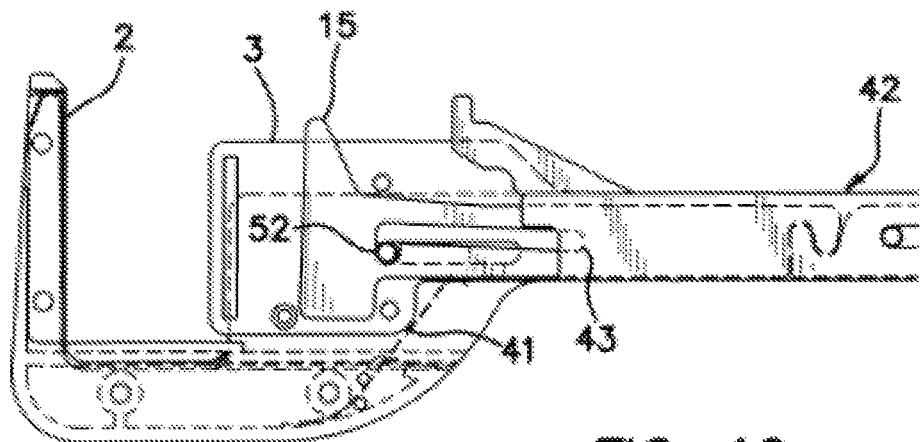
FIGS. 16-22 are side views of a surgical stapler in accordance with various aspects of the present invention.

In one aspect, a lockout mechanism is provided to prevent re-firing of a spent staple cartridge and re-clamping of tissue through interaction with a firing member and the disposable staple cartridge. Referring to FIG. 16, the stapler is shown without a loaded disposable cartridge 6. In this state, the staple pusher 14,15 pivots upward due to a biasing member 41, e.g., a spring, located in the frame of the stapler. The staple pusher in one aspect comprises a two-piece elongate structure, a proximal portion 14 and a distal portion 15. The proximal and distal portions of the staple pusher are connected at a mating connection or hooks 42. The mating hooks 42 allows the distal portion 15 of the staple pusher being biased by the spring 41 to pivot relative to the proximal portion 14 of the staple pusher. A projection, post or pin 52 disposed on the cartridge support 3 extends across a channel formed between the cartridge support 3 through which the staple pusher slides. The pin 52 extends through a generally L-shaped slot 43 in the staple pusher 15. The pin 52 attached or otherwise connected to the cartridge support 3 moves with the cartridge support 3. The engagement of pin 52 with the bottom or L-portion of the L-shaped slot prevents the staple pusher 14,15 from being moved towards the anvil 2. With the staple pusher being immobilized or otherwise prevented from moving, the cartridge support 3 movements are also restricted. Operationally, from the default initial open position to the closed or clamped position, the staple pusher 14,15 and cartridge support 3 movements are coupled to each other. As such, movement of the trigger 11 of actuator 9 causes movement of both the staple pusher 14,15 and cartridge support 3 away from the actuator 9 toward the anvil 2. The engagement of the pin 52 with the bottom portion of the L-shaped slot 43 in the staple pusher 14,15 also limits the distance or movement of the staple pusher being biased out of the stapler by spring 41.

Figure 17A:
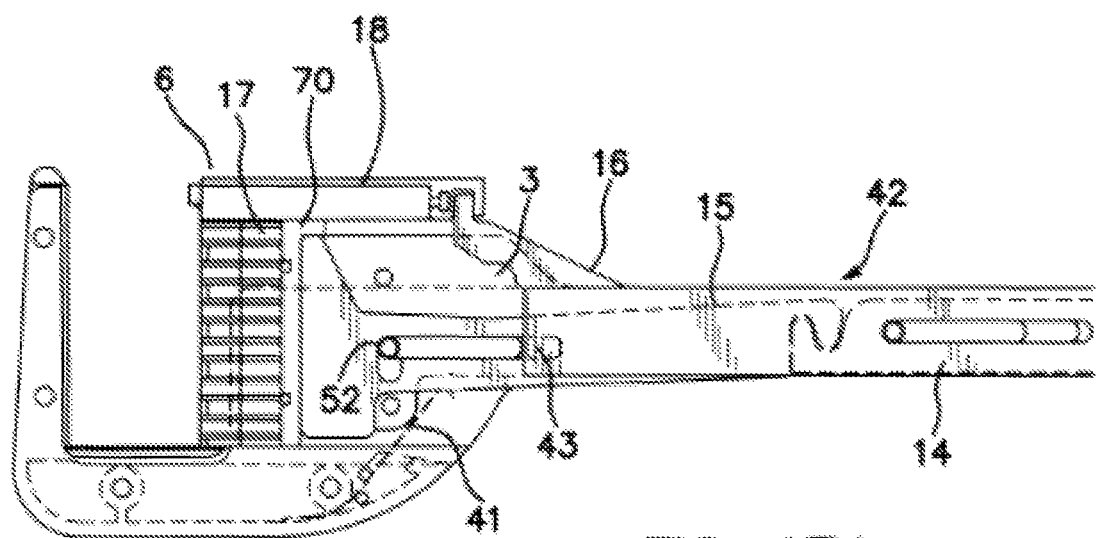
Figure 17B:
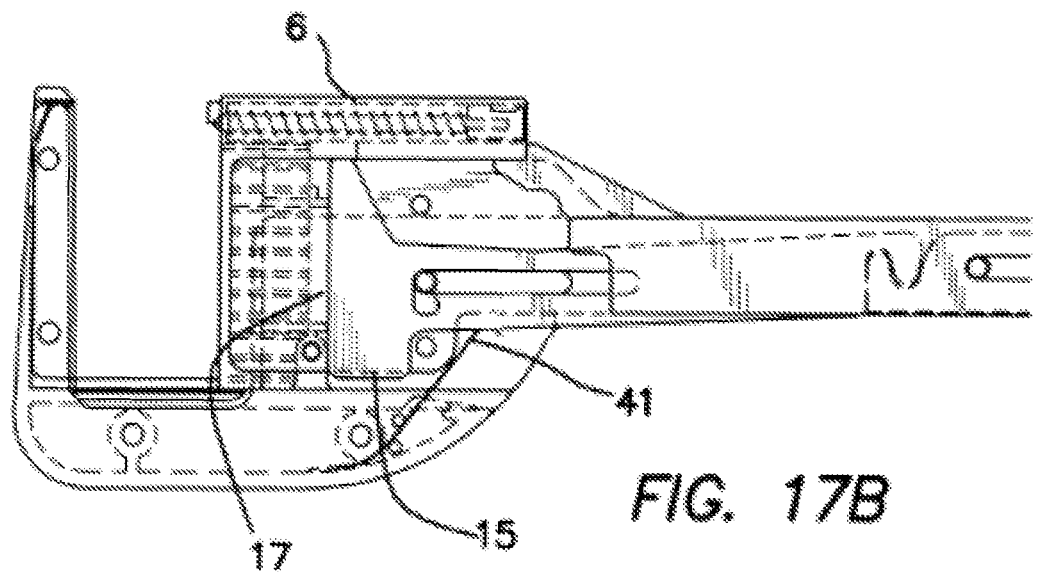

In FIG. 17A-B, the stapler is in an open or initial position and loaded with a staple filled or loaded cartridge 6. The staple driver(s) 17 disposed or included with the cartridge 6 that facilitate ejection or firing of the staples from the cartridge when contacted by the staple pusher 14,15. A portion of the staple driver(s), e.g., projection 70, engages the distal portion of the staple pusher deflecting or biasing the staple pusher downward against or counteracting the force of spring 41. This deflection also moves the bottom portion of the L-shaped slot 43 in staple pusher 14 substantially out of contact with pin 52. Thus, the staple pusher becomes unobstructed and free to move.

Figure 18:
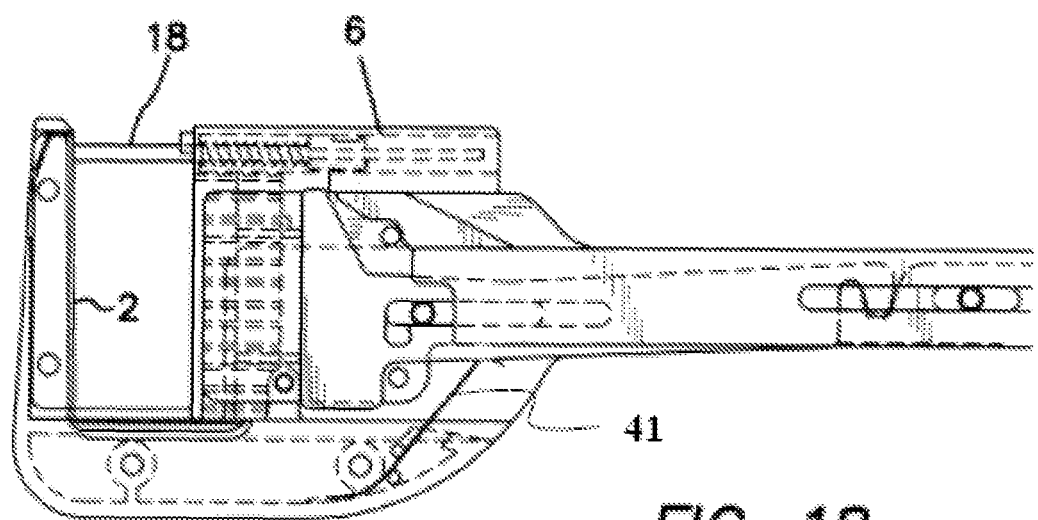
Figure 19:
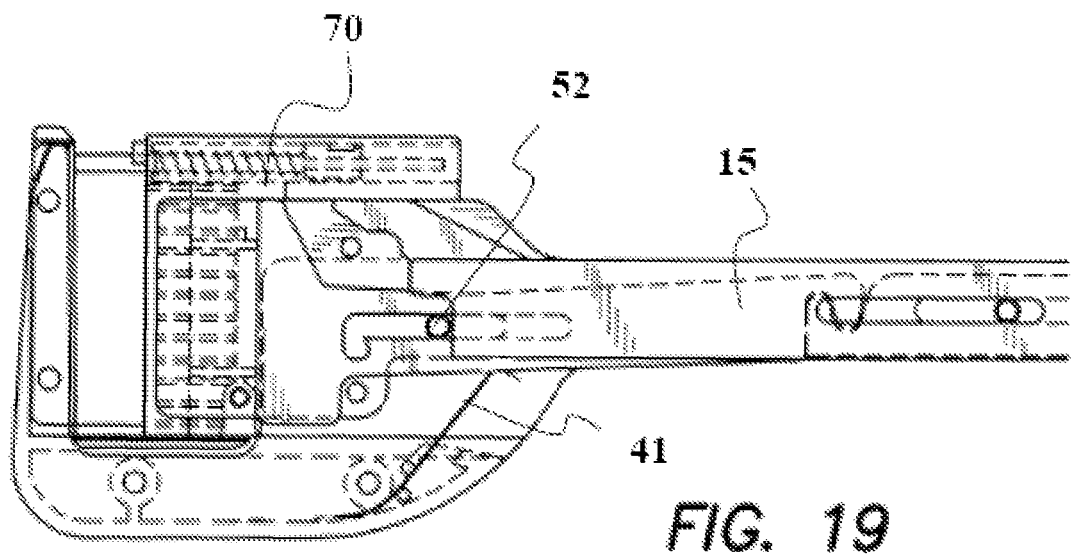
Figure 20:
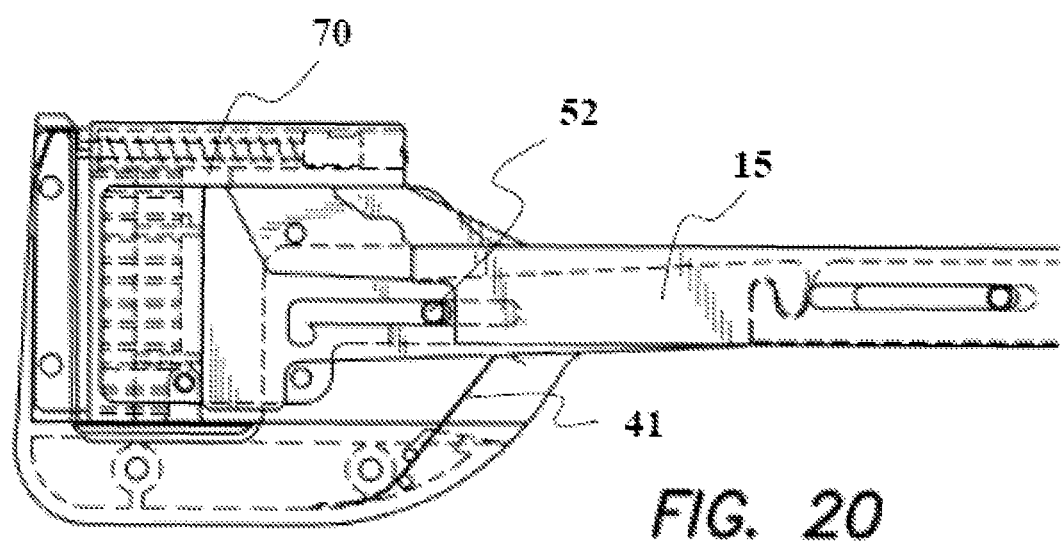
Figure 21:
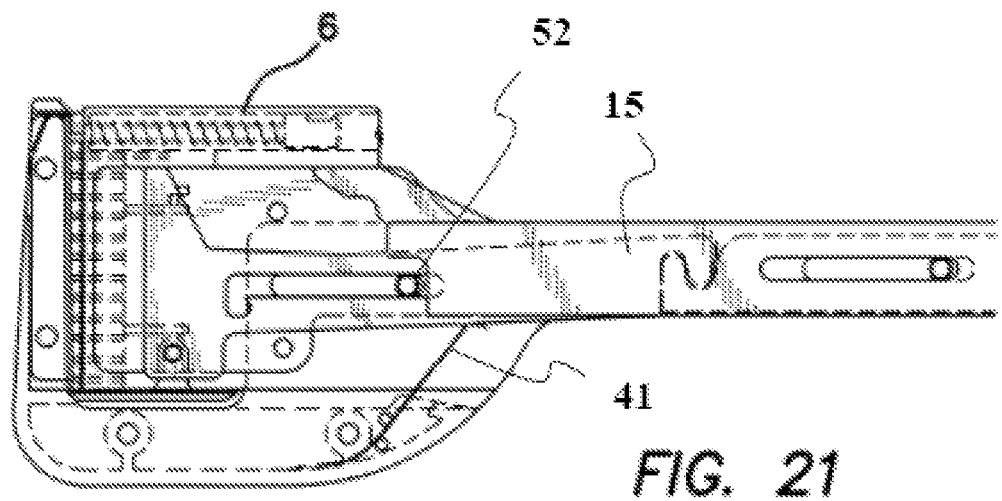

The stapler, in FIG. 18, is in the next stage of actuation or in the capture position with the capture pin advanced and the cartridge 6 moved towards the anvil 2. FIG. 19 shows the stapler being partially closed and FIG. 20 shows the stapler closed (tissue clamped). FIG. 21 shows the staples fired from the cartridge 6.

Figure 22:
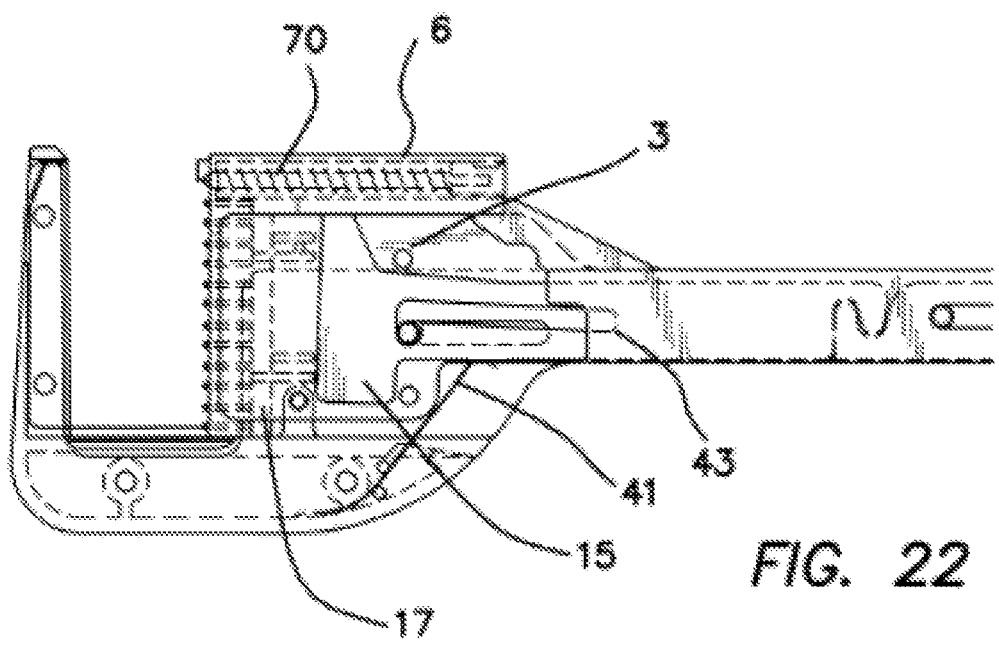

FIG. 22 shows the stapler opened or reset to allow removal of the stapler from the operation site or tissue. With the staple drivers 17 and thus projection 70 in their most distal position in the cartridge 6, the staple pusher 14,15 is permitted to pivot upward due to spring 41. Thus, the pin 52 engages the bottom portion of the L-shaped slot in the staple pusher 15, which prevents further distal movement of the staple pusher 14,15 and also cartridge support 3. Hence, re-firing of a spent or empty staple cartridge and re-clamping of tissue, i.e., preventing jaw closure, are prevented until a loaded cartridge is inserted between the cartridge support.

Figure 23:
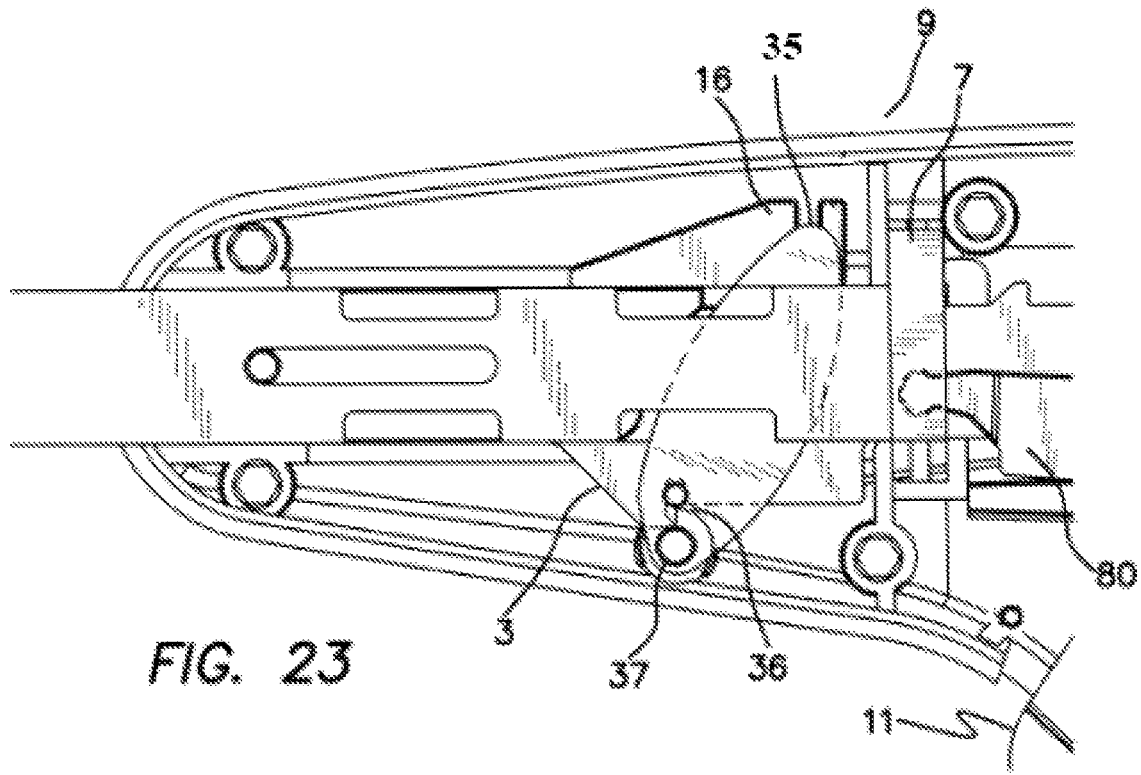
FIGS. 23-26 are side views of a surgical stapler in accordance with various aspects of the present invention.

As previously described and shown in the preceding figures, the capture pin 18 within cartridge 6 is operatively connected to the capture pin pusher or driver 16. In one aspect, as shown in FIG. 23, the capture pin pusher 16 has a slot 35 on one end, e.g., the proximal end, in which a pin or post extending from a pivot lever 34 connects the pivot lever 34 to the capture pin pusher 16. In the default or open position, a pin, detent or post 37 extending from the other end of the pivot lever 34 is operatively coupled to the cartridge support 3 via a slot 36 in the cartridge support 3. As shown in FIG. 23, the pin 37 extends from the lever and rests in the slot 36.

Figure 24:
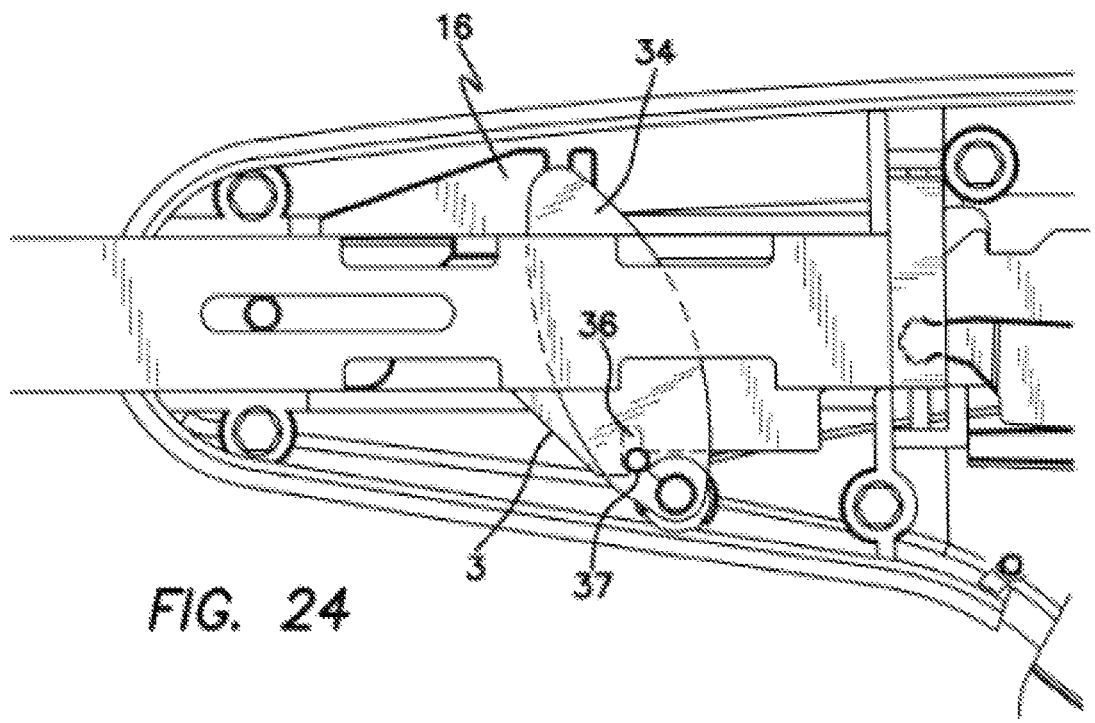
Figure 25:
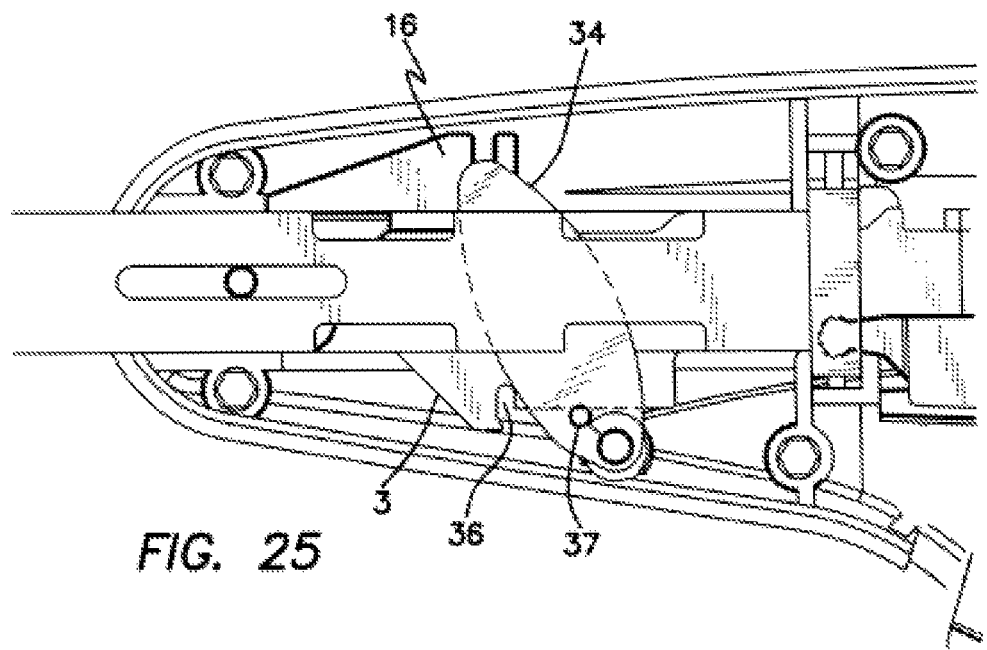
Figure 26:
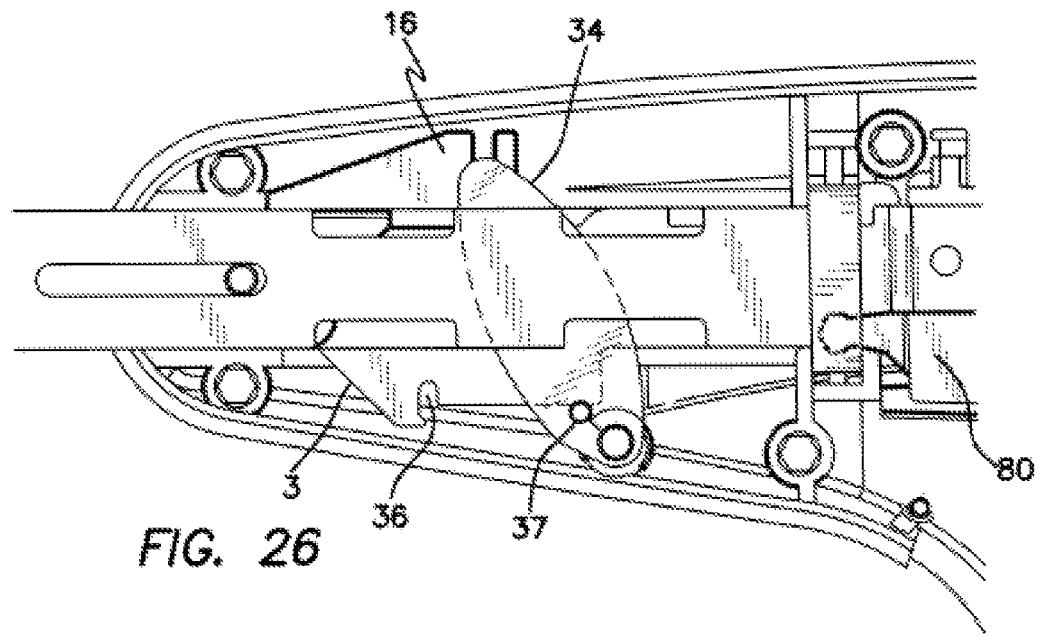

Movement of the trigger 11 of the actuator 9 causes the cartridge support 3 to move longitudinally as post 51 is moved by trigger 11. With the cartridge support 3 moving, the slot 36 in the cartridge support 3 interacts with the pin 37 of lever 34 causing the lever 34 to pivot in a counter-clockwise direction. Continued movement of lever 34 causes pin 37 to move out of the slot 36 (FIG. 24). The counter-clockwise motion of the lever 34 causes the capture pin pusher 16 via the interaction with the pin from lever 34 with the slot 35 in the capture pin pusher 16 to advance or move longitudinally, which in turn extends the capture pin 18 into the anvil 2 of jaw 4 capturing tissue within the space defined by the jaws/frame and capture pin. As shown in FIG. 25, the pin 37 rides along a surface of the cartridge support 3 as the cartridge support 3 is advanced distally to partially close the jaws. In and to the closed or clamped position of the stapler, as shown in FIG. 26, the pin 37 continues to slide along the surface of the cartridge support 3.

Figure 27:
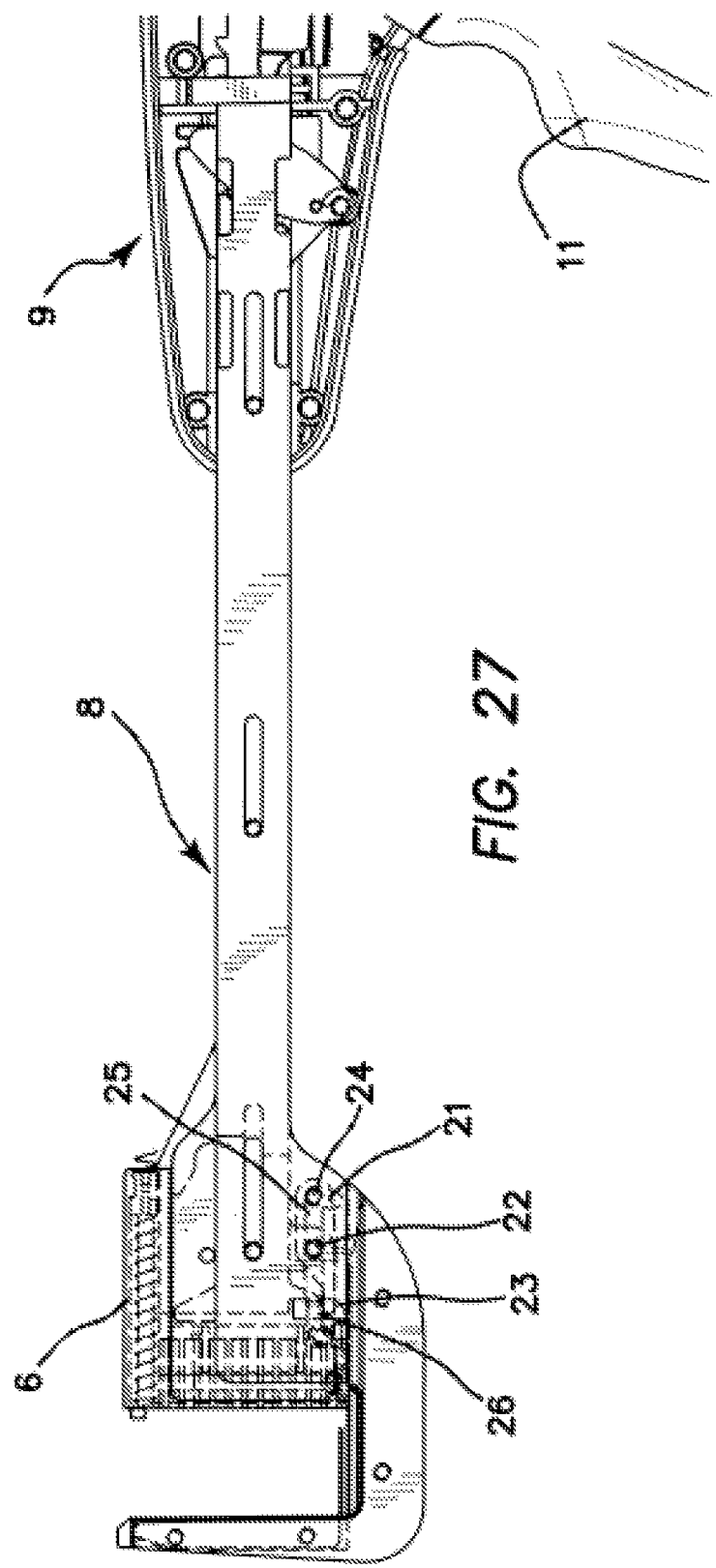

In FIG. 27, the stapler is in the open or initial position with a loaded cartridge, i.e., a cartridge having staples. In this position, the jaw 5 is allowed to move freely and staples may be fired. A lever 21 is pivotally connected to the cartridge support 3 via a rivet, pin or post 22. The lever 21 has a tip 23 that contacts a portion of the staple drivers or a protrusion 26 extending from the staple drivers to maintain a substantially horizontal position. The other end of the lever 21 has a pin 24 extending through an aperture 25 within the frame 10. The pin 24 slides along the aperture 25 as the cartridge support 3 is moved. Trigger 11 of actuator 9 is in an open position.

FIGS. 28A-B show the pin 24 sliding along the aperture 25 slightly and the lever 21 and tip 23 remaining substantially horizontal as the capture pin 31 driven by capture pin pusher 33 is extended into the anvil. Trigger 11 of actuator 9 and the jaws 4,5 are moved to a capture position. FIGS. 29A-B show the pin 24 continuing to slide along the aperture 25 and the lever 21 and tip 23 remaining substantially horizontal as the stapler continues to close. Trigger 11 of actuator 9 and the jaws 4,5 are moved to a partially closed position. FIGS. 30A-B show the pin 24 slide into the end of the aperture 25 and the lever 21 and tip 23 remaining substantially horizontal as the stapler is closed, clamping tissue between the jaws. Trigger 11 of actuator 9 and the jaws 4,5 are moved to a closed position.

FIG. 31 shows that the pin 24, lever 21 and tip 23 remain in the same position as the stapler is prepared to fire staples and the trigger 11 is moved back to an open position. FIGS. 32A-B show the pin 24, lever 21 and tip 23 remain in the same position as the stapler is fired and staples are ejected from the cartridge 6 with the trigger 11 moved back to a closed position. In this position, the protrusion 26 extending from the staple drivers moves with the staple drivers as the staples are fired and thus no longer contacts the tip 23 of lever 21. Thus, the aperture 25 within frame 10 contacting pin 24 maintains the lever 21 in a substantially horizontal position.

After firing, the stapler is reset in which the capture pin 31 and jaws 4,5 retract. As the cartridge support 3 retracts, the pin 24 slides along the aperture 25 until it reaches the proximal end of the aperture 25 where it is allowed to pivot. FIGS. 33A-B show the lever 21 pivoted, i.e., no longer in a horizontal position, with pin 24 moved in a lower part of an L-shaped portion of the aperture 25 of the cartridge support 3. The contact of pin 24 with the aperture 25 prevents longitudinal movement of the cartridge support even if the trigger 11 is actuated.

Figure 34:
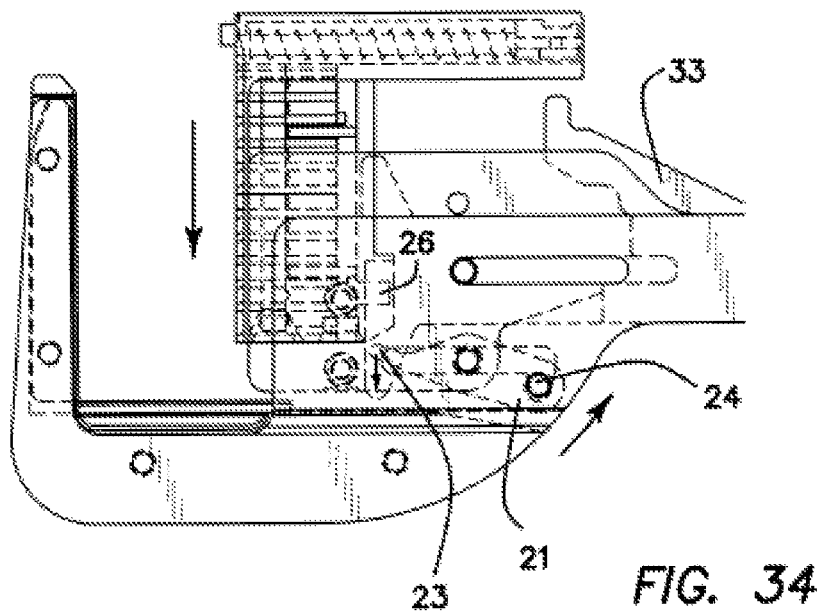
Figure 35:
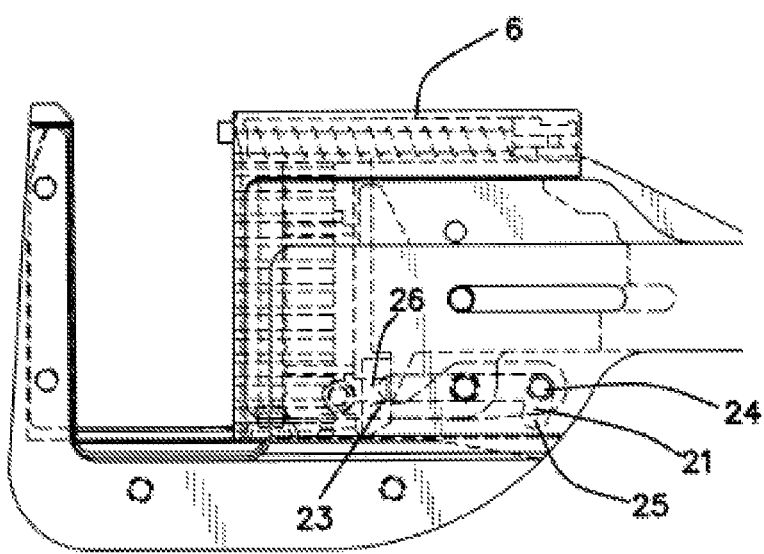

As shown in FIG. 34, when a loaded cartridge is inserted into the cartridge support 3, the protrusion 26 contacts tip 23 of lever 21 to causing the lever 21 to rotate and pin 24 to move out of the lower part of the aperture 25 placing lever 21 in a horizontal position (FIG. 35). In this position, the jaw 5 is allowed to move freely and staples within the cartridge 6 may be fired.

Figure 36:
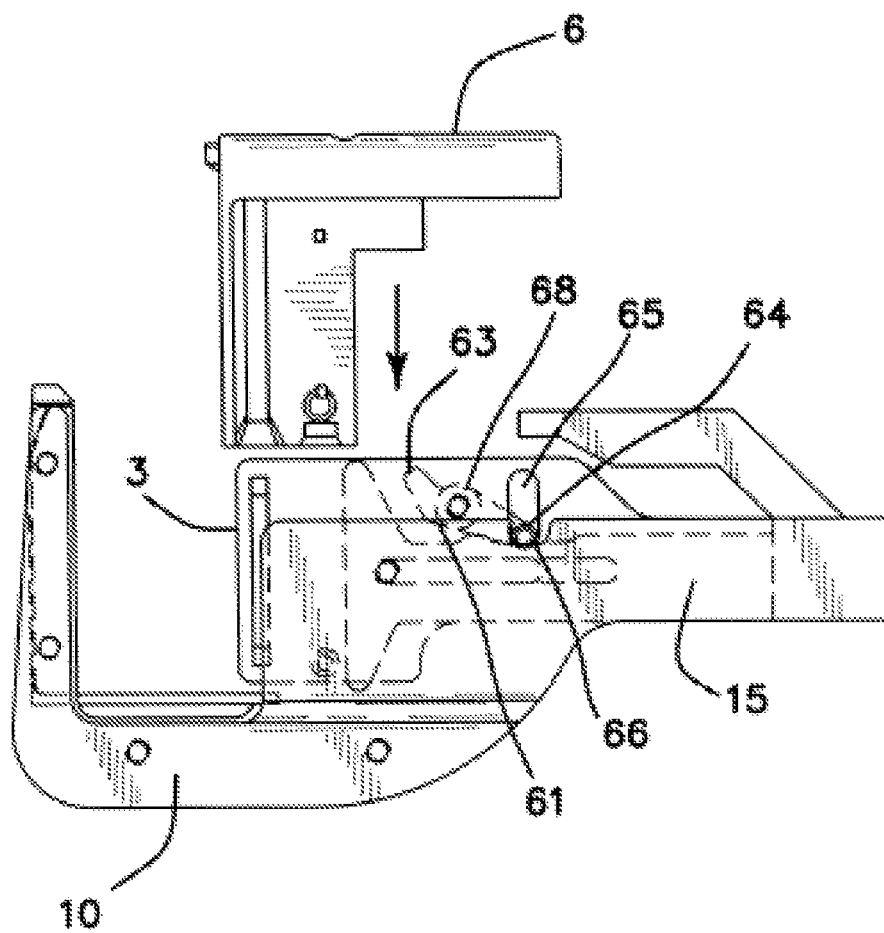
FIGS. 36-44 are side views of a surgical stapler in accordance with various aspects of the present invention.
Figure 37:
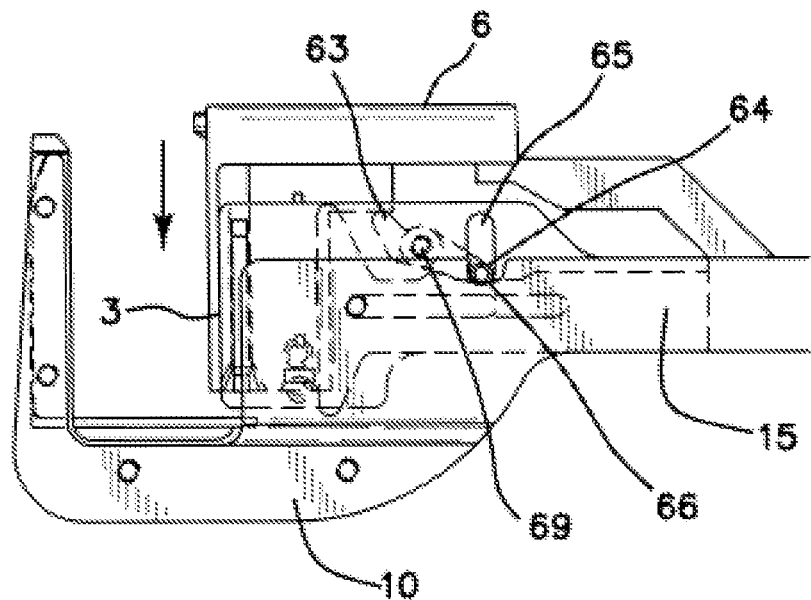
Figure 38:
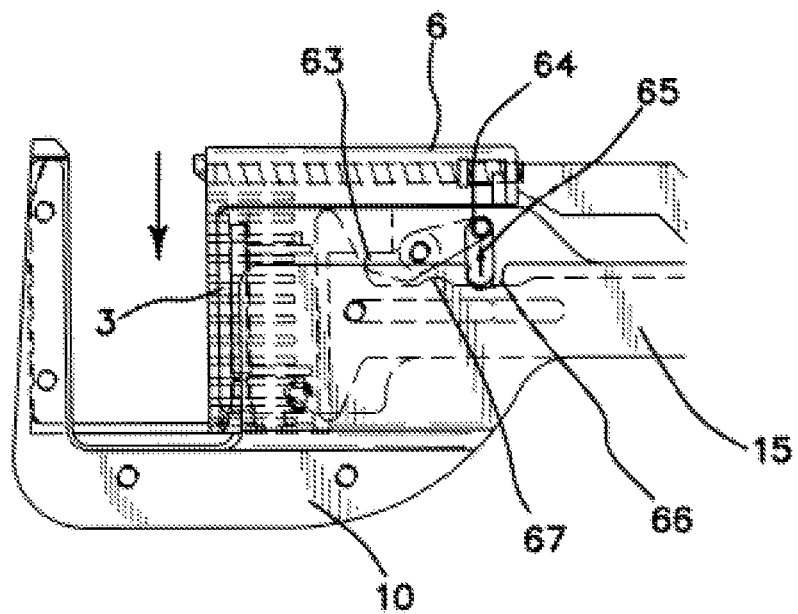
Figure 39:
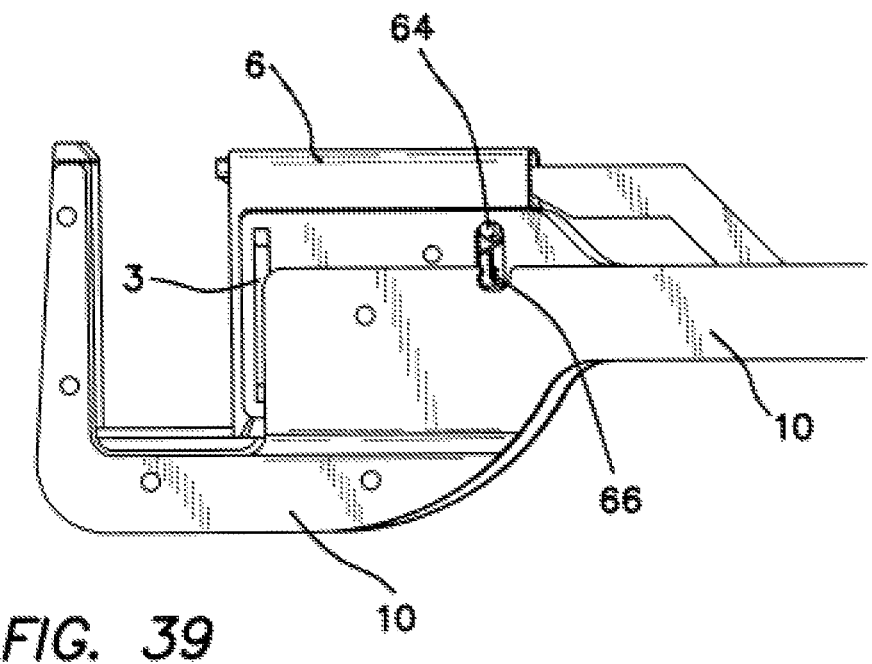

In FIG. 36, the stapler is in the open or initial position with a cartridge 6 being loaded into the stapler. In this position, the jaw 5 is not allowed to move freely and staples may not be fired. A pivotally connected lever 61 is connected to the cartridge support 3 via a rivet, pin or post 68. Without a cartridge loaded into the stapler, the lever 61 prevents movement of the jaws 5. A pin 64 extends from one end of the lever 61. The pin 64 extends through an aperture 65 of the cartridge support 3 and rests in a slot 66 of frame 10. As such, the pin 64 interacting with the cartridge support 3 and frame 10 prevents approximation of the jaw 5. In FIGS. 37-39, with a cartridge being loaded into the stapler, tip 63 of the lever 61 contacts a portion or protrusion (not shown) of the staple drivers or cartridge 6 causing rotation of the lever 61. As such, the pin 64 slides along the aperture 65 and out of the slot 66 of frame 10.

Figure 40:
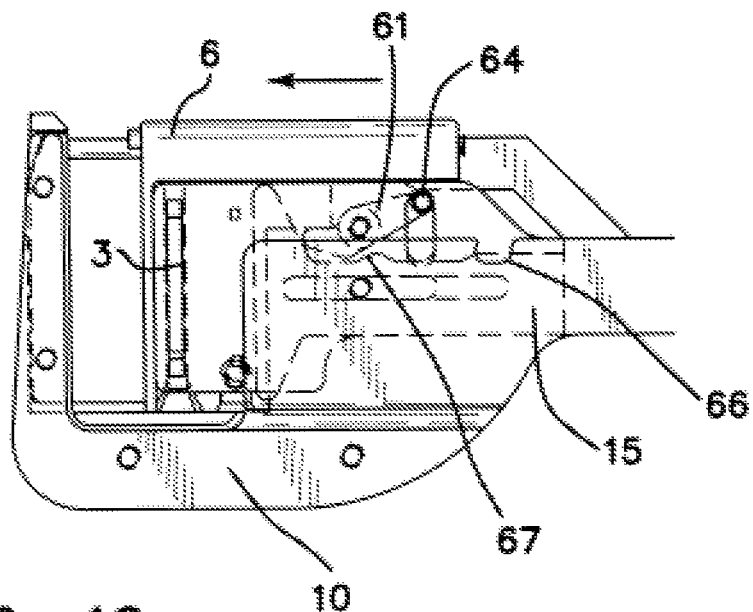
Figure 41:
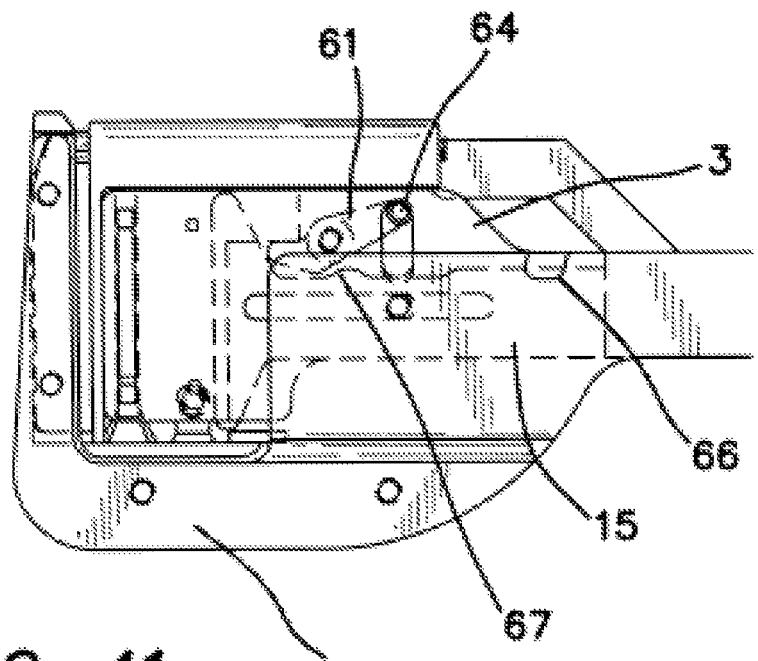
Figure 42:
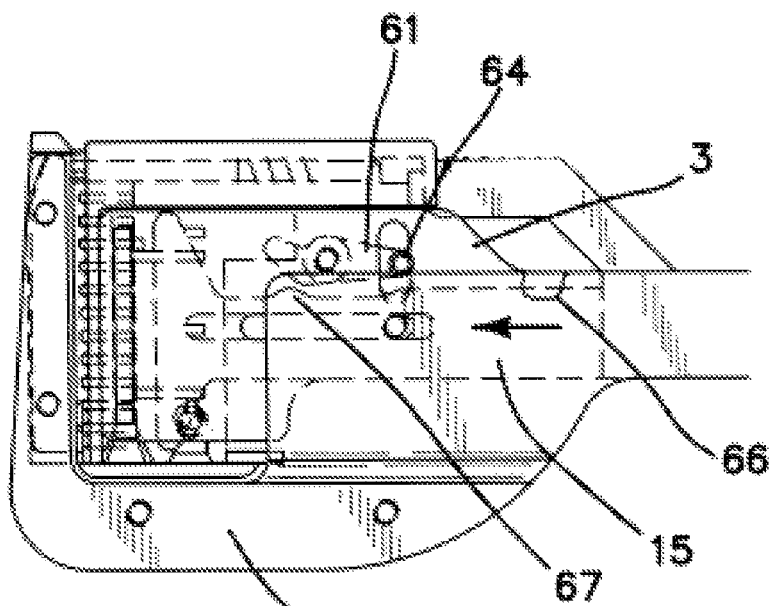

In FIGS. 40-41, the position of lever 61 is maintained as the capture or capture pin 31 is extended into the anvil. Likewise, as trigger 11 of actuator 9 and the jaws 4,5 are respectively moved to a capture position and subsequently to a closed position, the lever's position remains unchanged. Referring now to FIG. 42, as trigger 11 is manipulated to fire the stapler, the staple pusher 15 moves distally to push or drive the staples out of the cartridge 6. A projection or detent 67 extending from the staple pusher engages the lever 61 causing the lever 61 to pivot away from the staple pusher. Spring (not shown) assists in the pivoting of the lever, for example, by biasing the lever 61 in a clock-wise direction. The pin 64 slides along the aperture 65 until it contacts the frame preventing further rotation of the lever 61. As such, the lever 61 is generally parallel with the longitudinal axis of the staple and the frame 10.

Figure 43:
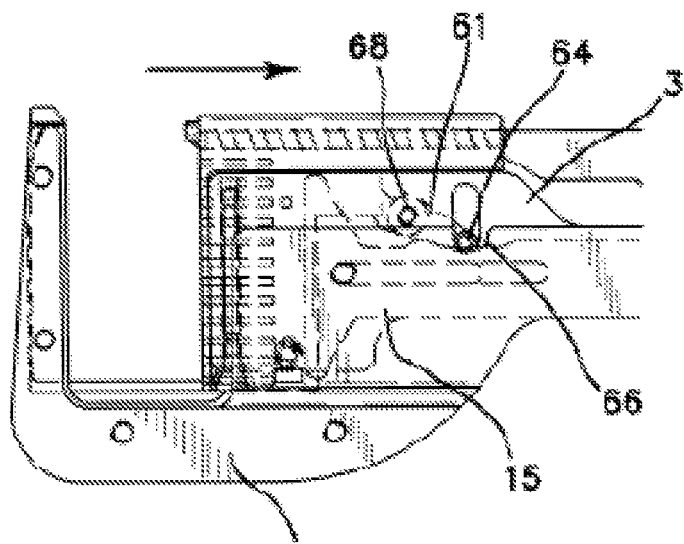
Figure 44:
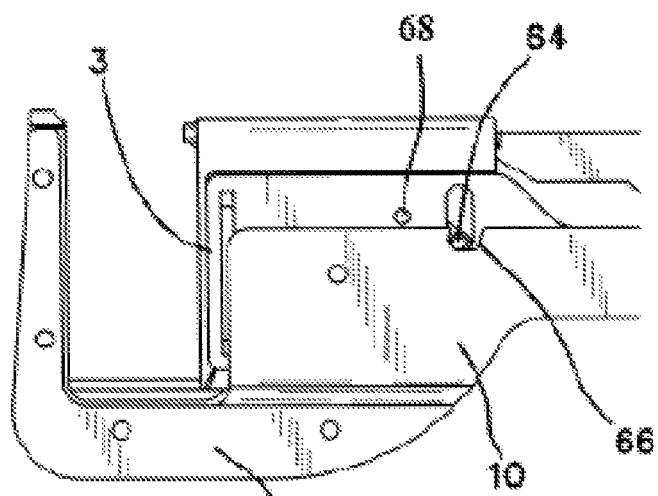

Referring now to FIGS. 43-44, after firing, the stapler is reset in which the capture pin 31 and jaws 4,5 retract. As the cartridge support 3 retracts, the pin 64 slides along the frame 10 until it reaches the slot 66 in which the lever 61 is then allowed to pivot back to its initial position. Pin 64 also slides along the aperture 65 until it reaches the end of the aperture 65. Pin 64 contacting the slot 66 in the frame prevents longitudinal movement of the cartridge support even if the trigger 11 is again actuated.

Accordingly, the present invention provides a surgical stapler. Although this invention has been described in certain specific embodiments, many additional modifications and variations would be apparent to those skilled in the art. It is therefore to be understood that this invention may be practiced otherwise than specifically described, including various changes in the size, shape and materials, without departing from the scope and spirit of the present invention. Thus, embodiments of the present invention should be considered in all respects as illustrative and not restrictive, the scope of the present invention to be determined by the appended claims and their equivalents rather than the foregoing description.

What is claimed is:

1. A stapler comprising:
   a handle assembly comprising:
   a stationary handle; and
   a trigger pivotably coupled to the stationary handle;
   a shaft extending longitudinally from a proximal end with the handle assembly connected thereto to a distal end;
   a cartridge support extending within the shaft from a proximal end within the handle assembly to a distal end at the distal end of the shaft, the cartridge support movable within the shaft by pivotal movement of the trigger relative to the stationary handle;
   a capture member pusher extending within the shaft from a proximal end within the handle assembly to the distal end of the shaft; and
   a pivot lever positioned in the handle assembly, the pivot lever having a first end pivotally coupled to the proximal end of the capture member pusher and a second end opposite the first end, the second end operatively coupled to the cartridge support such that longitudinal movement of the cartridge support pivots the pivot lever to drive the capture member pusher generally longitudinally to a deployed position,
   wherein the proximal end of the cartridge support further comprises a slot formed therein;
   wherein the second end of the pivot lever comprises a pin extending therefrom coupled to the slot in the cartridge support; and
   wherein the pin extending from the second end of the pivot lever is releasably coupled to the slot formed in the cartridge support such that the pin moves out of the slot formed in the cartridge support upon further longitudinal advancement of the cartridge support once the capture member pusher is in the deployed position.

2. The stapler of claim 1, wherein the capture member pusher further comprises a slot formed therein at the proximal end thereof.

3. The stapler of claim 2, wherein the first end of the pivot lever comprises a pin extending therefrom coupled to the slot in the capture member pusher.

4. The stapler of claim 1, wherein further comprising a cartridge removably positionable at the distal end of the cartridge support, the cartridge comprising a capture pin couplable to the capture member pusher when the cartridge is positioned at the distal end of the cartridge support.

5. A stapler comprising:
   a handle assembly comprising:
   a stationary handle; and
   a trigger pivotably coupled to the stationary handle;
   a shaft extending longitudinally from a proximal end with the handle assembly connected thereto to a distal end;
   a cartridge support extending within the shaft from a proximal end within the handle assembly to the distal end of the shaft, the cartridge support movable within the shaft by pivotal movement of the trigger relative to the stationary handle, and the proximal end of the cartridge support comprising a plurality of slots; and
   a latch selectively engageable in each one of the plurality of slots to maintain the cartridge support in a corresponding predetermined position,
   wherein at least one of the plurality of slots comprises a sloped surface such that longitudinal movement of the cartridge support in a first direction advances the latch over the sloped surface to disengage the latch from the at least one of the plurality of slots, and the at least one of the plurality of slots further comprises an edge opposite the sloped surface such that longitudinal movement of the cartridge support in a second direction opposite the first direction is prevented by engagement of the latch with the edge.

6. The stapler of claim 5, wherein the sloped surface is proximal the edge such that the latch allows distal advancement of the cartridge support relative to the shaft and restricts proximal retraction of the of the cartridge support relative to the shaft.

7. The stapler of claim 5, wherein the stationary handle comprises a channel formed therein, and wherein the latch is disposed within the channel.

8. The stapler of claim 7, wherein the channel restricts the latch from longitudinal movement and allows movement of the latch perpendicularly to longitudinal movement.

9. The stapler of claim 8, further comprising a release mechanism to selectively disengage the latch from one of the plurality of slots.

10. The stapler of claim 9, wherein the release mechanism comprises a release button coupled to a release latch positioned to lift the latch within the channel out of engagement with the plurality of slots upon actuation of the release button.

11. The stapler of claim 10, wherein the latch is biased to engage the cartridge support by a compression spring.

12. The stapler of claim 5, further comprising a release mechanism to selectively disengage the latch from one of the plurality of slots.

\* \* \* \* \*